US009034643B2

(12) United States Patent
Lin et al.

(10) Patent No.: US 9,034,643 B2
(45) Date of Patent: May 19, 2015

(54) CONNECTIVE TISSUE GROWTH FACTOR ANTIBODIES

(71) Applicant: FibroGen, Inc., San Francisco, CA (US)

(72) Inventors: Al Y. Lin, San Francisco, CA (US); Thomas B. Neff, San Francisco, CA (US); Noelynn A. Oliver, Ridgefield, CT (US); William R. Usinger, Lafayette, CA (US); Qingjian Wang, Belmont, CA (US); David A. Yeowell, San Francisco, CA (US)

(73) Assignee: FibroGen, Inc., San Francisco, CA (US)

( * ) Notice: Subject to any disclaimer, the term of this patent is extended or adjusted under 35 U.S.C. 154(b) by 0 days.

(21) Appl. No.: 13/691,356

(22) Filed: Nov. 30, 2012

(65) Prior Publication Data

US 2014/0073047 A1   Mar. 13, 2014

Related U.S. Application Data

(60) Division of application No. 12/927,243, filed on Nov. 10, 2010, now abandoned, and a continuation of application No. 12/157,262, filed on Jun. 9, 2008, now Pat. No. 7,871,617, and a continuation of application No. 10/858,186, filed on Jun. 1, 2004, now Pat. No. 7,405,274.

(60) Provisional application No. 60/475,598, filed on Jun. 4, 2003.

(51) Int. Cl.
| | |
|---|---|
| C12P 21/06 | (2006.01) |
| C12N 15/12 | (2006.01) |
| C12N 5/12 | (2006.01) |
| C12N 15/13 | (2006.01) |
| C12N 5/10 | (2006.01) |
| C07H 21/04 | (2006.01) |
| C07K 16/22 | (2006.01) |
| A61K 39/00 | (2006.01) |

(52) U.S. Cl.
CPC ........... *C07K 16/22* (2013.01); *A61K 2039/505* (2013.01); *C07K 2316/96* (2013.01)

(58) Field of Classification Search
None
See application file for complete search history.

(56) References Cited

U.S. PATENT DOCUMENTS

| | | | |
|---|---|---|---|
| 5,408,040 A | 4/1995 | Grotendorst et al. | |
| 5,770,209 A | 6/1998 | Grotendorst et al. | |
| 5,783,187 A | 7/1998 | Grotendorst et al. | |
| 6,464,983 B1 | 10/2002 | Grotendorst | |
| 6,562,618 B1 | 5/2003 | Tamatani et al. | |
| 2003/0113816 A1* | 6/2003 | Weitz et al. | 435/7.9 |
| 2007/0083334 A1 | 4/2007 | Mintz et al. | |

FOREIGN PATENT DOCUMENTS

| | | |
|---|---|---|
| EP | 1 043 335 A1 | 10/2000 |
| WO | WO-99/07407 A1 | 2/1999 |
| WO | WO-99/13910 A1 | 2/1999 |
| WO | WO-00/13706 A1 | 3/2000 |
| WO | WO-00/35936 A1 | 6/2000 |
| WO | WO-00/35939 A2 | 6/2000 |
| WO | WO-03/024308 A2 | 3/2003 |
| WO | WO-03/049773 A1 | 6/2003 |

OTHER PUBLICATIONS

Duncan, Matthew R., et al., "Connective Tissue Growth Factor Mediates Transforming Growth Factor β-Induced Collagen Synthesis: Down-Regulation by cAMP," FASEB J. (1999) 13:1774-1786.
Kang, Angray S., et al., "Antibody Redesign by Chain Shuffling From Random Combinatorial Immunoglobin Libraries," PNAS (1991) 88;1120-1123.
Ledermann, Seth, et al., "A Single Amino Acid Substitution in a Common African Allele of the CD4 Molecule Ablates Binding of the Monoclonal Antibody OKT4," Mol Immunol (1991) 28:1171-1181.
Li, Choh Hao, et al., "β-Endorphin Omission Analogs: Disassociation of Immunoreactivity from Other Biological Activities," PNAS (1980) 77(6):3211-3214.
Li, Yili, et al., "Three-Dimensional Structures of the Free and Antigen-Bound Fab From the Monoclonal Antilysozyme Antibody HyHEL-63," Biochem (2000) 39:6296-6309.
Mercurio, Sara, et al., "Connective-Tissue Growth Factor Modulates WNT Signalling and Interacts With the WNT Receptor Complex," Development (2004) 131(9):2137-2147.
Shimo, T., et al., "Involvement of CTGF, a Hypertrophic Chondrocyte-Specific Gene Product, in Tumor Angiogenesis," Oncology (2001) 61:315-322.
Steffen, Christy L., et al., "Characterization of Cell-Associated and Soluble Forms of Connective Tissue Growth Factor (CTGF) Produced by Fibroblast Cells in Vitro," Growth Factor (1998) 15:199-213.
Usinger, William R, et al., "TGFβ2 Binds CTGF Specifically and is Inhibited by a CTGF Neutralizing Antibody, FG-3019," J Am Soc Nephrol (2001) 14:374A.
Padlan, Eduardo A., et al., "Identification of Specificity-Determining Residues in Antibodies," FASEB J (1995) 128(9):133-139.
Wright, Ann and Morrison, Sherie L., "Effect of Glycosylation on Antibody Function: Implications for Genetic Engineering," TIBTECH (1997) 15:26-32.
Lam, Suzanne, et al., "Connective Tissue Growth Factor and IGF-1 are Produced by Human Renal Fibroblasts and Cooperate in the Induction of Collagen Production by High Glucose," Diabetes (2003) 52:2975-2983.
Wang et al., J Am Soc Nephrol 13:315A, Abstract SA-P0254, Sep. 2002.

\* cited by examiner

*Primary Examiner* — Marianne P Allen

(57) ABSTRACT

The present invention relates to antibodies that bind to CTGF. The antibodies are particularly directed to regions of CTGF involved in biological activities associated with fibrosis. The invention also relates to methods of using the antibodies to treat disorders associated with CTGF including localized and systemic fibrotic disorders including those of the lung, liver, heart, skin, and kidney.

12 Claims, 14 Drawing Sheets

```
                                                  ─────────── EXON 2 ───────────
                                                  │
                                                  IGF-Binding Protein Motif
hCTGF    MTAASMGPVRVAFVVLLALCSRPAVGQNCSGPCRCPDEPAPRCPAGVSLVLDGCGCCRVCAKQLGE   66
bCTGF    MSATGLGPVRCAFVLLLALCSRPASSQDCSAPCQCPAGPAPRCPAGVSLVLDGCGCCRVCAKQLSE   66
pCTGF    MSATGLSPVRCAFVLLLALCSRPASGQDCSGQCQCAAGKRRACPAGVSLVLDGCGCCRLCAKQLGE   66
rCTGF    MLASVAGPVSLALVLL--LCTRPATGQDCSAQCQCAAEAAPRCPAGVSLVLDGCGCCRVCAKQLGE   64
FISP12   MLASVAGPISLALVLLA-LCTRPATGQDCSAQCQCAAEAAPHCPAGVSLVLDGCGCCRVCAKQLGE   65
          *  *;   .*;   *;*;*   **;***  .  *;**.  *;*.   ******************;*****.*

─────── EXON 2 ───────                   ──────────── EXON 3 ────────────
         IGF-BP Motif                             von Willebrand Type C Domain
hCTGF    LCTERDPCDPHKGLFCDFGSPANRKIGVCTAKDGAP                                      132
bCTGF    LCTERDPCDPHKGLFCDFGSPANRKIGVCTAKDGAP                                      132
pCTGF    LCTERDPCDPHKGLFCDFGSPANRKIGVCTAKDGAP                                      132
rCTGF    LCTERDPCDPHKGLFCDFGSPANRKIGVCTAKDGAP                                      130
FISP12   LCTERDPCDPHKGLFCDFGSPANRKIGVCTAKDGAP                                      131
         ************************************  ***.**;*.***************;****.**

──────────── EXON 3 ────────────
         CLN1 EPITOPE
hCTGF                                        VCDEPKDQTVVGPALAAYRLEDTFGPDPTMIRAN   198
bCTGF                                        VCDEPKEHTVVGPALAAYRPEDTFGPDPTMIRAN   198
pCTGF                                        VCDEPKDHTVVGPALAAYRLEDTFGPDPTMMRAN   198
rCTGF                                        VCDEPKDRTVVGPALAAYRLEDTFGPDPTMMRAN   196
FISP12                                       VCDEPKDRTAVGPALAAYRLEDTFGPDPTMMRAN   197
          *;****.********************;*******;;*.********** **********;***

FIG. 1B
```

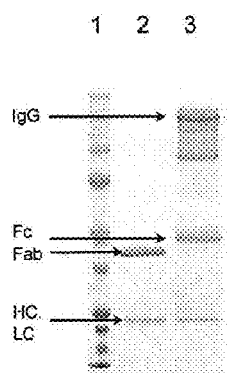
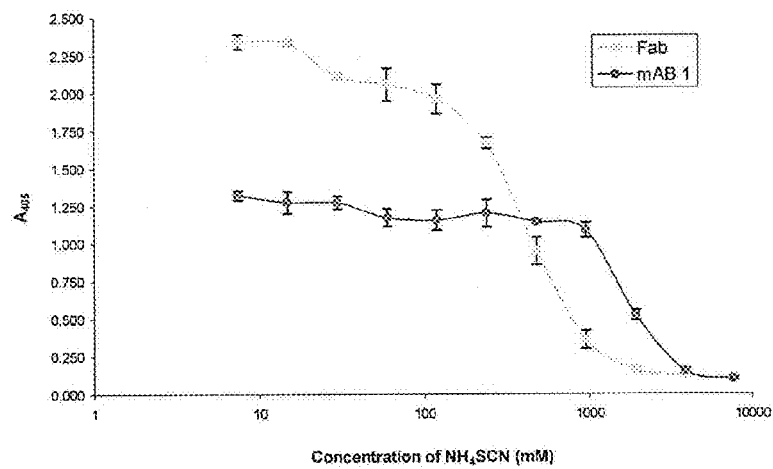
FIG. 3A
FIG. 3B

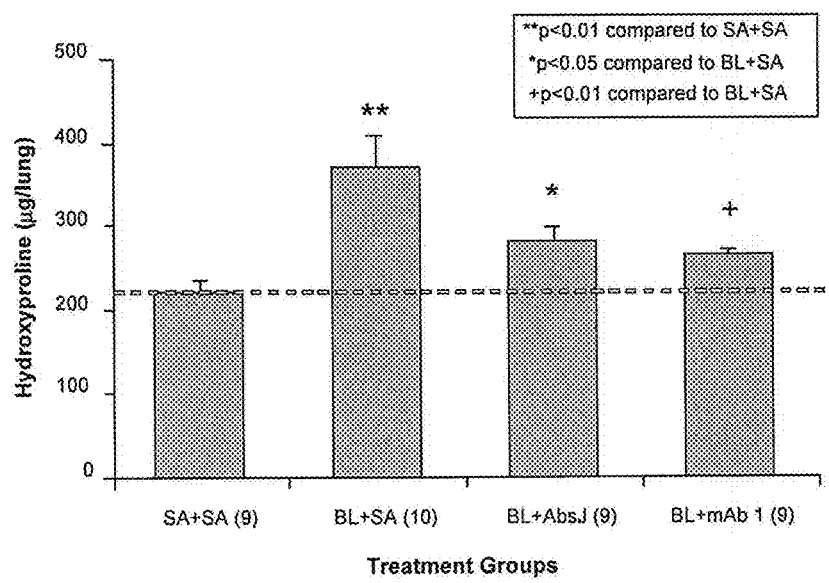
FIG. 5A
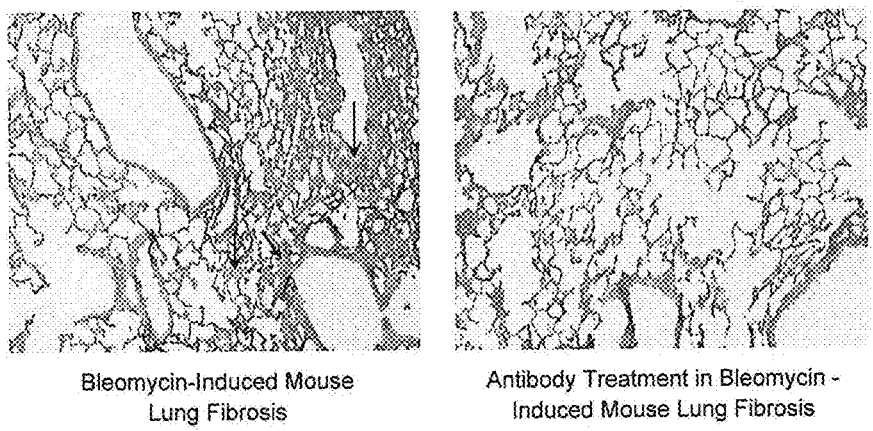
Bleomycin-Induced Mouse
Lung Fibrosis
Antibody Treatment in Bleomycin -
Induced Mouse Lung Fibrosis
FIG. 5B
FIG. 5C

5/6 NEPHRECTOMY

Saline Treated (Day 18)

Antibody Treated (Day 18)

TGFβ

TGFβ + CTGF

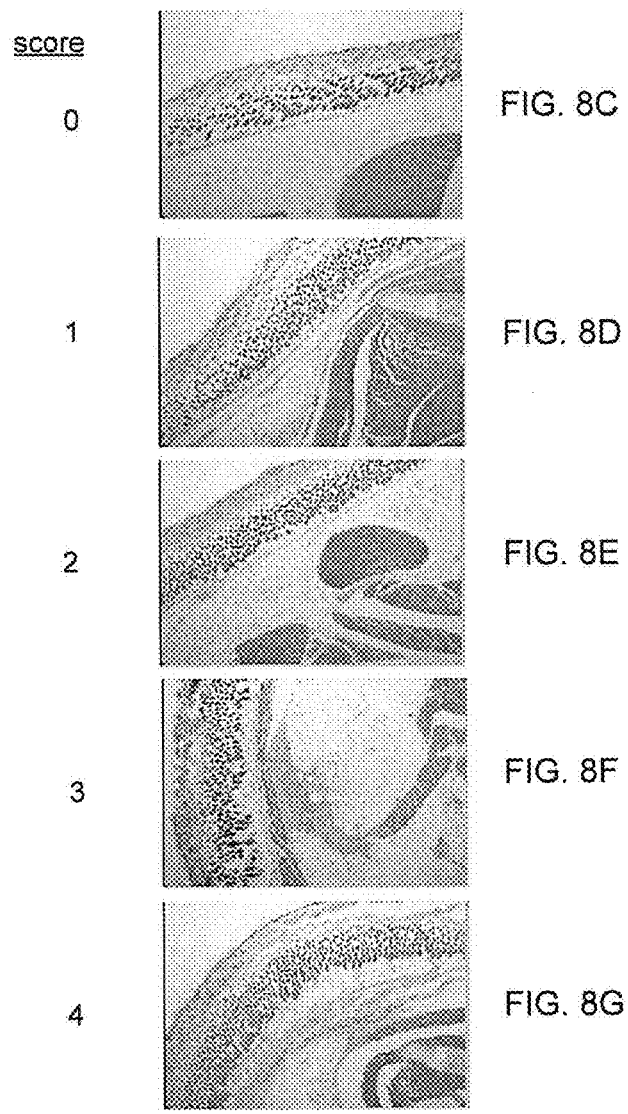

CONNECTIVE TISSUE GROWTH FACTOR ANTIBODIES

This application is a divisional of U.S. application Ser. No. 12/927,243, filed 10 Nov. 2010, now abandoned, which is a continuation of U.S. application Ser. No. 12/157,262, filed 9 Jun. 2008, now U.S. Pat. No. 7,871,617, which is a continuation of U.S. Application Ser. No. 10/858,186, filed 1 Jun. 2004, now U.S. Pat. No. 7,405,274, which claims the benefit of U.S. Provisional Application Ser. No. 60/475,598, filed on 4 Jun. 2003, incorporated in their entireties by reference herein.

FIELD OF THE INVENTION

The present invention relates to antibodies that bind to connective tissue growth factor (CTGF). The antibodies are particularly directed to regions of CTGF involved in biological activities associated with various disorders.

BACKGROUND

Connective Tissue Growth Factor (CTGF)

CTGF is a 36 kD, cysteine-rich, heparin binding, secreted glycoprotein originally isolated from the culture media of human umbilical vein endothelial cells. (See e.g. Bradham et al. (1991) J Cell Biol 114:1285-1294; Grotendorst and Bradham, U.S. Pat. No. 5,408,040.) CTGF belongs to the CCN (CTGF, Cyr61, Nov) family of proteins (secreted glycoproteins), which includes the serum-induced immediate early gene product Cyr61, the putative oncogene Nov, the ECM-associated protein FISP-12, the src-inducible gene CEF-10, the Wnt-inducible secreted protein WISP-3, and the anti-proliferative protein HICP/rCOP (Brigstock (1999) Endocr Rev 20:189-206; O'Brian et al. (1990) Mol Cell Biol 10:3569-3577; Joliot et al. (1992) Mol Cell Biol 12:10-21; Ryseck et al. (1990) Cell Growth and Diff 2:225-233; Simmons et al. (1989) Proc Natl Acad Sci USA 86:1178-1182; Pennica et al. (1998) Proc Natl Acad Sci USA, 95:14717-14722; and Zhang et al. (1998) Mol Cell Biol 18:6131-6141.) CCN proteins are characterized by conservation of 38 cysteine residues that constitute over 10% of the total amino acid content and give rise to a modular structure with N- and C-terminal domains. The modular structure of CTGF includes conserved motifs for insulin-like growth factor binding protein (IGF-BP) and von Willebrand's factor (VWC) in the N-terminal domain, and thrombospondin (TSP1) and a cysteine-knot motif in the C-terminal domain.

CTGF expression is induced by members of the Transforming Growth Factor beta (TGFβ) superfamily, which includes TGFβ-1, -2, and -3, bone morphogenetic protein (BMP)-2, and activin, as well as a variety of other regulatory modulators including dexamethasone, thrombin, vascular endothelial growth factor (VEGF), and angiotensin II; and environmental stimuli including hyperglycemia and hypertension. (See, e.g., Franklin (1997) Int J Biochem Cell Biol 29:79-89; Wunderlich (2000) Graefes Arch Clin Exp Ophthalmol 238:910-915; Denton and Abraham (2001) Curr Opin Rheumatol 13:505-511; and Riewald (2001) Blood 97:3109-3116; Riser et al. (2000). J Arm Soc Nephrol 11:25-38; and International Publication No. WO 00/13706). TGFβ stimulation of CTGF expression is rapid and prolonged, and does not require persistent application. (Igarashi et al. (1993) Mol Biol Cell 4: 637-645.) Enhanced expression of CTGF by TGFβ involves transcriptional activation via DNA regulatory elements present in the CTGF promoter. (Grotendorst et al. (1996) Cell Growth Differ 7: 469-480; Grotendorst and Bradham, U.S. Pat. No. 6,069,006; Holmes et al. (2001) J Biol Chem 276:10594-10601.)

CTGF has been shown to increase steady-state transcription of α1(I) collagen, α5 integrin, and fibronectin mRNAs, as well as to promote cellular processes including proliferation and chemotaxis of various cell types in culture. (See e.g., Frazier et al. (1996) J Invest Dermatol 107:406-411; Shi-wen et al. (2000) Exp Cell Res 259:213-224; Klagsburn (1977) Exp Cell Res 105:99-108; Gupta et al. (2000) Kidney Int 58:1389-1399; Wahab et al. (2001) Biochem J 359(Pt 1):77-87; Uzel et al. (2001) J Periodontol 72:921-931; and Riser and Cortes (2001) Ren Fait 23:459-470.) Subcutaneous injection of CTGF in neonatal mice results in the local deposition of granulation tissue. Similarly, subcutaneous injection of TGFβ generates granulation tissue formation and induces high levels of CTGF mRNA in local fibroblasts. Moreover, combination or sequential treatment with TGFβ and CTGF results in the development of a more persistent granuloma. (Mori at al, (1999) J Cell Physiol 181:153-159.) Thus, CTGF appears to mediate a subset of the effects elicited by TGFβ, in particular, the production and deposition of extracellular matrix (ECM). Further, the ability to respond to CTGF, or the extent of the CTGF response, may rely upon a priming stimulus provided by TGFβ treatment that enables cellular "competence." (International Publication No. WO 96/08140.)

Although a plethora of interacting factors have been characterized that modulate tissue organization, a consensus is now emerging for the role of CTGF in regulating skeletal development wound healing and extracellular matrix (ECM) remodeling, fibrosis, tumorigenesis, and angiogenesis. For example, elevated CTGF expression has been observed in cirrhotic liver, pulmonary fibrosis, inflammatory bowel disease, sclerotic skin and keloids, desmoplasia, and atherosclerotic plaques. (Abraham et al. (2000) J Biol Chem 275: 15220-15225; Dammeier et al. (1998) Int J Biochem Cell Biol 30:909-922; diMola et al. (1999) Ann Surg 230(1):63-71; Igarashi et al. (1996) J Invest Dermatol 106:729-733; Ito et al. (1998) Kidney Int 53:853-861; Williams et al. (2000) J Hepatol 32:754-761; Clarkson et al. (1999) Curr Opin Nephrol Hypertens 8:543-548; Hinton et al. (2002) Eye 16:422-428; Gupta et al. (2000) Kidney Int 58:1389-1399; Riser et al. (2000) J Am Soc Nephrol 11:25-38.)

CTGF is also upregulated glomerulonephritis, IgA nephropathy, focal and segmental glomerulosclerosis and diabetic nephropathy. (See, e.g., Riser et al. (2000) J Am Soc Nephrol 11:25-38.) An increase in the number of cells expressing CTGF is also observed at sites of chronic tubulointerstitial damage, and CTGF levels correlate with the degree of damage. (Ito et al. (1998) Kidney Int 53:853-861.) Further, CTGF expression is increased in the glomeruli and tubulointerstium in a variety of renal diseases in association with scarring and sclerosis of renal parenchyma. Elevated levels of CTGF have also been associated with liver fibrosis, myocardial infarction, and pulmonary fibrosis. For example, in patients with idiopathic pulmonary fibrosis (IPF), CTGF is strongly upregulated in biopsies and bronchoalveolar lavage fluid cells. (Ujike et al. (2000) Biochem Biophys Res Commun 277:448-454; Abou-Shady et al. (2000) Liver 20:296-304; Williams et al. (2000) J Hepatol 32:754-761; Ohnishi et al. (1998) J Mol Cell Cardiol 30:2411-22; Lasky et al. (1998) Am J Physiol 275; L365-371; Pan et al. (2001) Eur J17:1220-1227; and Allen et al. (1999) Am J Respir Cell Mol Biol 21:693-700.) Thus, CTGF represents a valid therapeutic target in disorders, such as those described above.

The association of CTGF with various aspects of these disorders has been established; and methods for treating disorders through modulation of CTGF have been described.

(See, e.g., Grotendorst and Bradham, U.S. Pat. No. 5,783, 187; International Publication No. WO 00/13706; and International Publication No. WO 03/099773.) Modulation of growth factors, cytokines, and cell surface receptors can be accomplished using monoclonal antibodies, and several therapeutic monoclonal antibodies have been approved or are underdevelopment. (See, e.g., Infliximab (Remicade; Maini et al. (1998) Arthritis Rheum 41:1552-1563; Targan et al. (1997) N Engl J Med 337:1029-1035); Basiliximab (Simulect) and Daclizumab (Zenapax) (Bumgardner et al. (2001) Transplantation 72:839-845; Kovarik et al. (1999) Transplantation 68:1288-1294); and Trastuzumab (Herceptin; Baselga (2001) Ann Oncol 12 Suppl 1:S49-55.))

Antibodies have been generated against CTGF, and have proven efficacious in vivo at, e.g., inhibiting angiogenesis. (See, e.g., Grotendorst and Bradham, U.S. Pat. No. 5,408, 040; International Publication No. WO 99/07407; and Shinto et al. (2001) Oncology 61:315-322). Further, the modular nature of CTGF appears to distinguish domains involved in specific biological activities. For example, the N-terminal half of CTGF has been shown to stimulate cell differentiation and ECM production, whereas the C-terminal half stimulates cell proliferation. (See, e.g., International Publication Nos. WO 00/35936 and WO 00/35939; and Brigstock and Harding, U.S. Pat. No. 5,876,70.) This demonstrates that antibodies directed to different regions of the CTGF molecule exhibit different effects with respect to modulating biological activities of CTGF. (See, e.g., International Publication Nos. WO 00/35936 and WO 00/35939). Currently, no clear distinction has been made between anti-CTGF antibodies that produce a desired effect, and those which either produce multiple effects or are non-neutralizing. (See, e.g., International Publication No. WO 99/33878.)

There is clearly a need in the art for agents that effectively neutralize the activity of CTGF in disease. Antibodies, particularly monoclonal antibodies, provide the specificity and pharmacokinetic profiles appropriate for a therapeutic agent, and neutralizing antibodies targeted to specific activities of CTGF would fulfill a need in the art and would find use in therapeutic treatment of CTGF-associated disorders including pulmonary disorders such as idiopathic pulmonary fibrosis (IPF), etc.; renal disorders such as diabetic nephropathy, glomerulosclerosis, etc.; and ocular disorders such as retinopathy, macular degeneration, etc.

SUMMARY OF THE INVENTION

The present invention provides antibodies, particularly monoclonal antibodies, and portions thereof that specifically bind to a region on the N-terminal fragment of a CTGF polypeptide.

In one aspect, an antibody of the invention specifically binds to a region on human CTGF (SEQ ID NO:2) as set forth from about amino acid 103 to amino acid 164 (SEQ ID NO:21), more specifically from about amino acid 135 to about amino acid 157 (SEQ ID NO:22); and even more specifically from about amino acid 142 to about amino acid 154 (SEQ ID NO:25); or an orthologous region on CTGF derived from another species. In particular embodiments, the antibody has the same specificity as an antibody produced by the cell line identified by ATCC Accession No PTA-6006. (Deposited with the ATCC on 20 May 2004.) In specific embodiments, the antibody is substantially identical to mAb1, as described infra. More preferably, the antibody is substantially similar to CLN1, as described infra. In yet another embodiment, an antibody of the invention competitively binds with any of the foregoing antibodies to a CTGF polypeptide.

In one embodiment, the present invention provides a monoclonal antibody or portion thereof comprising at least one member of the group consisting of an immunoglobulin heavy chain sequence comprising SEQ ID NO:14, an immunoglobulin heavy chain sequence comprising the variable domain of SEQ ID NO:14, an immunoglobulin light chain sequence comprising SEQ ID NO:20, an immunoglobulin light chain sequence comprising the variable domain of SEQ ID NO:20, or conservative variants thereof. In a specific embodiment, the antibody comprises the immunoglobulin heavy chain variable domain from amino acid residue 1 through amino acid residue 167 of SEQ ID NO:14. In another specific embodiment, the antibody comprises the immunoglobulin light chain variable domain from amino acid residue 1 through amino acid residue 136 of SEQ ID NO:20. In a particular embodiment, the antibody comprises the immunoglobulin heavy chain sequence of SEQ ID NO:14 and the immunoglobulin light chain sequence of SEQ ID NO:20. Within this embodiment, the present invention specifically provides the antibody of CLN1 or a portion thereof comprising at least the antigen binding region residues of CLN1.

In certain aspects, the antibody of the invention is a polyclonal antibody. In other aspects, the antibody is a monoclonal antibody. In certain embodiments, the antibody is a humanized monoclonal antibody; more preferably a human monoclonal antibody, Any of the aforementioned antibodies may additionally contain various amounts of glycosylation, incorporated by the cell producing the antibody or applied and/or modified synthetically; or the antibody may be free of glycosylation. The antibody may be optionally pegylated and/or similarly modified to increase plasma half-life, etc. In various embodiments, the invention provides fragments of the antibody, particularly wherein the fragment is a Fab, $F(ab)_2$, or Fv fragment.

In certain aspects, the antibody or portion thereof is produced by a cloned cell line. The cell line may be derived from any animal model used for monoclonal antibody production including, but not limited to, mice, goat, chicken, etc. In particular, the cell line may be derived from mice. The mice may be standard mice used for antibody production, e.g., BALB/C, or a modified, e.g., transgenic, mouse strain optimized or developed for production of specific isotype, idiotype, or species-specific monoclonal antibodies. In one embodiment, the cell line is a hybridoma cell line that produces and secretes mAb1. In other embodiments, the cell line produces and secretes an antibody or portion thereof that has a property substantially equivalent to mAb1. In still other embodiments, the cell line produces and secretes an antibody or portion thereof that has a property substantially equivalent to CLN1. In a particular embodiment, the invention provides a cell line identified by ATCC Accession No. PTA-6006. (Deposited 20 May 2004.)

In another aspect, the antibody or portion thereof is derived from a non-human transgenic animal, particularly a non-human transgenic mammal, capable of producing a human antibody. The animal may be of any species including, but not limited to, mouse, chicken, cow, goat, etc. In particular, the animal may be mouse. Such antibodies may be obtainable by immunizing a non-human transgenic mammal with a fragment of human CTGF, e.g., SEQ ID NO:21, or, more specifically, SEQ ID NO:22, or to an orthologous region on CTGF derived from a non-human species. In certain embodiments, the antibodies are obtained by immunizing the non-human transgenic mammal with a fragment of CTGF selected from the group consisting of SEQ ID NOs:23 thru 26 or an orthologous region on CTGF derived from a non-human species. In specific embodiments, the antibodies are obtained by immunizing a transgenic mouse with any of the aforementioned CTGF fragments. In other embodiments, the antibodies are obtained by immunizing a transgenic mouse with functional equivalents of any of the aforementioned CTGF fragments.

By "specifically binds to a region on CTGF", it is meant that the antibodies have binding specificity for a particular region on CTGF, which may be defined by a linear amino acid sequence, or by a tertiary, i.e., three-dimensional, conformation on part of the CTGF polypeptide. Binding specificity means that the antibodies affinity for the portion of CTGF is substantially greater than their affinity for other related polypeptides. By "substantially greater affinity" we mean that there is a measurable increase in the affinity for the portion of CTGF as compared with the affinity for other related polypeptides. Preferably, the affinity is at least 1.5-fold, 2-fold, 5-fold 10-fold, 100-fold, $10^3$-fold, $10^4$-fold, $10^5$-fold, $10^6$-fold or greater for the particular portion of CTGF than for other proteins. Preferably, the binding specificity is determined by affinity chromatography, immunoprecipitation by an in vitro binding assay, such as radioimmunoassay (RIA) or enzyme-linked immunoabsorbent assay (ELISA), or by fluorescence-activated cell sorting (FACS) analysis. More preferably, the binding specificity is obtained by RIA or affinity chromatography, as described infra.

In preferred embodiments of the invention, the antibodies have an affinity that is equal to or greater than that of in mAb1, described infra, as determined, for example, by the Scatchard analysis of Munson and Pollard (1980, Anal Biochem 107: 220), Antibody affinity is defined as the strength of the total noncovalent interactions between a single antigen-binding site on an antibody and a single epitope on an antigen. Affinity is calculated by measuring the association constant ($K_a$), such that $$\text{Affinity} = K_a = \frac{[Ab \cdot Ag]}{[Ab][Ag]} = \frac{1}{K_d}$$

where [Ab] is the concentration of free antigen binding site on the antibody. [Ag] is the concentration of free antigen, [Ab·Ag] is the concentration of antigen binding site on the antibody occupied by antigen, and $K_d$ is the dissociation constant of the antibody-antigen complex. Preferably, antibodies of the invention have an affinity for CTGF that is greater than Kd=$10^{-8}$, preferably greater than $10^{-9}$, preferably greater than $10^{-10}$, particularly for therapeutic use. Advantageously, an antibody according to the invention has an affinity similar to or greater than that of mAb1 (that is, a Kd≤$10^{-9}$). However, antibodies sharing epitope binding with mAb1, but having lower affinity (i.e., higher Kd) than mAb1, are also embodied within the present invention and are potentially useful in various assays and diagnostic applications as described herein. Such antibodies may additionally be useful in therapeutic applications, especially if they have a high avidity for antigen, as described below.

Antibodies according to the invention may be monovalent, bivalent or they may be multi-valent. In certain embodiments of the invention, it is preferred that the antibodies of the invention are bivalent or multivalent. Any of the antibodies of the invention may be manipulated to improve avidity, e.g., by combining epitope-binding sites into a single antibody construct, e.g., a tribody, etc. Antibodies according to the invention may be single chain antibodies.

It may be useful in some circumstances for antibodies of the invention to show suitable affinity for CTGF from other species, for example, for treatment and prevention of disorders in those species. For example, an antibody of the invention that shows a suitable $K_d$ for canine CTGF could be used to treat a CTGF-associated disorder in dogs, Antibodies of the invention that show cross-species affinity, such as mAb1, are also useful as research tools, to study CTGF-associated disorders in various animal models. In another aspect, the antibody or portion thereof is encoded by genetic material originally derived from a human. The antibody may be generated by cells in culture, e.g., using phage display techniques, or may be produced within an animal, e.g., a non-human transgenic animal containing immunoglobulin genes derived from a human.

Additionally, the invention provides recombinant constructs comprising portions of any of the antibodies of the invention, as described above, and a protein derived from another source. Specifically contemplated are embodiments encompassing chimeric antibodies comprising a variable region derived from a monoclonal antibody that specifically binds to a region on an N-terminal fragment of CTGF and a constant region derived from another source. The variable region can be derived from any antibody defined by the invention, and specifically encompasses antibodies that bind to a region on human CTGF from about amino acid 97 to about amino acid 180 of SEQ ID NO:2, or, more specifically, from about amino acid 103 to about amino acid 164 of SEQ ID NO:2, or, more specifically, from about amino acid 134 to about amino acid 158 of SEQ ID NO:2, or, even more specifically, from about amino acid 143 to about amino acid 154 of SEQ ID NO:2, or to an orthologous region on CTGF derived from another species. The constant region can be derived from any source. In some embodiments, the constant region is derived from a constant region of a human immunoglobulin.

The present invention also provides any of the antibodies described above wherein the antibody additionally comprises a labeling agent capable of providing a detectable signal by itself or together with other substances. Such labeling agents can be selected from, but are not limited to, the group consisting of an enzyme, fluorescent substance, chemiluminescent substance, biotin, avidin, and radioisotope. The present invention also provides any of the antibodies described above wherein the antibody additionally comprises a cytotoxic agent or enzyme.

In other embodiments, the antibodies of the invention, as described above, additionally neutralize at least one activity associated with CTGF. Such activities associated with CTGF include, but are not limited to, stimulation of cell migration, production of extracellular matrix by a cell in vivo or ex vivo, and/or reduction in fibrosis in a subject. In particular embodiments, the biological activity is selected from the group consisting of cell growth, differentiation of fibroblasts and/or endothelial cells, and induction of expression of proteins involved in extracellular matrix formation and remodeling including, e.g., collagens including, but not limited to, types I, II, III, and IV; and fibronectin.

In certain embodiments, the antibodies specifically inhibit cell migration in ex vivo assays. Preferably, the antibodies inhibit CTGF-stimulated chemotactic migration of smooth muscle cells in a Boyden chamber assay. For example, in a cell migration assay described infra, antibodies of the invention repeatedly and reproducibly inhibit CTGF-induced migration. In various embodiments, the antibodies specifically reduce fibrosis in animal models. Preferably, the antibodies inhibit development of fibrosis in animal models of lung and kidney fibrosis. For example, the antibodies attenuate bleomycin-induced lung fibrosis in mice by 60-70%, as determined by inhibition of pulmonary hydroxyproline (collagen) accumulation and/or histological examination of tissue preparations, described infra. Further, the antibodies reduce the accumulation of collagen in a rat remnant kidney (i.e., ⅚ nephrectomy) model, and in mice following unilateral ureter obstruction (UUO), as described infra.

In other embodiments, antibodies of the invention modulate the interaction between a CTGF polypeptide and a cell receptor, and/or between a CTGF polypeptide and a secreted or membrane-associated cofactor, thereby neutralizing a biological activity of CTGF. The cofactor may be any protein, carbohydrate, and/or lipid; in particular embodiments, the cofactor is a member of the TGF-β family of growth factors, e.g., TGF-β, BMP-4, etc.

In another aspect, the antibody reduces fibrosis in a subject. In various embodiments, the subject is a tissue or organ. In other embodiments, the subject is an animal, preferably a mammal, most preferably a human. When the subject is a tissue, the invention specifically contemplates both endogenous tissues and ex vivo tissues, e.g., transplant tissues, tissues grown in culture, etc. In various embodiments, the tissue is selected from the group consisting of epithelial, endothelial, and connective tissue. When the subject is an organ, the invention specifically contemplates organs selected from the group consisting of kidney, lung, liver, eye, heart, and skin. In preferred embodiments, the subject is an animal, particularly, an animal of mammalian species including rat, rabbit, bovine, ovine, porcine, murine, equine, and primate species. In a most preferred embodiment, the subject is human.

In specific embodiments, the antibody is used to treat or prevent a CTGF-associated disorder in a subject having or at risk for having a CTGF-associated disorder. Such disorders include, but are not limited to, various cancers including acute lymphoblastic leukemia, dermatofibromas, breast cancer, breast carcinoma, glioma and glioblastoma, rhabdomyosarcoma and fibrosarcoma, desmoplasia, angiolipoma, angioleiomyoma, desmoplastic cancers, and prostate, ovarian, colorectal, pancreatic, gastrointestinal, and liver cancer and other tumor growth and metastases. CTGF-associated disorders also include various fibrotic disorders including, but not limited to, idiopathic pulmonary fibrosis, kidney fibrosis, glomerulosclerosis, ocular fibrosis, osteoarthritis, scleroderma, cardiac fibrosis, and liver fibrosis. Fibrosis can occur in any organ or tissue including an organ selected from, but not limited to, kidney, lung, liver, heart, and skin; or a tissue selected from, but not limited to, epithelial, endothelial, and connective tissue. In other embodiments, the CTGF-associated disorder may be caused by any initiating factor including, but not limited to, exposure to chemicals or biological agents, inflammatory response, autoimmune reaction, trauma, surgical procedures, etc. CTGF-associated disorders also include, but are not limited to, disorders clue to hyperglycemia and hypertension. Such disorders may occur, e.g., due to diabetes, obesity, etc, and include diabetic nephropathy, retinopathy, and cardiovascular disease.

Therefore, in various embodiments, the invention provides antibodies that can be used to treat or prevent CTGF-associated disorders in a subject. The present invention also provides the use of such antibodies in the manufacture of a medicament for the treatment of CTGF-associated disorders.

In another aspect, the invention provides a method of neutralizing an activity associated with CTGF comprising contacting an antibody of the invention and a CTGF polypeptide, thereby neutralizing a biological activity of CTGF, such as those described above. The biological activity can be any activity of CTGF including, but not limited to, stimulation of cell migration and production of extracellular matrix. In various embodiments, the neutralizing occurs in vitro. In other embodiments, the neutralizing occurs in a subject in viva.

In yet another aspect, the invention provides methods of using an antibody as described above to treat a CTGF-associated disorder in a patient in need, the method comprising administering the antibody or a pharmaceutical formulation thereof to the patient, thereby treating the disorder. The subject can be a patient diagnosed with or suspected of having a CTGF-associated disorder, including, e.g., a disorder resulting in excess production of extracellular matrix. In particular aspects, CTGF-associated disorder is selected from a cancer or fibrotic disorder. Cancers include, but are not limited to, acute lymphoblastic leukemia, dermatofibromas, breast cancer, breast carcinoma, glioma and glioblastoma, rhabdomyosarcoma and fibrosarcoma, desmoplasia, angiolipoma, angioleiomyoma, desmoplastic cancers, and prostate ovarian, colorectal, pancreatic, gastrointestinal, and liver cancer, and fibrotic disorders include, but are not limited to, idiopathic pulmonary fibrosis, kidney fibrosis, glomerulosclerosis, ocular fibrosis, macular degeneration, osteoarthritis, scleroderma, chronic heart failure, cardiac fibrosis, and liver fibrosis. In other embodiments, the CTGF-associated disorder may be caused by any initiating factor including, but not limited to, exposure to chemicals or biological agents, inflammatory response, autoimmune reaction, trauma, surgical procedures, etc. CTGF-associated disorders also include, but are not limited to, disorders due to hyperglycemia and hypertension. Such disorders may occur, e.g., due to diabetes, obesity, etc., and include diabetic nephropathy, retinopathy, and cardiovascular disease.

In another aspect, the present invention provides a composition comprising an antibody as described above and at least one other component. Components may include any compound, molecule, or agent, including, e.g., proteins, nucleic acids, carbohydrates, lipids, etc. Additionally, components may include various solvents, salts, and other carriers and/or excipients. In some embodiments, the composition is a pharmaceutical composition comprising an antibody as described above and at least one additional component selected from a solvent, a stabilizer, or an excipient. In a particular embodiment, the pharmaceutical composition comprises an antibody in admixture with a pharmaceutically acceptable carrier. The pharmaceutical composition may additionally contain a second therapeutic agent, e.g., an angiotensin convening enzyme (ACE) inhibitor, an advanced glycation endproduct cleavage or inhibitory agent, etc. The invention additionally provides medicaments comprising an antibody as defined above for treating a subject having a CTGF-associated disorder. Such disorders include, but are not limited to, various cancers and fibrotic disorders; disorders resulting from conditions such as myocardial infarction, arthritis, and inflammation; and disorders due to diabetes, obesity, and the like, which may include diabetic nephropathy, retinopathy, and cardiovascular disease.

In another embodiment, the invention provides a polypeptide sequence selected from the group consisting of SEQ ID NO:14, amino acid 1 through amino acid 167 of SEQ ID NO:14, SEQ ID NO:20, and amino acid 1 through amino acid 136 of SEQ ID NO:20. The invention also encompasses conservative variants of the polypeptides. In another embodiment, the invention provides specific fragments of human CTGF selected from the group consisting of SEQ ID NOs:21 through 26, and orthologous CTGF fragments obtained from a non-human species.

The polypeptides referred to above may be "altered" polypeptides, as defined infra.

In another embodiment, the invention provides a polynucleotide sequence encoding an antibody of the invention or a portion thereof. In particular embodiments, the polynucleotide sequence is selected from the group consisting of a polynucleotide sequence encoding SEQ ID NO:14, a polynucleotide sequence encoding from amino acid 1 through amino acid 167 of SEQ ID NO:14, the polynucleotide sequence of SEQ ID NO:13, and a polynucleotide comprising nucleotide 1 through nucleotide 501 of SEQ ID NO:13. In other embodiments, the polynucleotide sequence is selected from the group consisting of a polynucleotide sequence encoding SEQ ID NO:20, a polynucleotide sequence encoding from amino acid 1 through amino acid 136 of SEQ ID NO:20, the polynucleotide of SEQ ID NO:19, and a polynucleotide comprising nucleotide 1 through nucleotide 408 of SEQ ID NO:19.

The polynucleotides referred to above may be "altered" polynucleotides, as defined infra.

The invention additionally provides recombinant polynucleotides comprising any of the polynucleotide sequences described above operably linked to a vector sequence that contains replication and transcriptional control sequences. In one aspect, the recombinant polynucleotide encodes the amino acid sequence of SEQ ID NO:14 or the variable domain therein. In another aspect, the recombinant polynucleotide comprises SEQ NO:13. In yet another aspect, the recombinant polynucleotide encodes the amino acid sequence of SEQ ID NO:20 or the variable domain therein. In still another aspect, the recombinant polynucleotide comprises SEQ ID NO:19.

The invention also provides host cells transfected with at least one of the recombinant polynucleotides described above. Host cells include any prokaryotic and eukaryotic host cell, including, e.g., cloned cell lines maintained by culture methods known to those of skill in the art. Host cells also include transgenic plants and animals derived from transformed cells, e.g., stem cells. In one embodiment, the host cell comprises a cell co-transfected with a polynucleotide encoding SEQ ID NO:14 and a polynucleotide encoding SEQ ID NO:20, and which produces a functional antibody with characteristics substantially the same as mAb1. In particular embodiments, the antibody is CLN1. In another particular embodiment, the host cell is identified by ATCC Accession No. PTA-6006. (Deposited: 20 May 2004.)

These and other embodiments of the subject invention will readily occur to those of skill in the art in light of the disclosure herein, and all such embodiments are specifically contemplated.

BRIEF DESCRIPTION OF THE DRAWINGS

FIGS. 1A and 1B show the structure and sequence conservation of Connective Tissue Growth Factor. FIG. 1A shows the modular domain structure of CTGF, which includes conserved motifs for insulin-like growth factor binding protein (IGF-BP) and Von Willebrand's factor (VWC) in the N-terminal fragment, and thrombospondin (TSP1) and the cysteine-knot motif (CT) in the C-terminal fragment. FIG. 1B shows a multiple sequence alignment between N-terminal fragments of human (hCTGF; SEQ ID NO:27), bovine (bCTGF; SEQ ID NO:29), porcine (pCTGF; SEQ ID NO:30), rat (rCTGF; SEQ ID NO:31), and murine (FISP 12; SEQ ID NO:32) CTGF orthologs. The alignment was created using the CLUSTAL W program (v. 1.74; Thompson et al. (1994) Nucleic Acids Res 22:46734680) using default parameters. In the figure, an asterisk (*) indicates complete conservation of the amino acid residue among the species represented.

FIG. 3A shows Fab antibody fragment ($M_r$ 45 kD) obtained following papain digestion of the corresponding IgG antibody mAb1 and subsequent protein A-Sepharose affinity chromatography (Lane 2), as demonstrated by SDS-PAGE, FIG. 3B shows binding of a Fab fragment and corresponding IgG to CTGF over increasing concentration of chaotropic agent (thiocyanate).

FIGS. 5A, 5B, and 5C show the therapeutic benefits of an antibody of the invention in a model of interstitial fibrosis in the lung. FIG. 5A shows the effect of antibody treatment on bleomycin-induced increase in hydroxyproline content of mouse lungs. The number of animals in each group is shown in parentheses below each bar and treatment groups are indicated along the x-axis. SA: Saline; BL: Bleomycin; AbsJ pool of 3 monoclonal antibodies of the invention; mAb1, an exemplary antibody of the invention. Values are expressed as mean±SE. FIGS. 5B and 5C show hematoxylin- and eosin stained paraffin sections of pulmonary proximal acini from mice exposed to bleomycin by intratracheal injection and subsequently treated with saline or antibodies of the invention, respectively. In FIG. 5B, the thin interalveolar septa acinus have an abnormal appearance, and inflammatory cells and fibrosis are present. In FIG. 5C, the parenchyma is largely normal and there is only moderate thickening of interalveolar septa.

FIG. 6A shows the reduction in fibrosis due to unilateral ureter obstruction (UUO) following treatment with an antibody of the invention, mAb1, or an antibody directed to the C-terminus of CTGF, mAb3. The extent of fibrosis is expressed as the ratio of hydroxyproline to proline in the obstructed kidney compared with the contralateral unobstructed kidney (mean±SE). FIGS. 6B and 6C show trichome-stained paraffin sections of obstructed kidneys receiving saline or antibody therapy, respectively.

FIGS. 7A and 7B show photomicrographs of trichrome-stained remnant kidney tissue after receiving saline or antibody therapy, respectively.

FIGS. 8A, 8B, 8C, 8D, 8E, 8F, and 8G show the induction of localized subcutaneous granulomas in newborn mice. On the left, FIGS. 8A and 8B show the formation of granuloma at the site of subcutaneous injection of TGFβ alone or TGFβ and CTGF, respectively. On the right, FIGS. 8C through 8G show a histological panel representing the scoring system (from 0 [normal] to 4 [fibrotic]) used to evaluate therapeutic benefit of antibody.

FIG. 11A shows the alignment of heavy chain PCR fragments used to determine the mAb1 heavy chain coding sequence (CDS). FIG. 11B shows the alignment of light chain PCR fragments used to determine the mAb1 light chain coding sequence (CDS).

FIG. 12A shows the degree of binding between TGFβ and either CTGF, a fragment of CTGF encoded by exon 3 (Exon 3), or a fragment of CTGF encoded by exon 5 (Exon 5) in the presence or absence of anti-CTGF antibody. FIG. 12B shows the degree to which anti-CTGF antibodies inhibit TGFβ and CTGF interaction. In the figure, antibodies include exemplary antibodies of the invention, mAb1 and mAb4, and an antibody that specifically binds to a C-terminal CTGF epitope, mAb3.

DESCRIPTION OF THE INVENTION

Figure 1A:

Before the present compositions and methods are described, it is to be understood that the invention is not limited to the particular methodologies, protocols, cell lines, assays, and reagents described, as these may vary. It is also to be understood that the terminology used herein is intended to describe particular embodiments of the present invention, and is in no way intended to limit the scope of the present invention as set forth in the appended claims.

It must be noted that as used herein and in the appended claims, the singular forms "a," "an," and "the" include plural references unless context clearly dictates otherwise. Thus, for example, a reference to "a fragment" includes a plurality of such fragments, a reference to an "antibody" is a reference to one or more antibodies and to equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications cited herein are incorporated herein by reference in their entirety for the purpose of describing and disclosing the methodologies, reagents, and tools reported in the publications, which might be used in connection with the invention. Nothing herein is to be construed as an admission that the invention is not entitled to antedate such disclosure by virtue of prior invention.

The practice of the present invention will employ, unless otherwise indicated, conventional methods of chemistry, biochemistry, molecular biology, cell biology, genetics, immunology and pharmacology, within the skill of the art. Such techniques are explained fully in the literature. See, German), A. R., ed. (1990) Remington's Pharmaceutical Sciences, 18th ed., Mack Publishing Co.; Colowick, S. et al., eds., Methods In Enzymology, Academic Press, Inc.; Handbook of Experimental Immunology, Vols. I-IV (D. M. Weir and C. C. Blackwell, eds., 1986, Blackwell Scientific Publications); Maniatis, T. et al., eds. (1989) Molecular Cloning: A Laboratory Manual, 2nd edition, Vols. MIL Cold Spring Harbor Laboratory Press; Ausubel, F. M. et al., eds. (1999) Short Protocols in Molecular Biology, 4th edition, John Wiley & Sons; Ream et al., eds. (1998) Molecular Biology Techniques: An Intensive Laboratory Course, Academic Press); PCR (Introduction to Biotechniques Series), 2nd ed. (Newton & Graham eds., 1997, Springer Verlag).

DEFINITIONS

"Connective tissue growth factor" or "CTGF" refers to the amino acid sequences of substantially purified CTGF derived from any species, particularly a mammalian species, including rat, rabbit, bovine, ovine, porcine, murine, equine, and hominid, preferably the human species, and from any source, whether natural, synthetic, semi-synthetic, or recombinant.

The term "N-terminal fragment" of CTGF refers to any polypeptide comprising sequences derived from the amino-terminal portion of a CTGF polypeptide, or to any variants, or fragments thereof. N-terminal fragments can include all, none, or portions of CTGF from the initial methionine residue through the cysteine-free "hinge" region as shown in FIGS. 1A and 1B. Further, N-terminal fragments can include all, none, or portions of the insulin growth factor-binding protein motif and/or the von Willebrand type C domain (SEQ ID NO:21) as shown in FIG. 1B. N-terminal fragments of CTGF can also include all, none, or portions of the cysteine-free region. Further, N-terminal fragments of CTGF can be any fifteen or more contiguous amino acids contained within any preceding N-terminal fragment defined above.

In one aspect, "N-terminal fragment" of CTGF refers to polypeptide sequences derived from the amino-terminal portion of human CTGF. Such fragments can encompass the entire region from amino acid residue 1 to about amino acid residue 198 of SEQ ID NO:2, or from about amino acid 23 to about amino acid 198 of SEQ ID NO:2. The boundary of the N-terminal fragment within the hinge region may be optionally defined by one of several protease cleavage sites defined in SEQ ID NO:2, such as chymotrypsin cleavage sites between residues 179 and 180, between residues 182 and 183, and between residues 188 and 189; plasmin cleavage sites between residues 183 and 184, and between residues 196 and 197; and a bone morphogenetic protein-1 cleavage site between residues 169 and 170. Additionally, N-terminal fragments of human CTGF can include all, none, or portions of the region from amino acid 27 to amino acid 97 of SEQ ID NO:2, amino acid 103 to amino acid 166 of SEQ ID NO:2, or amino acid 167 to amino acid 198 of SEQ ID NO:2. Further. N-terminal fragments of human CTGF can be any fifteen or more contiguous amino acids contained within any preceding N-terminal fragment defined above.

In specific embodiments, the CTGF N-terminal fragments of the present invention comprise sequences selected from the following regions of human CTGF (SEQ ID NO:2) and orthologous fragments thereof derived from a different species, particularly a mammalian species including rat, rabbit, bovine, ovine, porcine, marine, and equine: amino acid residue 23 to amino acid residue 96 (encoded by exon 2); amino acid residue 27 to amino acid residue 97 (IGF-BP motif); amino acid residue 97 to amino acid residue 180 (encoded by exon 3); amino acid residue 103 to amino acid residue 166 (VWC domain); amino acid residue 167 to amino acid residue 198 (cysteine-free hinge); amino acid residue 23 to amino acid residue 180 (encoded by exons 2 and 3): amino acid residue 27 to amino acid residue 166 (IGF-BP and VWC); and amino acid residue 23 to amino acid residue 198. (See FIG. 1B.)

The term "C-terminal fragment" of CTGF refers to any polypeptide comprising sequences derived from the carboxyterminal portion of a CTGF amino acid polypeptide sequence, or to any variants, or fragments thereof. C-terminal fragments of CTGF can include all, none, or portions of the cysteine-free region of CTGF polypeptide (ammo acid 167 to amino acid 198 of SEQ ID NO:2).

The C-terminal fragments can include all, none, or portions of CTGF from the cysteine-free hinge region to the end of the protein. Further, C-terminal fragments can include all, none, or portions of the thrombospondin motif and/or the cysteine-knot motif. Further, C-terminal fragments of CTGF can be any fifteen or more contiguous amino acids contained within any preceding C-terminal fragment defined above.

In some aspects, C-terminal fragments can encompass the entire region from amino acid residue 181 to about amino acid residue 349 of SEQ ID NO:2. The boundary of the C-terminal fragment within the hinge region may be optionally defined by one of several protease cleavage sites defined in SEQ ID NO:2, such as chymotrypsin, plasmin, and bone morphogenetic protein-1 cleavage sites defined above. Additionally, C-terminal fragments comprise sequences selected from the following regions of human CTGF (SEQ ID NO:2) and orthologous fragments thereof derived from a different species, particularly a mammalian species including rat, rabbit, bovine, ovine, porcine, murine, and equine: amino acid 201 to amino acid 242 of SEQ ID NO:2, amino acid 247 to amino acid 349 of SEQ ID NO:2, amino acid 248 to amino acid 349 of SEQ ID NO:2, or amino acid 249 to amino acid 346 of SEQ ID NO:2 Further, C-terminal fragments of human CTGF can be any fifteen or more contiguous amino acids contained within any preceding C-terminal fragment defined above.

The terms "cysteine-free region" or "hinge region" of CTGF refer to any polypeptide derived from about amino acid residue 167 to about amino acid residue 198 of human CTGF (SEQ ID NO:2) and orthologous fragments thereof derived from a different species, particularly a mammalian species including rat, rabbit, bovine, ovine, porcine, murine, and equine.

The terms "amino acid sequence" or "polypeptide" or "polypeptides" as used herein refer to oligopeptide, peptide, polypeptide, or protein sequences, and fragments thereof, and to naturally occurring or synthetic molecules. A polypeptide or amino acid fragment is any portion of a polypeptide that retains at least one structural and/or functional characteristic of the polypeptide. CTGF fragments include any portion of a CTGF polypeptide sequence that retains at least one structural or functional characteristic of CTGF. Where "amino acid sequence" is recited to refer to the polypeptide sequence of a naturally occurring protein molecule, "amino acid sequence" and like terms are not meant to limit the amino acid sequence to the complete native sequence associated with the recited protein molecule.

The term "immunogenicity" relates to the ability of a substance, when introduced into the body, to stimulate the immune response and the production of an antibody. An agent displaying the property of immunogenicity is referred to as being immunogenic. Immunogenic agents can include, but are not limited to, a variety of macromolecules such as, for example, proteins, lipoproteins, polysaccharides, nucleic acids, bacteria and bacterial components, and viruses and viral components. Immunogenic agents often have a molecular weight greater than 10 kDa. Antigenic fragments refer to fragments of CTGF polypeptide, preferably, fragments of about five to fifteen amino acids in length, that retain at least one biological or immunological aspect of CTGF polypeptide activity.

The term "antibody" refers to intact molecules as well as to fragments thereof, such as Fab, F(ab')2, and Fv fragments, which are capable of binding the epitopic determinant, and include polyclonal and monoclonal antibodies. Antibodies that bind CTGF or fragments of CTGF can be prepared using intact polypeptides or using fragments containing small peptides of interest as the immunizing antigen. The polypeptide or oligopeptide used to immunize an animal (e.g., a mouse, rat, rabbit, chicken, turkey, goat, etc.) can be derived from the translation of RNA, or synthesized chemically, and can be conjugated to a carrier protein if desired. Commonly used carriers chemically coupled to peptides include, for example, bovine serum albumin, thyroglobulin, and keyhole limpet hemocyanin (KLH).

The term "monoclonal antibody" as used herein refers to a substantially homogeneous population of antibodies, i.e., the individual antibodies comprising the population are identical in specificity and affinity except for possible naturally occurring mutations that may be present in minor amounts. Note that a monoclonal antibody composition may contain more than one monoclonal antibody.

The monoclonal antibodies included within the scope of the invention include hybrid and recombinant antibodies (e.g., "humanized" antibodies) regardless of species of origin or immunoglobulin class or subclass designation, as well as antibody fragments (e.g., Fab, F(ab')$_2$, and Fv), having at least one of the distinct characteristics of the antibodies described herein. Preferred embodiments include antibodies capable of binding to substantially the same epitope as that recognized by monoclonal antibody mAb1 and/or have affinity for that epitope that is greater than or equal to the affinity of mAb1.

The term "monoclonal" indicates the character of the antibody as a substantially homogeneous population of antibodies, and is not to be construed as requiring production of the antibody by any particular method. For example, the monoclonal antibodies of the invention may be made using the hybridoma method first described by Kohler and Milstein (1975, Nature 256:495-497), or may be made by recombinant DNA methods. For example, see Celltech Therapeutics Ltd., European Patent No. EP-0 120 694; Cabilly et al., U.S. Pat. No. 4,816,567; or Mage and Lamoyi (1987; In: *Monoclonal Antibody Production Techniques and Applications*, Marcel Dekker, Inc., New York, pp. 79-97).

The term "neutralizing antibody" as used herein refers to an antibody, preferably a monoclonal antibody, that is capable of substantially inhibiting or eliminating a biological activity of CTGF. Typically, a neutralizing antibody will inhibit binding of CTGF to a cofactor such as TGFβ, to a CTGF-specific receptor associated with a target cell, or to another biological target. In a particular embodiment, a neutralizing antibody will inhibit a biological activity of CTGF to a degree approximately equal to or greater than mAb1. Preferably, a neutralizing antibody will inhibit a biological activity of CTGF to a degree approximately equal to or greater than CLN1.

The phrase "CTGF-associated disorders" as used herein refers to conditions and diseases associated with abnormal or altered expression or activity of CTGF. Abnormal expression of CTGF has been associated with cell proliferative disorders, such as those caused by endothelial cell proliferation; cell migration; tumor-like growths; general tissue scarring; and various diseases characterized by inappropriate deposition of extracellular matrix.

CTGF-associated disorders include, but are not limited to, disorders involving angiogenesis and other processes which play a central role in conditions such as proliferative vitreo-retinopathy; cancer, including acute lymphoblastic leukemia, dermatofibromas, breast cancer, breast carcinoma, glioma and glioblastoma, rhabdomyosarcoma and fibrosarcoma, desmoplasia, angiolipoma, angioleiomyoma, desmoplastic cancers, and prostate, ovarian, colorectal, pancreatic, gastrointestinal, and liver cancer; other tumor growth and metastases; etc.

CTGF-associated disorders also include fibrotic disorders and related conditions, such as excessive scarring resulting from localized or systemic fibrosis, chronic or acute fibrosis of organs such as the kidney, lungs, liver, eyes, heart, skin, etc.; or a tissue selected from, but not limited to, epithelial, endothelial, and connective tissue. Fibrosis can also occur in the eye and joints. Such CTGF-associated disorders include, for example, cardiac fibrosis, including cardiac reactive fibrosis or cardiac remodeling following myocardial infarction or congestive heart failure; pulmonary disorders, including interstitial pulmonary fibrosis, etc.; fibrosis associated with dialysis including peritoneal dialysis, e.g., continuous ambulatory peritoneal dialysis (CAPD); peridural fibrosis; kidney fibrosis; pulmonary fibrosis; interstitial fibrosis; skin fibrosis; and fibrosis resulting from acute or repetitive traumas, including surgery, chemotherapy, radiation treatment, allograft rejection, chronic and acute transplant rejection (e.g., kidney, liver, or other organ); bronchiolitis obliterans, e.g., following lung transplant; and inflammation and infection e.g., due to disease or injury.

Additionally, CTGF-associated disorders include, but are not limited to, sclerotic conditions, including systemic sclerosis, scleroderma, keloids, hypertrophic scarring, and other dermatological diseases and conditions; atherosclerosis, such as conditions involving atherosclerotic plaques and atherosclerosis associated with diabetes, peritoneal dialysis, etc.; arthritis, including rheumatoid arthritis, osteoarthritis, and other joint inflammatory conditions, etc.; interstitial diseases, including interstitial fibrosis; Crohn's disease; inflammatory bowel disease; retinopathies, including, for example, proliferative vitreoretinopathy, non-proliferative diabetic retinopathy, proliferative diabetic retinopathy, and macular degeneration (including age-related and juvenile (Stargardt's) disease, and pigment epithelial detachment); nephropathies, including diabetic nephropathy, IgA-associated nephropathy, nephropathy due to toxicity, lupus kidney disease, etc.; and conditions associated with chemical toxicity tubule destruction.

CTGF-associated disorders also include, but are not limited to, disorders due to hyperglycemia, hypertension, advanced glycation endproduct (AGE) formation, etc. Such disorders may occur, e.g., due to diabetes, obesity, etc., and include diabetic nephropathy, retinopathy, and cardiovascular disease. Further, CTGF-associated disorders may be caused by any initiating factor including, but not limited to, exposure to chemicals or biological agents, inflammatory response, autoimmune reaction, trauma, surgical procedures, etc. In some embodiments, the methods are used to treat a patient predisposed to a CTGF-associated disorder due to a condition including, but not limited to, myocardial infarction, arthritis, and local or systemic inflammation.

The "proliferative" processes and disorders referred to herein include pathological states characterized by the continual multiplication of cells resulting in an overgrowth of a cell population within a tissue. The cell populations are not necessarily transformed, tumorigenic or malignant cells, but can include normal cells as well. For example, CTGF may be involved pathologically by inducing a proliferative lesion in the intimal layer of an arterial wall, resulting in atherosclerosis, or by stimulating neovascularization.

"Cancer" refers to any autonomous growth of tissue, including uncontrolled, abnormal growth of cells, or to any malignant tumor of potentially unlimited growth that expands locally by invasion and systemically by metastasis. Cancer also refers to any abnormal state marked by a cancer.

The term "fibrosis" refers to abnormal processing of fibrous tissue, or fibroid or fibrous degeneration. Fibrosis can result from various injuries or diseases, and can often result from chronic transplant rejection relating to the transplantation of various organs. Fibrosis typically involves the abnormal production, accumulation, or deposition of extracellular matrix components, including overproduction and increased deposition of, for example, collagen and fibronectin. "Fibrosis" is used herein in its broadest sense referring to any excess production or deposition of extracellular matrix proteins. There are numerous examples of fibrosis, including the formation of scar tissue following a heart attack, which impairs the ability of the heart to pump. Diabetes frequently causes damage/scarring in the kidneys, which leads to a progressive loss of kidney function; and in the eyes, which causes loss of vision. After surgery, scar tissue can form between internal organs causing contracture, pain, and in some cases, infertility. Major organs such as the heart, kidney, liver, eye, and skin are prone to chronic scarring, commonly associated with other diseases. Hypertrophic scars (non-malignant tissue bulk) are a common form of fibrosis caused by burns and other trauma. In addition, there are a number of other fibroproliferative disorders, including scleroderma, keloids, and atherosclerosis, which are associated respectively with general tissue scarring, tumor-like growths in the skin, or sustained scarring of blood vessels which impairs blood carrying ability.

The terms "nucleic acid" or "polynucleotide" or "polynucleotides" refer to oligonucleotides, nucleotide sequences, or polynucleotides, or any fragments thereof, and to DNA or RNA of natural or synthetic origin which may be single- or double-stranded and may represent the sense or antisense strand, to peptide nucleic acid (PNA), or to any DNA-like or RNA-like material, natural or synthetic in origin. Polynucleotide fragments are any portion of a polynucleotide sequence that retains at least one structural or functional characteristic of the polynucleotide. Polynucleotide fragments can be of variable length, for example, greater than 60 nucleotides in length, at least 100 nucleotides in length, at least 1000 nucleotides in length, or at least 10,000 nucleotides in length.

"Altered" polynucleotides include those with deletions, insertions, or substitutions of different nucleotides resulting in a polynucleotide that encodes the same or a functionally equivalent polypeptide. Included within this definition are sequences displaying polymorphisms that may or may not be readily detectable using particular oligonucleotide probes or through deletion of improper or unexpected hybridization to alleles, with a locus other than the normal chromosomal locus for the subject polynucleotide sequence.

"Altered" polypeptides may contain deletions, insertions, or substitutions of amino acid residues, which produce a silent change and result in a functionally equivalent polypeptide. Deliberate amino acid substitutions may be made on the basis of similarity in polarity, charge, solubility, hydrophobicity, hydrophilicity, and/or the amphipathic nature of the residues as long as the biological or immunological activity of the encoded polypeptide is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine, glycine and alanine, asparagine and glutamine, serine and threonine, and phenylalanine and tyrosine.

A polypeptide or amino acid "variant" is an amino acid sequence that is altered by one or more amino acids from a particular amino acid sequence. A polypeptide variant may have conservative changes, wherein a substituted amino acid has similar structural or chemical properties to the amino acid replaced, e.g. replacement of leucine with isoleucine. A variant may also have non-conservative changes, in which the substituted amino acid has physical properties different from those of the replaced amino acid, e.g., replacement of a glycine with a tryptophan. Analogous minor variations may also include amino acid deletions or insertions, or both. Preferably, amino acid variants retain certain structural or functional characteristics of a particular polypeptide. Guidance in determining which amino acid residues may be substituted, inserted, or deleted may be found, for example, using computer programs well known in the art, such as LASERGENE software (DNASTAR Inc., Madison, Wis.)

A polynucleotide variant is a variant of a particular polynucleotide sequence that preferably has at least about 80%, more preferably at least about 90%, and most preferably at least about 95% polynucleotide sequence similarity to the particular polynucleotide sequence. It will be appreciated by those skilled in the art that as a result of the degeneracy of the genetic code, a multitude of variant polynucleotide sequences encoding a particular protein, some bearing minimal homology to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard codon triplet genetic code, and all such variations are to be considered as being specifically disclosed.

A "deletion" is a change in an amino acid or nucleotide sequence that results in the absence of one or more amino acid residues or nucleotides.

The terms "insertion" or "addition" refer to a change in a polypeptide or polynucleotide sequence resulting in the addition of one or more amino acid residues or nucleotides, respectively, as compared to the naturally occurring molecule.

The term "functional equivalent" as it is used herein refers to a polypeptide or polynucleotide that possesses at least one functional and/or structural characteristic of a particular polypeptide or polynucleotide. A functional equivalent may contain modifications that enable the performance of a specific function. The term "functional equivalent" is intended to include fragments, mutants, hybrids, variants, analogs, or chemical derivatives of a molecule.

The term "microarray" refers to any arrangement of nucleic acids, amino acids, antibodies, etc., on a substrate. The substrate can be any suitable support, e.g., beads, glass, paper, nitrocellulose, nylon, or any appropriate membrane, etc. A substrate can be any rigid or semi-rigid support including, but not limited to, membranes, filters, wafers, chips, slides, fibers, beads, including magnetic or nonmagnetic beads, gels, tubing, plates, polymers, microparticles, capillaries, etc. The substrate can provide a surface for coating and/or can have a variety of surface forms, such as wells, pins, trenches, channels, and pores, to which the nucleic acids, amino acids, etc., may be bound.

The term "sample" is used herein in its broadest sense. Samples may be derived from any source, for example, from bodily fluids, secretions, tissues, cells, or cells in culture including, but not limited to, saliva, blood, urine, serum, plasma, vitreous, synovial fluid, cerebral spinal fluid, amniotic fluid, and organ tissue (e.g., biopsied tissue); from chromosomes, organelles, or other membranes isolated from a cell; from genomic DNA, cDNA, RNA, mRNA, etc.; and from cleared cells or tissues, or blots or imprints from such cells or tissues. Samples may be derived from any source, such as, for example, a human subject, or a non-human mammalian subject, etc. Also contemplated are samples derived from any animal model of disease. A sample can be in solution or can be, for example, fixed or bound to a substrate. A sample can refer to any material suitable for testing for the presence of CTGF or of fragments of CTGF or suitable for screening for molecules that bind to CTGF or to fragments thereof. Methods for obtaining such samples are within the level of skill in the art.

The term "hybridization" refers to the process by which a nucleic acid sequence binds to a complementary sequence through base pairing. Hybridization conditions can be defined by, for example, the concentrations of salt or formamide in the prehybridization and hybridization solutions, or by the hybridization temperature, and are well known in the art. Hybridization can occur under conditions of various stringency.

In particular, stringency can be increased by reducing the concentration of salt, increasing the concentration of formamide, or raising the hybridization temperature. For example, for purposes of the present invention, hybridization under high stringency conditions might occur in about 50% formamide at about 37° C. to 42° C., and under reduced stringency conditions in about 35% to 25% formamide at about 30° C. to 35° C. In particular, hybridization generally occurs in conditions of highest stringency at 42° C. in 50% formamide, 5×SSPE, 0.3% SDS, and 200 µg/ml sheared and denatured salmon sperm DNA.

The temperature range corresponding to a particular level of stringency can be further narrowed by methods known in the art, for example, by calculating the purine to pyrimidine ratio of the nucleic acid of interest and adjusting the temperature accordingly. To remove nonspecific signals, blots can be sequentially washed, for example, at room temperature or up to and including 60° C. under increasingly stringent conditions of up to 0.1×SSC and 0.5% SDS. Variations on the above ranges and conditions are well known in the art.

Invention

Figure 1A:
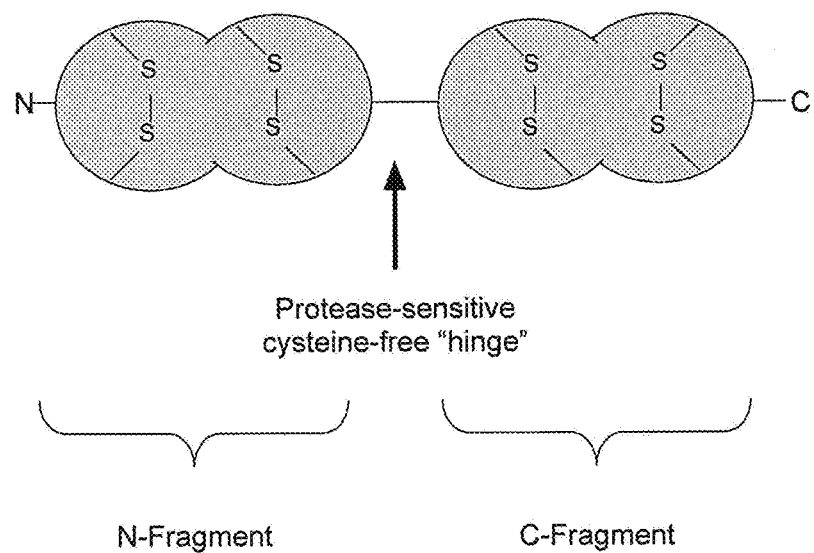

The present invention provides antibodies that specifically bind to Connective Tissue Growth Factor (CTGF). The antibodies are polyclonal or monoclonal antibodies, preferably monoclonal antibodies, and more preferably human monoclonal antibodies. The antibodies are directed toward the N-terminal fragment of CTGF, shown in FIG. 1. More specifically, the antibodies are directed toward a fragment of CTGF extending from about residue 97 to about residue 180 of SEQ ID NO:2. In particular embodiments, the antibodies are directed toward a fragment of CTGF extending from about residue 103 to about residue 164, and more particularly a fragment from about residue 134 to about residue 158 of SEQ ID NO:2. More specifically, the antibodies are directed toward a fragment of CTGF extending from about residue 143 to about residue 154 of SEQ ID NO:2.

In particular embodiments, the antibodies neutralize a biological activity of CTGF. Biological activities of CTGF include cell proliferation, differentiation, gene expression, etc. In particular embodiments, the biological activity is selected from the group consisting of cellular differentiation, e.g., differentiation or transdifferentiation of fibroblasts, myofibroblasts, endothelial cells, etc., from various precursor cells; induction of expression of proteins involved in extracellular matrix formation and remodeling including, e.g., type I collagen, fibronectin, etc.; cooperative induction of signaling cascades associated with various factors including, but not limited to, TGF-β, IGF, VEGF, angiotensin II, endothelin, etc.; and cellular response to various environmental stimuli including, but not limited to, increased glucose (hyperglycemia), increased mechanical stress (hypertension), etc.

Although the invention is not to be limited by the mechanism by which the antibodies neutralize CTGF activity, the antibodies may bind to and prevent CTGF from interacting with specific cell receptors. The receptors may have high binding affinity for CTGF and, by binding to CTGF, stimulate an intracellular signal that leads to proliferation, differentiation, induction of gene expression, and/or change in cellular morphology or function. The particular biological response of a cell to CTGF depends on the cell and the current state of the surrounding milieu. Alternatively, the receptors may have low binding affinity for CTGF and, by binding to CTGF, may, e.g., position CTGF relative to high affinity receptors to facilitate recognition for and response to CTGF. Alternatively, the antibodies may bind CTGF within tissues or organs and facilitate titration or elimination of CTGF from the body.

Alternatively or in conjunction with the mechanisms described above, the antibodies may bind to and prevent CTGF from interacting with secreted or membrane-bound cofactors. Such cofactors specifically include members of the TGFβ superfamily including, e.g., TGFβ-1, -2, and -3; activin-A, -B, -C, and -E; BMP-2, -3, -4, -5, -6, -7, -8a, -8b, -9, -10, -11, and -15; and GDF-3, -5, -6, -7, -9, and -10. For example, CTGF has been shown to bind to TGFβ-1 and BMP-4 and modulate their activity. (Abreu et al. (2002) Nat Cell Biol 4: 599-604.) The present invention provides evidence that the region of CTGF that binds to TGFβ is encoded by exon 3 (FIG. 1B; nucleotide 418 to nucleotide 669 of SEQ ID NO: 1) and antibodies that bind within this region prevent interaction between CTGF and TGFβ. (Example 12, infra.) Further, antibodies that bind within this region of CTGF have been shown to neutralize specific CTGF-associated processes in animal models. For example, antibodies that bind within this region of CTGF have been shown to specifically inhibit cell migration in ex vivo assays, and reduce fibrosis in animal models. Exemplary antibodies of the invention are in mAb1 and CLN1; antibody CLN1 is produced by the cell line defined by ATCC Accession No. PTA-6006, deposited with the American Type Culture Collection (ATCC, 10801 University Boulevard, Manassus Va. 20110-2209) on 20 May 2004. The Chinese Hamster Ovary (CHO) cell line identified as ATCC Accession No. PTA-6006, which produces the human monoclonal antibody CLN-1, was deposited with the ATCC under the provisions of the Budapest Treaty on the International Recognition of the Deposit of Microorganisms for the Purpose of Patent Procedure and the Regulations thereunder (Budapest Treaty). This assures maintenance of viable cultures at ATCC for at least 30 years from the date of deposit, or for the enforceable life of the patent, or for a period of 5 years after the date of the most recent request for furnishing a sample of the deposited material, whichever is longest. The organisms will be made available by ATCC under the terms of the Budapest Treaty and the cell line will be irrevocably and without restriction or condition released to the public upon issuance of a patent. Also, if the culture deposit should die or be lost or destroyed when cultivated under suitable conditions, it will be promptly replaced on notification with a viable specimen of the same culture. Availability of a deposited strain is not to be construed as a license to practice the invention in contravention of the rights granted under the authority of any government in accordance with its patent laws.

Regardless of the mechanism of action, the present invention provides methods of using the antibodies to treat various diseases and disorders associated with CTGF. Diseases and disorders associated with CTGF include, but are not limited to, nephropathies, pulmonary fibroses, retinopathies, scleroderma, liver fibroses, heart failure, arthritis, and atherosclerosis. Additionally, disorders associated with CTGF occur due to various factors including, but not limited to, hyperglycemia, hypertension, diabetes, obesity, etc; and include diabetic nephropathy, retinopathy, cardiovascular disease, and the like. As CTGF is overexpressed in a wide variety of diseases including those listed above, the invention contemplates treating patients having a CTGF-associated disorder with a CTGF antibody to improve or stabilize the pathology, retain or restore organ function, improve the quality of life, and prolong survival.

For example, the antibodies are particularly directed to regions of CTGF involved in biological activities associated with both fibrotic and non-fibrotic aspects of various disorders including, e.g., interstitial pulmonary fibrosis, diabetic nephropathy and retinopathy, macular degeneration, etc. The invention also relates to methods of using the antibodies to treat disorders associated with CTGF including localized and systemic fibrotic disorders, such as those of the lung, liver, heart, skin, and kidney, etc.; and localized scar formation due to, e.g., trauma, surgical procedures, etc.

The antibodies of the invention can also be used in any method that involves binding to CTGF. Such methods include purification of CTGF or fragments of CTGF, e.g., by affinity chromatography; detection of CTGF or fragments of CTGF in a sample, e.g., using ELISA or immunohistochemical techniques; diagnosing a CTGF-associated disorder by using the method of detecting CTGF to measure CTGF levels in a patient sample and comparing the level of CTGF in the sample to a standard.

Antibodies Directed to CTGF

Modulation of the amount and/or activity of secreted cellular factors using, e.g., monoclonal antibodies, has been demonstrated, and several therapeutic antibodies have been approved or are under development. (See, e.g., Abciximab (Reopro; Centocor, Inc, Malvern Pa.), lnfliximab (Remicade; Maini et al. (1998) Arthritis Rheum 41:1552-1563; Targan et al. (1997) N Engl J Med 337:1029-1035); Basiliximab (Simulect) and Daclizumab (Zenapax) (Bumgardner et al. (2001) Transplantation 72:839-845; Kovarik et al. (1999) Transplantation 68:1288-1294); and Trastuzumab (Herceptin; Baselga (2001) Ann Oncol 12 Suppl 1:S49-55.)) Numerous methods of producing antibodies, including production in animals, plants, fungi, and bacteria; synthetic construction; and ex vivo culture; are known and available to those of skill in the art.

The antibodies of the invention may be prepared using any technique that provides for the production of antibody molecules. Techniques for in vivo and in vitro production of either monoclonal or polyclonal antibodies are well known in the art. (See, e.g., Pound (1998) *Immunochemical Protocols*, Humana Press, Totowa N.J.; Harlow and Lane (1988) *Antibodies: A Laboratory Manual*, Cold Spring Harbor Laboratory, New York; Goding (1986) *Monoclonal Antibodies: Principles and Practice,* $2^{nd}$ Edition, Academic Press; Schook (1987) *Monoclonal Antibody Production Techniques and Applications*, Marcel Dekker, Inc.) The production of chimeric antibodies is also well known in the art, as is the production of single-chain antibodies. (See, e.g., Morrison et al. (1984) Proc Natl Acad Sci USA 81:6851-6855; Neuberger et al. (1984) Nature 312:604-608; Takeda et al. (1985) Nature 314:452-454.) Antibodies with related specificity, but of distinct idiotypic composition, may be generated by a variety of available means, for example, by chain shuffling from random combinatorial immunoglobin libraries. (See, e.g., Burton (1991) Proc Natl Acad Sci USA 88:11120-11123.)

Antibodies may also be produced by inducing in vivo production in the lymphocyte population or by screening immunoglobulin libraries or panels of highly specific binding reagents. (See, e.g., Orlandi et al. (1989) Proc Natl Acad Sci USA 86:3833-3837; Winter and Milstein (1991) Nature 349: 293-299.) Antibody fragments that contain specific binding sites for the target polypeptide may also be generated. Such antibody fragments include, but are not limited to, F(ab')$_2$ fragments, which can be produced by pepsin digestion of the antibody molecule, and Fab fragments, which can be generated by reducing the disulfide bridges of the F(ab')$_2$ fragments. Alternatively. Fab expression libraries may be constructed to allow rapid and easy identification of monoclonal Fab fragments with the desired specificity. (See, e.g., Huse et al. (1989) Science 254:1275-1281.)

Monoclonal antibodies of the invention may also be prepared using the hybridoma method (see, e.g., Kohler and Milstein (1975) Nature 256:495-497) or by recombinant DNA methods (see, e.g., Celltech Therapeutics Ltd., European Patent No. EP 0 120 694; Cabilly et al., U.S. Pat. No. 4,816,567; and Mage and Lamoyi (1987) In: *Monoclonal Antibody Production Techniques and Applications*, Marcel Dekker, Inc., New York, pp. 79-97).

In the hybridoma method, a mouse or other appropriate host animal is immunized with CTGF or a fragment thereof by subcutaneous, intraperitoneal, or intramuscular routes to elicit lymphocytes that produce or are capable of producing antibodies that will specifically bind to the polypeptide used for immunization. Alternatively, the host animal may be a transgenic mammal having transgenes encoding human immunoglobulin genes and having inactivated endogenous immunoglobulin loci. The transgenic mammal responds to immunogens by producing human antibodies. (See, e.g., Lonberg et al., WO 93/12227 (1993), U.S. Pat. No. 5,877,397, and Nature 148:1547-1553 (1994); and Kucherlapati et al. (1991) WO 91/1074.) Alternatively, lymphocytes may be immunized in vitro and then fused with myeloma cells using a suitable fusing agent, such as polyethylene glycol, to form a hybridoma cell. (See, e.g., Goding (1986) *Monoclonal Antibodies; Principles and Practice, 2$^{nd}$* Edition, Academic Press, pp. 59-103.) Alternatively, human somatic cells capable of producing antibody, specifically B lymphocytes, are suitable for fusion with myeloma cell lines. While B lymphocytes from biopsied spleens, tonsils or lymph nodes of an individual may be used, the more easily accessible peripheral blood B lymphocytes are preferred. In addition, human B cells may be directly immortalized by the Epstein-Barr virus. (See, e.g., Cole et al. (1995) *Monoclonal Antibodies and Cancer Therapy*, Alan R. Liss, Inc., pp. 77-96.)

Preferred myeloma cell lines for use in hybridoma-producing fusion procedures are those that fuse efficiently, support stable high-level expression of antibody by the selected antibody-producing cell, have enzyme deficiencies that render them incapable of growing in certain selective media which support the growth of the desired hybridomas, and that do not themselves produce antibody. Examples of myeloma cell lines that may be used for the production of hybridomas in the present invention include P3X63Ag8, P3X63Ag8-653, NS1/1.Ag4.1, Sp210-Ag14, FO, NSC/U, MPC-11, MPC11-X45-GTG 1.7, S194/5XX0Bul, all derived from mice; R210.RCY3, Y3-Ag 1.2.3, IR983F and 4B210, all derived from rats; and U-266, GM1500-GRG2, LICR-LON-HMy2, UC729-6, all derived from humans. (See, e.g., Coding (1986) *Monoclonal Antibodies: Principles and Practice. 2$^{nd}$* Edition, Academic Press, pp. 65-66; and Campbell (1984) In *Monoclonal Antibody Technology Laboratory Techniques in Biochemistry and Molecular Biology*. Vol. 13 (Burden and Von Knippenberg, eds.) Amsterdam, Elseview, pp. 75-83.)

The hybridoma cells are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include a substance such as hypoxanthine, aminopterin, and thymidine (HAT medium) that prevents the growth of HGPRT-deficient cells.

Culture medium in which hybridoma cells are growing is assayed for production of monoclonal antibodies directed against CTGF or fragments of CTGF. Preferably, the binding specificity is determined by affinity chromatography, immunoprecipitation or by an in vitro binding assay, such as radioimmunoassay (RIA) or enzyme-linked immunoabsorbent assay (ELISA), or by fluorescence-activated cell sorting (FACS) analysis. The monoclonal antibodies of the invention are those that bind to CTGF, and additionally those that neutralize a CTGF biological activity, as exemplified infra.

The antibodies produced, e.g., as described supra, are optionally screened to detect antibodies that bind to substantially the N-terminal fragment of CTGF. In one embodiment, the antibodies are directed toward a fragment of CTGF extending from about residue 24 to about residue 180 of SEQ ID NO:1. In another embodiment, the antibodies are directed toward a fragment of CTGF extending from about residue 96 to about residue 180 of SEQ ID NO:1. In a particular embodiment, the screen detects antibodies that bind to substantially the same epitope recognized by antibody mAb1 as determined, e.g., by competition assays of the sort described infra. In another particular embodiment, the screen detects antibodies that bind to substantially the same epitope recognized by antibody CLN1 as determined, e.g., by competition assays of the sort described infra. It should be kept in mind that "same epitope" does not mean the exact amino acid or carbohydrate to which the benchmark antibody binds, as may be determined, for example, by epitope mapping using alanine scanned variants of CTGF. "Same epitope" means the CTGF domain that is blocked by the binding to CTGF of the native benchmark antibody in intact form. Of course, "same epitope" includes the CTGF domain residues or carbohydrate that structurally interacts or binds to the benchmark complementarity determining regions (CDRs) of mAb1 or CLN1.

In a preferred embodiment of the invention, the monoclonal antibody will have an affinity that is equal to or greater than that of mAb1, as determined, for example, by the Scatchard analysis of Munson and Pollard (1980, Anal Biochem 107:220).

After hybridoma cells are identified that produce neutralizing antibodies of the desired specificity and affinity, the clones typically are subcloned by limiting dilution procedures and grown by standard methods. (Goding (1986) *Monoclonal Antibodies: Principles and Practice, 2$^{nd}$* Edition, Academic Press, pp. 59-104.) Suitable culture media for this purpose include, for example, Dulbecco's Modified Eagle's Medium or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies of the invention is readily isolated and sequenced using conventional procedures, e.g., by using oligonucleotide probes that are capable of binding specifically to genes encoding the antibody heavy and light chains. Once isolated, the DNA can be ligated into expression or cloning vectors, which are then transfected into host cells such as simian COS cells, Chinese Hamster ovary (CHO) cells, or myeloma cells that do not otherwise produce immunoglobulin protein. The cells so transformed are cultured under conditions suitable for the synthesis of monoclonal antibodies in the recombinant host cell culture. An exemplary cell line is defined by ATCC Accession No. PTA-6006, deposited with the ATCC on 20 May 2004.

The DNA optionally is modified in order to change the character of the encoded immunoglobulin. Variants of immunoglobulins are well known. For example, chimeric antibodies are made by substituting the coding sequence for heavy and light chain constant domains from one species, e.g., mouse, with the homologous sequences from another species, e.g., human. (See, e.g., Boss et al., International Publication No. WO 84/03712; Cabilly et al., U.S. Pat. No. 4,816,567; or Morrison et al. (1984) Proc Nat Acad Sci 81:6851.) In a particular embodiment, humanized forms of murine antibodies can be made by substituting the complementarity determining regions (CDRs), variable domains, of a mouse antibody into a framework domain, i.e., constant region, of a human antibody. (See, e.g., International Publication No. WO 92/22653.) In some embodiments, selected murine framework residues also are substituted into the human recipient immunoglobulin. In addition, the Fc domain chosen can be any of IgA, IgD, IgE, IgG-1, IgG-2, IgG-3, IgG-4, or IgM. The Fc domain optionally is capable of effector functions such as complement binding.

Anti-CTGF antibodies of the present invention may also be fused to moieties that provide additional capabilities, such as detection or cytotoxic effects. Fusions of the immunoglobulins of this invention and cytotoxic moieties are made, for example, by ligating to the immunoglobulin coding sequence all or part of the coding sequence for a cytotoxic non-immunoglobulin polypeptide. Such non-immuoglobulin polypeptides include polypeptide toxins such as ricin, diphtheria toxin, or *Pseudomonas* exotoxin. The conjugates can also be prepared by in vitro methods. For example, immunotoxins may be constructed using a disulfide exchange reaction or by forming a thioether bond between the immunoglobulin and the toxin polypeptide. Examples of suitable reagents for this purpose include iminothiolate and methyl-4-mercaptobutyrimidate. Typically such non-immunoglobulin fusion polypeptides are substituted for the constant domains of an antibody of the invention. Alternatively, they are substituted for the variable domains of one antigen-combining site of an antibody of the invention.

Substitution of the Fv CDRs of an antibody having specificity for a non-CTGF antigen will create a chimeric antibody comprising one antigen-combining site having specificity for CTGF and another antigen-combining site having specificity for a different antigen. In such embodiments, the light chain is deleted and the Fv of the heavy chain is substituted with the desired polypeptide. These antibodies are termed bivalent or polyvalent, depending upon the number of immunoglobulin "arms" possessed by the Fc domain employed: for example, IgGs will be bivalent and IgMs will be polyvalent. Aside from the nonimmunoglobulins mentioned above, the antibody also is rendered multivalent by recombination of antibodies that have more than one specificity. For instance, the antibody in some embodiments is capable of binding CTGF as described elsewhere herein, but is also capable of binding a second growth factor, e.g.; TGFβ, VEGF, FGF, other CCN family members, e.g., CYR61, and the like, or a cytokine. Exemplary antibodies directed against these factors are well-known. The multispecific, multivalent antibodies are made by cotransforming a cell with DNA encoding the heavy and light chains of both antibodies and the proportion of expressed antibodies having the desired structure recovered by immunoaffinity chromatography or the like. Alternatively, such antibodies are made from monovalent antibodies that are recombined in vitro in conventional fashion.

Monovalent antibodies also are made by techniques that are conventional per se. Recombinant expression of light chain and a modified heavy chain is suitable. The heavy chain is truncated generally at any point in the Fe region so as to prevent heavy chain crosslinking. Alternatively, the relevant cysteines are substituted with another residue or deleted so as to prevent crosslinking. In vitro methods also are used to produce monovalent antibodies, e.g., Fab fragments are prepared by enzymatic cleavage of intact antibody.

Diagnostics

The antibodies of the present invention can be used to quantitatively and qualitatively detect CTGF in a sample. Samples can be from any source, including conditioned media from cells grown in culture; tissue samples, e.g., tissue biopsies and organ transplants; body fluids including blood, urine, blister fluid, cerebrospinal fluid, vitreous, and synovial fluid; etc. In one embodiment, detection of CTGF is used to diagnose the state of cells grown in culture, e.g., with regard to differentiation, matrix production, etc. CTGF has various autocrine and paracrine effects on cultured cells, and the level of CTGF associated with the cell layer or present in conditioned media may be indicative of the current state of the cell or predictive of the future state of the cell. (See, e.g., International Publication No. WO 96/38168.) In other embodiments, detection of CTGF is used to determine the state of a tissue or organ. For example, an organ destined for transplant can be evaluated by measuring CTGF levels, wherein the level of CTGF expressed by cells in the organ indicate the relative health of the organ and suitability for transplant. CTGF levels can also be determined in biopsied tissue to determine the status of an organ, or the stage and potential metastatic potential of a cancer.

In preferred embodiments, the antibodies are used to diagnose a disease or disorder associated with CTGF. (See, e.g., International Publication No, WO 03/024308.) In one aspect, the invention provides antibodies for diagnosing a CTGF-associated disorder by obtaining a sample, detecting and quantitating the level of CTGF in the sample, and comparing the level of CTGF in the sample to that of a standard amount of CTGF, wherein an increased or decreased amount of CTGF in the sample is indicative of the presence of a CTGF-associated disorder. Disorders associated with aberrant (e.g. increased or decreased) levels of CTGF include, but are not limited to, disorders associated with altered expression and deposition of extracellular matrix-associated proteins. Such disorders include, for example, cancers such as breast, pancreatic, and gastrointestinal cancer; atherosclerosis, arthritis, retinopathies such as diabetic retinopathy; nephropathies such as diabetic nephropathy; cardiac, pulmonary, liver, and kidney fibrosis, and diseases associated with chronic inflammation and/or infection. CTGF-associated disorders are also associated with conditions such as myocardial infarction, diabetes, peritoneal dialysis, chronic and acute transplant rejection, chemotherapy, radiation therapy, and surgery.

In another aspect, the invention provides antibodies for identifying whether or not an individual has a predisposition to develop a CTGF-associated disorder. A predisposition may be initially indicated by hyperglycemia, hypertension, or obesity in a subject. Additionally, a predisposition may be suspected due to an event, e.g., a myocardial infarction, surgery, orthopedic or paralytic immobilization, congestive heart failure, pregnancy, or varicosities in the subject.

In another aspect, the invention provides antibodies for monitoring the progression of a CTGF-associated disorder or monitoring the therapeutic efficacy of treatment of a CTGF-associated disorder. For example, a method of using the antibodies may comprise obtaining samples from a subject over time; detecting and quantitating the level of CTGF in each sample; and comparing the level of CTGF in subsequent samples with CTGF levels in earlier or previous samples. A change in CTGF level between samples over time is indicative of the progression of the CTGF-associated disorder or the therapeutic efficacy of treatment of the CTGF-associated disorder.

For diagnostic applications, the antibodies of the invention typically will be labeled with a detectable moiety. The detectable moiety can be any moiety capable of producing, either directly or indirectly, a detectable signal. For example, the detectable moiety may be a radioisotope, such as $^3H$, $^{14}C$, $^{32}P$, $^{35}S$, or $^{125}I$, a fluorescent or chemiluminescent compound, such as fluorescein isothiocyanate, rhodamine, or luciferin; or an enzyme, such as alkaline phosphatase, beta-galactosidase or horseradish peroxidase.

Any method known in the art for separately conjugating the antibody to the detectable moiety may be employed. (See, e.g., Hunter et al. (1962) Nature 144:945; David et al. (1974) Biochemistry 13:1014; Pain et al. (1981) J Immunol Meth 40; 219; and Nygren (1982) J Histochem Cytochem 30:407.) The antibodies of the present invention may be employed in any known assay method, such as competitive binding assays, direct and indirect sandwich assays, and immunoprecipitation assays. (Zola (1987) In: *Monoclonal Antibodies: A Manual of Techniques*, CRC Press, Inc., pp. 147-158.)

Competitive binding assays rely on the ability of a labeled standard (which may be CTGF or an immunologically reactive portion thereof) to compete with the test sample analyte (CTGF) for binding with a limited amount of antibody. The amount of CTGF in the test sample is inversely proportional to the amount of standard that becomes hound to the antibodies. To facilitate determining the amount of standard that becomes bound, the antibodies generally are insolubilized before or after the competition, so that the standard and analyte that are bound to the antibodies may conveniently be separated from the standard and analyte that remain unbound.

Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three part complex. (David and Greene, U.S. Pat. No. 4,376,110.) The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme. An exemplary assay in which the antibodies of the invention may be used e.g., is described in International Publication No WO 03/024308.

The antibodies of the invention also are useful for in viva imaging, wherein an antibody labeled with a detectable moiety such as a radio-opaque agent, radioisotope, or fluorescent moiety such as green fluorescent protein (GFP) is administered to a host, preferably into the bloodstream, and the presence and location of the labeled antibody in the host is assayed. This imaging technique is useful in the staging and treatment of CTGF-associated disorders such as fibrotic disorders. The antibody may be labeled with any moiety that is detectable in a host, whether by nuclear magnetic resonance, radiology, or other detection means known in the art.

Therapeutics

The present invention provides antibodies for treatment of various diseases and disorders associated with CTGF. The antibodies of the invention have been found to reduce the deleterious effects of CTGF production or activity in several disorders, as exemplified below. Further, the antibodies show favorable pharmacokinetics making them superior therapeutic agents for the treatment of disorders associated with CTGF.

The anti-CTGF antibodies of the present invention inhibit development of fibrosis in animal models of, e.g., lung and kidney fibrosis. Specifically, the antibodies attenuate bleomycin-induced lung fibrosis in mice by 60-70%, as determined by inhibition of pulmonary hydroxyproline (collagen) accumulation and histological examination of tissue preparations. Further, the antibodies reduce the accumulation of collagen in a rat remnant kidney (i.e., ⅚ nephrectomy) model, and in mice following unilateral ureter obstruction (UUO). The antibodies also reduce fibrosis induced by combined subcutaneous or intraperitoneal infusion of CTGF and TGFβ in newborn mice. Additionally, the antibodies reduce complications associated with organ failure, e.g., improved kidney function in various models of chronic and acute kidney failure. No toxicity has been observed with these antibodies in animals. As CTGF is overexpressed in a wide variety of fibrotic diseases including diffuse and limited scleroderma, osteoarthritis, diabetic nephropathy and retinopathy, etc the invention contemplates treating patients with a CTGF-associated disorder with a CTGF antibody to improve or stabilize the pathology, restore organ function, improve the quality of life, and extend survival.

Therefore, the antibodies of the invention are especially useful in therapeutic applications, to prevent or treat CTGF-associated disorders in a subject. Such disorders include, but are not limited to, angiogenesis and other processes which play a central role in conditions such as atherosclerosis, glaucoma, etc.; and in cancer, including acute lymphoblastic leukemia, dermatofibromas, breast cancer, breast carcinoma, glioma and glioblastoma, rhabdomyosarcoma and fibrosarcoma, desmoplasia, angiolipoma, angioleiomyoma, desmoplastic cancers, and prostate, ovarian, colorectal, pancreatic, gastrointestinal, and liver cancer and other tumor growth and metastases.

Additionally, the antibodies of the invention are useful in therapeutic applications to prevent or treat CTGF-associated disorders involving fibrosis. In one aspect, the antibodies of the invention are administered to a subject to prevent or treat a CTGF-associated disorder including, but are not limited to, disorders exhibiting altered expression and deposition of extracellular matrix-associated proteins, e.g., fibrotic disorders. In various aspects, the fibrosis may be localized to a particular tissue, such as epithelial, endothelial, or connective tissue; or to an organ, such as kidney, lung, or liver. Fibrosis can also occur in the eye and joints. In other aspects, the fibrosis may be systemic and involve multiple organ and tissue systems. CTGF-associated disorders include, for example, atherosclerosis, arthritis, retinopathies such as diabetic retinopathy; nephropathies such as diabetic nephropathy; cardiac, pulmonary, liver, and kidney fibrosis, and diseases associated with chronic inflammation and/or infection.

In another aspect, the invention provides antibodies for preventing a CTGF-associated disorder in a subject having a predisposition to develop such a disorder. A predisposition may include, e.g., hyperglycemia, hypertension, or obesity in the subject. Such disorders may occur, e.g., due to diabetes, obesity, etc., and include diabetic nephropathy, retinopathy, and cardiovascular disease. Additionally, a predisposition may be suspected due to an event, e.g., a myocardial infarction, surgery, peritoneal dialysis, chronic and acute transplant rejection, chemotherapy, radiation therapy, trauma, orthopedic or paralytic immobilization, congestive heart failure, pregnancy, or varicosities in the subject.

In particular embodiments, as exemplified herein, the antibodies of the present invention are administered to a subject to treat fibrosis of an organ, e.g., lung or kidney. The antibodies are shown herein to provide benefit in various models of lung and kidney fibrosis. (See, e.g., Examples 7 to 9.) In another particular embodiment, the antibodies of the present invention are administered to a subject to reduce local or systemic sclerosis. (See, e.g., Examples 11 and 12.) In additional embodiments, the antibodies are administered to a subject to treat or prevent ocular disorders such as proliferative vitreoretinopathy, diabetic retinopathy, macular degeneration, etc. As CTGF is implicated in a wide variety of disorders, the invention further contemplates treating patients having a CTGF-associated disorder using an antibody of the invention to improve or stabilize pathology and organ function, improve the quality of life, and extend survival.

For therapeutic applications, the antibodies of the invention are administered to a mammal, preferably a human, in a pharmaceutically acceptable dosage form. The antibodies may be administered intravenously as a bolus or by continuous infusion over a period of time, and/or by intramuscular, subcutaneous, intra-articular, intrasynovial, intrathecal, intravitreal, intracranial, oral, topical, or inhalation, routes. When the antibody possesses the suitable activity, intratumoral, peritumoral, intralesional, or perilesional routes of administration can also be utilized to exert local as well as systemic therapeutic effects.

Such dosage forms encompass pharmaceutically acceptable carriers that are inherently nontoxic and nontherapeutic. Examples of such carriers include ion exchangers, alumina, aluminum stearate, lecithin; serum proteins such as human serum albumin; buffers such as phosphate or glycine; sorbic acid, potassium sorbate, partial glyceride mixtures of saturated vegetable fatty acids, water, salts; or electrolytes such as protamine sulfate, sodium chloride, metal salts, colloidal silica, magnesium trisilicate, polyvinyl pyrrolidone, cellulosic polymers, and polyethylene glycol. Carriers for topical or gel-based forms of antibody include polysaccharides such as sodium carboxymethylcellulose or methylcellulose, polyvinylpyrrolidone, polyacrylates, polyoxyethylene-polyoxypropylene-block polymers, polyethylene glycol, and wood wax alcohols. Conventional depot forms include, for example, microcapsules, nano-capsules, liposomes, plasters, sublingual tablets, and polymer matrices such as polylactide:polyglycolide copolymers. When present in an aqueous dosage form, rather than being lyophilized, the antibody typically will be formulated at a concentration of about 0.1 mg/ml to 100 mg/ml, although wide variation outside of these ranges is permitted.

For the prevention or treatment of disease, the appropriate dosage of antibody will depend on the type of disease to be treated, as defined above, the severity and course of the disease, whether the antibodies are administered for preventive or therapeutic purposes, the course of previous therapy, the patient's clinical history and response to the antibody, and the discretion of the attending physician. The antibody is suitably administered to the patient at one time or over a series of treatments.

Depending on the type and severity of the disease, about 0.015 to 15 mg of antibody/kg of patient weight is an initial candidate dosage for administration to the patient, whether, for example, by one or more separate administrations, or by continuous infusion. For repeated administrations over several days or longer, depending on the condition, the treatment is repeated until a desired suppression of disease symptoms occurs. However, other dosage regimens may be useful and are not excluded from the present invention.

According to another embodiment of the invention, the effectiveness of the antibody in preventing or treating disease may be improved by administering the antibody serially or in combination with another agent that is effective for the same clinical objective, such as another antibody directed against a different epitope than the principal antibody, or one or more conventional therapeutic agents known for the intended therapeutic indication, e.g. prevention or treatment of conditions associated with excessive extracellular matrix production such as fibrosis or sclerosis, inhibition of tumor cell growth or metastasis, inhibition of neovascularization, or reduction of inflammation. Such agents may ameliorate symptoms or improve outcome via a similar mechanism of action, e.g., anti-TGFβ antibodies, or by a different mechanism, e.g., interferon-γ. Such agents may additionally ameliorate symptoms directly or indirectly associated with a CTGF-associated disorder or a predisposition to develop a CTGF-associated disorder, e.g., angiotensin-converting enzyme (ACE) inhibitors and angiotensin receptor blockers (Arbs).

For example, scleroderma patients receiving infusions of the stable prostacyclin agonist Iloprost frequently report an improvement in skin tightness consistent with an inhibitory effect on scar tissue formation by skin fibroblasts. Prostanoids have been shown to exert an inhibitory effect on collagen synthesis, and several lines of evidence demonstrate that Iloprost blocks CTGF induction in scleroderma. (Korn et al. (1980). J Clin Invest 65:543-554; Goldstein and Polger (1982) J Biol Chem 257:8630-8633; and Stratton et al. (2001) J Clin Invest 108:241-250.) CTGF is elevated seven-fold in blister fluid in patients with scleroderma compared with healthy controls, however patients receiving intravenous administration of Iloprost show a marked decrease in CTGF in blister fluid. (Stratton et al. (2001) J Clin Invest 108:241-250.) Taken together, these results suggest that some of the benefits of Iloprost therapy in scleroderma might derive from antifibrotic effects mediated via reduction in CTGF levels. As there are concerns regarding the use of a potent vasodilatory and anti-platelet prostacyclin analog in chronic systemic administration in scleroderma patients, a therapy utilizing an anti-CTGF antibody alone, or in conjunction with reduced levels of Iloprost could provide a safe and effective treatment for scleroderma.

Additional Uses

The antibodies of the invention also are useful as affinity purification agents. In this process, the antibodies against CTGF are immobilized on a suitable support, such as Sephadex resin or filter paper, using methods well known in the art. The immobilized antibody then is contacted with a sample containing the CTGF to be purified, and thereafter the support is washed with a suitable solvent that will remove substantially all the material in the sample except the CTGF that is bound to the immobilized antibody. Finally, the support is washed with another suitable solvent, such as glycine buffer (pH 5.0), that will release the CTGF from the antibody.

EXAMPLES

The invention will be further understood by reference to the following examples, which are intended to be purely exemplary of the invention. These examples are provided solely to illustrate the claimed invention. The present invention is not limited in scope by the exemplified embodiments, which are intended as illustrations of single aspects of the invention only. Any methods which are functionally equivalent are within the scope of the invention. Various modifications of the invention in addition to those described herein will become apparent to those skilled in the art from the foregoing description and accompanying figures, Such modifications are intended to fall within the scope of the appended claims.

Example 1

Production of Recombinant Human CTGF

A recombinant human CTGF baculovirus construct was produced as described in Segarini et al. ((2001) J Biol Chem 276:40659-40667). Briefly, a CTGF cDNA comprising only the open reading frame was generated by PCR using DB60R32 (Bradham et al. (1991) J Cell Biol 114:1285-94) as template and the primers 5'-gctccgcccgcagtggzatccATGac-cgccgcc-3' and 5'-ggatccggatecTCAtgecatgtetccgta-3', which add BamHI restriction enzyme sites to the ends of the amplified product. The native start and stop codons are indicated in capital letters.

The resulting amplified DNA fragment was digested with BamHI, purified by electrophoresis on an agarose gel, and subcloned directly into the BamHI site of the baculovirus PFASTBAC1 expression plasmid (Invitrogen Corp., Carlsbad Calif.). The sequence and orientation of the expression cassette was verified by DNA sequencing. The resulting CTGF expression cassette was then transferred to bacmid DNA by site-specific recombination in bacteria. This bacmid was then used to generate a fully recombinant CTGF baculovirus in *Spodoptera frugiperda* SF9 insect cells according to protocols supplied by the manufacturer (BAC-TO-BAC Expression System manual; Invitrogen). Expansion of recombinant baculovirus titers in Sf9 insect cells was performed using standard procedures known in the art.

Hi5 insect cells were adapted for suspension growth by serial passage of cells in shake flask culture accompanied by enrichment at each passage for separated cells. Suspension Hi5 cells were cultured in 1 L SF900II SFM media (Invitrogen) supplemented with 20 µg/ml gentamicin (Mediatech, Inc., Herndon Va.) and 1× lipid (Invitrogen) in disposable 2.8 L Fernbach culture flasks (Corning Inc., Acton Mass.) on a shaker platform at 110 rpm at 27° C. Once cells reached a density of 1.0–1.5×10$^6$ cells/ml with a viability of >95%, they were infected with recombinant baculovirus at a multiplicity of infection (MOI) of 10. The cultures were then incubated at 27° C. for an additional 40 to 44 hours. The conditioned media, which contains rhCTGF, was collected, chilled on ice, and centrifuged at 5000×g. The supernatant was then passed through a 0.45 mm filter.

Alternatively, recombinant rat CTGF was produced by inserting clone 2-4-7, which encodes rat CTGF (Schmidt et al., U.S. Pat. No. 6,348,329), into pMK33 expression vector (constructed by Michael Koelle, Stanford University Ph.D. dissertation, 1992). The rat CTGF expression construct was transfected into Schneider 2 cells (American Type Culture Collection, Manassas Va.; Schneider (1972). J Embryol Exp Morphol 27:353-365) using CELLFECTIN reagent (Invitrogen Corp., Carlsbad Calif.). Cells were grown in media containing 300 µg/ml hygromycin B for 6 weeks, and were then grown without selection for three days. Expression of CTGF was induced by the addition of 500 µM $CuSO_4$ and 100 µM $ZnSO_4$, and after four days the medium was harvested and clarified by centrifugation and filtration as above.

CTGF produced by either method described above was purified as follows. Four liters of conditioned media was loaded over a 5 ml HI-TRAP heparin column (Amersham Biosciences Corp., Piscataway N.J.) pre-equilibrated with 50 mM Tris (pH7.5), 150 mM NaCl. The column was washed with 10 column volumes of 350 mM NaCl, 50 mM Tris (pH 7.5). CTGF was eluted from the column with an increasing NaCl salt gradient. Eluted fractions were screened by SDS-PAGE, and those containing CTGF were pooled.

Heparin purified CTGF was diluted to a final conductivity of 5.7 mS with non-pyrogenic double-distilled water and the pH was adjusted to 8.0. A Q-SEPHAROSE strong anion exchange column (Amersham Biosciences) containing approximately 23 ml resin connected in tandem with a carboxymethyl (CM) POROS polystyrene column (Applied Biosystems) containing approximately 7 ml resin was utilized for endotoxin removal, and capture and elution of purified rhCTGF. Prior to the sample load, the tandem column was washed with 0.5 M NaOH, followed by 0.1 M NaOH, and finally equilibration buffer. The load sample was passed over the tandem column, the Q-Sepharose column was removed, and CTGF was eluted from the CM POROS column (Applied Biosystems) with an increasing 350 mM to 1200 mM NaCl gradient. The purity of the eluted fractions containing CTGF was evaluated by SDS-PAGE analysis before forming a final sample pool.

Example 2

CTGF N-Terminal and C-Terminal Fragment Production

N-terminal fragments and C-terminal fragments of CTGF were prepared as follows. Recombinant human CTGF, prepared and purified as described above, was digested at room temperature for 6 hours by treatment with chymotrypsin beads (Sigma Chemical Co., St. Louis, Mo.) at 1.5 mg of CTGF per unit of chymotrypsin. The mixture was centrifuged, the chymotrypsin beads were discarded, and the supernatant, containing enyzmatically-cleaved rhCTGF, was diluted 1:5 with 50 mM Tris, pH 7.5. The diluted supernatant was applied to a Hi-Trap heparin column. The flow through, containing N-terminal fragments of CTGF, was collected. The heparin column was washed with 350 mM NaCl, and bound C-terminal fragments of CTGF were eluted with a linear gradient of 350 mM to 1200 mM NaCl, as described above. The fractions were analyzed by SDS-PAGE, and fractions containing C-terminal fragments of CTGF were pooled.

The heparin column flow-through, which contained N-terminal fragments of CTGF, was adjusted to 0.5 M ammonium sulfate/50 mM Tris, pH 7.5 and then loaded onto a 15 ml phenyl sepharose HP column (Amersham-Pharmacia), which had been pre-equilibrated with 0.5 M ammonium sulfate/50 mM Iris, pH 7.5. The column was washed with 15 column volumes of 0.5 M ammonium sulfate/50 mM Iris, pH 7.5, and bound N-terminal fragments of CTGF were eluted with a linear gradient of 0.5 M to 0 M ammonium sulfate ISO mM Tris, pH 7.5, over approximately 15 column volumes. Fractions were analyzed by SDS-PAGE, and fractions containing N-terminal fragments of CTGF were pooled. The pooled solution was concentrated and the buffer exchanged with 50 mM Iris, 400 in M NaCl (pH 7.2), using an ULTRACEL AMICON YM10 ultrafiltration membrane (Millipore Corp., Bedford Mass.), Example 3

Production of Human Anti-CTGF Monoclonal Antibodies

Fully human monoclonal antibodies to human CTGF were prepared using HUMAB mouse strains HCo7, HCo12 and HCo7+HCo12 (Medarex, Inc., Princeton NI). Mice were immunized by up to 10 intraperitoneal (IP) or subcutaneous (Sc) injections of 25-50 mg recombinant human CTGF in complete Freund's adjuvant over a 2-4 weeks period. The immune response was monitored by retroorbital bleeds. Plasma was screened by ELISA (as described below), and mice with sufficient titers of anti-CTGF immunogolobulin were used for fusions. Mice were boosted intravenously with antigen 3 and 2 days before sacrifice and removal of the spleen.

Single cell suspensions of splenic lymphocytes from immunized mice were fused to one-fourth the number of P3X63-Ag8.653 nonsecreting mouse myeloma cells (American Type Culture Collection (ATCC), Manassas Va.) with 50% PEG (Sigma, St. Louis Mo.). Cells were plated at approximately $1\times10^5$ cells/well in flat bottom microtiter plate and incubated for about two weeks in high-glucose DMEM (Mediatech, Herndon Va.) containing L-glutamine and sodium pyruvate, 10% fetal bovine serum, 10% P388D1 (ATCC) conditioned medium, 3-5% origen (Igen International, Gaithersburg Md.), 5 mM HEPES, 0.055 mM 2-mercaptoethanol, 50 mg/ml gentamycin, and 1×HAT (Sigma). After 1-2 weeks, cells were cultured in medium in which the HAT was replaced with HT. Individual wells were then screened by ELISA (described below). Antibody secreting hybridomas were replated, screened again, and, if still positive for anti-CTGF antibodies, were subcloned at least twice by limiting dilution. The stable subclones were then cultured in vitro to generate small amounts of antibody in tissue culture medium for characterization. One clone from each hybridoma that retained the reactivity of the parent cells was used to generate 5-10 vial cell banks stored in liquid nitrogen.

ELISA assays were performed as described by Fishwild et al. (1996, Nature Biotech 14:845-851). Briefly, microtiter plates were coated with 1-2 μg/ml purified recombinant CTGF in PBS at 50 μl/well, incubated at 4° C. overnight, then blocked with 200 μl/well 5% chicken serum in PBS/Tween (0.05%). Dilutions of plasma from CTGF-immunized mice or hybridoma culture supernatants were added to each well and incubated for 1-2 hours at ambient temperature. The plates were washed with PBS/Tween and then incubated with a goat-anti-human IgG Fc polyclonal antibody conjugated with horseradish peroxidase (HRP) for 1 hour at room temperature. After washing, the plates were developed with 0.22 mg/ml ABTS substrate (Sigma) and analyzed by spectrophotometer at 415-495 nm.

Example 4

Antibody Characterization

Hybridomas that produced antibodies to human CTGF were prepared as described in Example 3. Cloned hybridoma cells were grown in Dulbecco's Modified Eagle Medium-High Glucose/RPMI 1640 (50:50) with 8 mM L-Glutamine, ½×Nonessential Amino Acids, and 10% Fetal Bovine Serum. Cells expanded for antibody preparation were grown in the same media with 1.5% Low IgG Fetal Bovine Serum for 4-9 days at 37° C. and 6% $CO_2$. The resulting conditioned media was cleared of cells and concentrated using a tangential flow filtering/concentrating system. The concentrate was passed over a protein-A column and bound monoclonal antibodies doted with 100 mM glycine, pH 3. The eluate was neutralized with 1 M Tris, pH 8.0, and dialyzed against PBS.

4.1 Epitope Mapping

Epitope mapping of antibodies by competitive binding experiments is well known by those skilled in the field of immunology. (See, e.g., Van Der Geld et al. (1999) Clinical and Experimental Immunology 118:487-96.) Each antibody population isolated from cells propagated from a unique cloned hybridoma cell was mapped and assigned to a specific binding domain on human CTGF using standard binding and blocking experiments. (See, e.g., *Antibodies: A Laboratory Manual* (1988) Harlow and Lane (eds), Cold Spring Harbor Laboratory Press; *Tietz Textbook of Clinical Chemistry*, $2^{nd}$ ed., (1994) Chapter 10 (Immunochemical Techniques), Saunders; and *Clinical Chemistry: Theory, Analysis, Correlation* (1984) Chapter 10 (Immunochemical Techniques) and Chapter 11 (Competitive Binding Assays), C.V. Mosby, St. Louis.) Independent binding domains were initially defined by antibody competition experiments in which two different antibodies were incubated in sequential order on CTGF coated plates. If steric hindrance from the first antibody prevented the second antibody from binding to CTGF, then the two antibodies were assigned to the same binding domain. It should be understood, however, that two antibodies might have distinct epitopes yet be near enough to each other to be designated as members of the same binding domain.

Binding domains spanning all four exons of human CTGF were identified. All of the binding domains are conformationally defined, such that the antibodies bind to CTGF under non-reducing conditions in western blot assays. Some of the antibodies also bound to CTGF under reducing conditions in western blot assays, suggesting that each of these antibodies bound to a linear epitope on the CTGF protein. Also, antibodies representing a subset of the binding domains show cross-reactivity to mouse CTGF in western blot analysis. The antibody from each group having the highest affinity for whole CTGF was used for further characterization and analysis.

More refined epitope mapping was performed by ELISA analysis using specific recombinantly expressed fragments of CTGF. For example, antibodies that recognized epitopes on the N-terminal domain of CTGF were identified by ELISA analysis against immobilized fragments obtained from recombinant expression of exon 2 and/or exon 3 of the CTGF gene. In this manner, antibodies that specifically recognize N-terminal domains or N-terminal fragments of CTGF were selected and further characterized. Antibodies that specifically recognize C-terminal domains or C-terminal fragments of CTGF were also selected and further characterized.

The epitope group defined by mAb1 binds to a linear epitope on the N-terminal fragment of CTGF encoded by exon 3. A series of truncated synthetic peptides covering regions encoded by the polynucleotide of exon 3 were generated, and ELISA tests using these peptides were conducted to further define the epitope of mAb1. The results are summarized in Table 1; a "+" indicates binding between the peptide and mAb1, whereas a "−" indicates mAb1 does not bind to the peptide. A boldfaced italic "*C*" indicates a cysteine residue in the peptide that was essential for mAb1 binding. An underlined "C" indicates a cysteine residue added to the end and not a part of the native CTGF sequence.

TABLE 1 mAb1 binding to truncated peptide series encoded by exon 3.

| Peptide | Sequence | mAb1 binding | SEQ ID NO: |
|---|---|---|---|
| N-CTGF |  | + | 27 |
| Exon 3 |  | + | 28 |
| Pep135 | CPLCSMDVRLPSPDCPFPRRVKLP | + | 22 |
| PC5444 | PLSSMDVRLPSPDS | − | 33 |
| PC5445 | RLPSPDSPFPRRVKLPGK | + | 23 |
| PEP5 | RLPSPDCPFPRRVKL | + | 24 |
| P40340 | RLPSPDCPFPRRV | + | 25 |
| P40341 | RLPSPDSPFPRRV | − | 34 |
| P40342 | LPSPDCPFPRRVKL | + | 26 |
| 10MER | SPDSPFPRRV | − | 35 |
| 10MER2 | SPDCPFPRRV | − | 36 |
| 9MER | PDSPFPRRV | − | 37 |
| 9MER2 | CPFPRRVKL | − | 38 |
| 8MER | DSPFPRRV | − | 39 |
| 8MER2 | CFPRRVKL | − | 40 |
| 7MER | CPRRVKL | − | 41 |
| 6MER | CRRVKL | − | 42 |
| 5MER | CRVKL | − | 43 |

Therefore, mAb1 is a member of an antibody class that binds to the N-terminal region of CTGF. The linear epitope on CTGF necessary, and sufficient for binding of mAb1 is defined by amino acid residue L143 through V154 of human CTGF (SEQ ID NO:2). Further confirmation of mAb1 binding specificity for this peptide was obtained by RIA and affinity chromatography. Antibodies that share this epitope, in part or in whole, are specifically included in the present invention. Additionally, antibodies that compete with mAb1 for binding to CTGF or a fragment thereof are also specifically included in the present invention.

4.2 Antibody Affinity for CTGF

Antibody affinity is defined as the strength of the total noncovalent interactions between a single antigen-binding site on an antibody and a single epitope on an antigen. Affinity is calculated by measuring the association constant ($K_a$), such that $$\text{Affinity} = K_a = \frac{[Ab \cdot Ag]}{[Ab][Ag]} = \frac{1}{K_d}$$

where [Ab] is the concentration of free antigen binding site on the antibody, [Ag] is the concentration of free antigen, [Ab·Ag] is the concentration of antigen binding site on the antibody occupied by antigen, and $K_d$ is the dissociation constant of the antibody-antigen complex.

The affinity of each antibody population identified by epitope mapping was measured using RIA, wherein whole rhCTGF was radio-iodinated and added to wells containing immobilized monoclonal antibody, as follows. Recombinant human CTGF was radiolabeled with $^{125}$I using the chloramine-T method. (See, Greenwood et al. (1963) Biochem J 89:114-123.) Typically, at least 60% of the $^{125}$I was incorporated and the specific activity of the labeled CTGF was at least $1 \times 10^5$ cpm/ng, although labeled CTGF of lower specific activity can be used in the radioimmunoassay. Goat anti-human IgG, γFc-specific capture antibody (Jackson ImmunoResearch) in $Ca^{2+}$- and $Mg^{2+}$-free DPBS (Mediatech, Herndon Va.) was added to the wells of a MAXISORP BREAKAPART microliter plate (Nalge Nunc International, Rochester N.Y.) and allowed to bind overnight at 4° C. The wells were then blocked with 1% BSA in $Ca^{2+}$- and $Mg^{2+}$-free DPBS for at least 4 hours at 4° C. The blocking solution was removed and 100 µl of test antibody at 2-50 ng/ml $Ca^{2+}$- and $Mg^{2+}$-free DPBS was added and allowed to bind overnight at 4° C. Mixtures of serial dilutions of unlabelled CTGF in a constant amount of [$^{125}$I]CTGF were added to wells and incubated at room temperature for 4 to 8 hours. Wells were then washed four times with 0.1% Tween 20 in $Ca^{2+}$- and $Mg^{2+}$-free PBS (Mediatech), and the wells of the microliter plate were separated and counted in a gamma counter.

Affinity was estimated graphically by the method of Scatchard (1948, Ann NY Acad Sci 51:660-72). The total concentration of labeled CTGF applied to the plate was calculated as $$[CTGF]_{total} = \frac{\text{cpm\_applied}}{\text{cpm}/\text{fmol}} \cdot \frac{1}{0.1\_\text{ml}} + \frac{[CTGF]_{cold\_stock}}{\text{dilution}}$$

where cpm_applied are counts obtained from control vials, which are loaded with CTGF mixtures in parallel with the wells of the microtiter plate; cpm/final is the specific activity of the [$^{125}$I]CTGF, [CTGF]$_{cold\_stock}$ is the concentration of unlabelled CTGF added to each well, and dilution is the dilution factor for the unlabelled CTGF.

The concentration of CTGF bound to antibody is calculated from the proportion of counts bound to the wells and the total concentration of CTGF applied to the wells.

$$[CTGF]_{bound} = \frac{(\text{cpm\_bound} - \text{blank})}{\text{cpm\_total}} \cdot [CTGF]_{total}$$

The concentration of free (unbound) CTGF is the difference between the total concentration of CTGF applied and the concentration of bound CTGF.

$$[CTGF]_{free} = [CTGF]_{total} - [CTGF]_{bound}$$

Figure 2A:
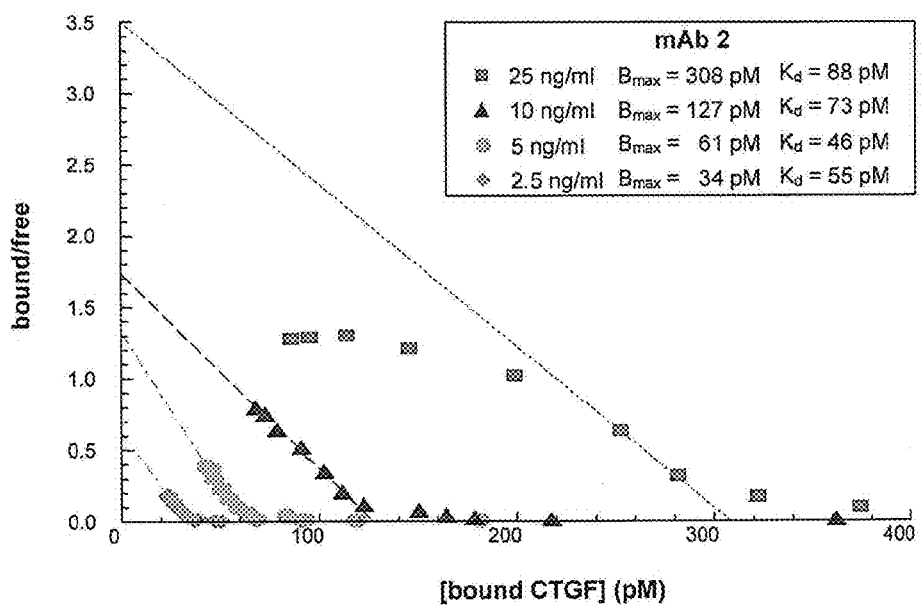
FIGS. 2A and 2B show Scatchard plots of competitive binding between labeled and unlabeled human CTGF to anti-CTGF antibodies, mAb2 and in mAb1, respectively. mAb1 is an exemplary antibody of the present invention.
Figure 2B:
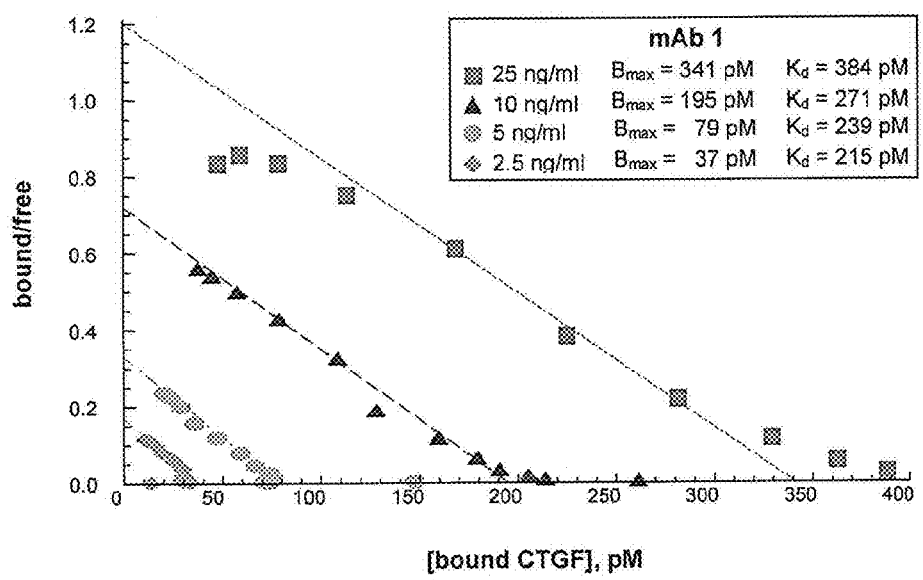

Scatchard plots of affinity determinations for antibodies of the invention are shown in FIG. 2. FIG. 2A plots the binding of an antibody of the invention, mAb2, to [$^{125}$I]rhCTGF in the presence of increasing concentrations of unlabeled rhCTGF. FIG. 2B plots the binding of an exemplary antibody of the invention, mAb1, to [$^{125}$I]rhCTGF in the presence of increasing concentrations of unlabeled rhCTGF. Greater weight is given points with similar proportions of bound and unbound CTGF, because these points will have bound counts in substantial excess of the blanks (hence, well-determined bound counts), but still substantially less than the total counts applied (hence, well-determined free counts). Maximum binding ($B_{max}$) and $K_d$ are represented as the x-intercept and y-intercept, respectively.

The affinity ($K_d$) of mAb1 for CTGF is less than $10^{-9}$ M, the affinity typically found in commercially successful antibody therapeutics. (See, e.g., Maini et al. (1998) Arthritis Rheum 41:1552-1563; Targan et al. (1997) N Engl Med 337: 1029-1035; Bumgardner et al. (2001) Transplantation 72:839-45; and Kovarik et al, (1999) Transplantation 68:1288-94.) Thus, mAb1, is a suitable candidate for therapeutic use and antibodies that share epitope binding with mAb1, as described above, and have an affinity for CTGF that is similar to or greater than mAb1 (that is, a $K_d \leq 10^{-9}$) are likewise suitable candidates for therapeutic use. Antibodies sharing epitope binding with mAb1, but have lower affinity (i.e., higher $K_d$) than mAb1, are also embodied within the present invention and are potentially useful in various assays and diagnostic applications as described herein. Such antibodies may additionally be useful in therapeutic applications, especially if they have a high avidity for antigen, as described below.

4.3 Antibody Avidity

For antibodies with more than one antigen-binding site (multivalency), the affinity at one binding site does not always reflect the true strength of the antibody-antigen interaction. When a multivalent antibody binds to an antigen having multiple repeating epitopes, the interaction of one antigen interaction at one binding site on the antibody increases the chance of antigen interaction with the additional binding sites. Avidity measures the functional combining strength of an antibody with its antigen, which is related to both the affinity of the reaction between the epitopes and paratopes, and the valencies of the antibody and antigen. Thus, avidity provides a more accurate measure of an antibody's tendency to dissociate.

High avidity can compensate for low affinity. For example. IgM antigen-binding sites are generally lower affinity than IgG, but the multivalency of IgM gives it a high avidity, thus enabling it to bind antigen effectively.

To determine the avidity of antibodies of the invention, Fab fragments were first prepared by conventional papain digestion of the corresponding immunoglobulin. Immobilized Protein A was then used to separate the Fab fragments from the Fc and undigested antibody.

Approximately 1 ml immobilized papain slurry containing 0.5 ml settled gel, 250 µg papain, and 3.5 BABE units was washed 3×1 ml and 1×10 ml with Digestion Buffer (DB; 20 mM sodium phosphate, 10 mM EDTA, 20 mM cysteine, pH 7.0). The slurry was then resuspended with 0.3 ml DB, mixed with 1.1 and antibody (approximately 5 mg, pH 7), and agitated overnight at 37° C. The antibody digest was then separated from the resin, and Fab fragments were separated from Fc fragments and undigested antibody by affinity chromatography using Protein A. Purity of Fab fragment was monitored by SDS-PAGE (FIG. 3A).

Monovalent binding was distinguished from bivalent binding by eluting antigen-bound antibodies with varying concentrations of thiocyanate. By increasing chaotropic ion (thiocyanate) concentration in the solution, lower affinity associations (e.g., monovalent binding of Fab to antigen) are disrupted first, while higher affinity associations (e.g., bivalent binding of IgG to ligand) remain undisturbed. Thus, by increasing thiocyanate concentration, two different bindings can be distinguished.

Plates were coated with 10 µg/ml CTGF or CTGF peptides in 50 mM bicarbonate buffer (pH 8.5) at 4° C. overnight, blocked with blocker casein/TBS at 4° C. overnight, and then incubated with 100 µg/ml antibody or corresponding Fab in blocker casein/TBS at room temperature overnight with agitation. Plates were then incubated with dilutions (1:1) of thiocyanate (0-7.6 M) in 100 mM phosphate buffer (pH 6.0) for 15 minutes at room temperature with agitation, followed by an alkaline phosphatase-mouse anti-human $(Fab')_2$ conjugate (1:1000 dilution) at room temperature for 45 minutes. Alkaline phosphatase substrate (1 mg/ml; Sigma) in 1 M diethanolamine, 0.5 mM $MgCl_2$ (pH9.8) was added, plates were incubated at room temperature, and the absorbance at 405 nm was determined after 2, 10, 20, and 60 minutes.

The affinity index is the concentration of chaotropic agent (thiocyanate) that produces a 50% reduction in initial absorbance. For an exemplary antibody of the invention, mAb1, the affinity index for dissociation of Fab from CTGF was 0.46 M, whereas the affinity index for dissociation of intact IgG from CTGF was 1.8 M (FIG. 3B). Thus, mAb1 binds to antigen predominantly bivalently (avidity), and dissociates from antigen much more slowly than an antibody that binds monovalently. Additional antibodies of the invention, which share epitope-binding parameters with in mAb1, may be similarly bivalent or they may be mono- or multi-valent. Any of the antibodies of the invention may be manipulated to improve avidity, e.g., by combining epitope-binding sites into a single antibody construct, e.g., a tribody, etc. (See, e.g., Schoonjans et al. (2000) J Immune 165:7050-7057.)

4.4 Cross-Reactivity

The radioimmunoassay described above (Example 4.2) was used to determine cross-reactivity of the antibodies, except unlabelled rhCTGF was replaced with another unlabelled competitor, rat CTGF derived from normal rat kidney (NRK) cells. NRK cells were grown until confluent and then the culture media was changed to serum-free media containing 2 ng/ml TGF-β2, 50 µg/ml heparin, and 250 µg/ml BSA. Conditioned medium was collected after two days of culture, centrifuged to remove debris, and incubated with heprin-sepharose beads (1/100 v/v bead suspension:medium) for 2 hrs at 4° C. with agitation. The mixture was then centrifuged; the beads were collected and washed with PBS, and then lysed in SDS buffer.

Figure 4A:
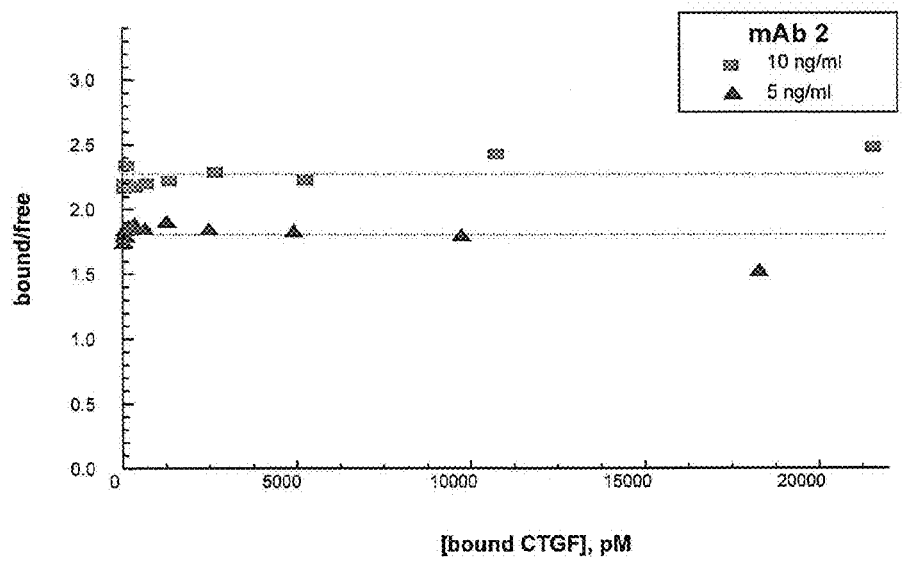
FIGS. 4A and 4B show Scatchard plots of competitive binding between labeled recombinant human CTGF and unlabeled rat CTGF to anti-CTGF antibodies, mAb2 and mAb1, respectively.
Figure 4B:
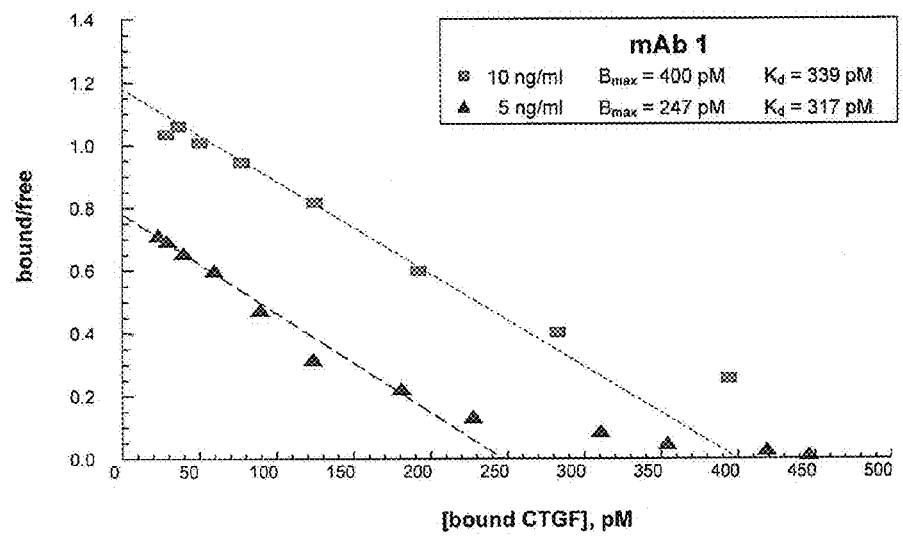

A Scatchard plot of the binding of mAb2 to [$^{125}$I]rhCTGF in the presence of increasing concentrations of unlabeled rat CTGF is shown in FIG. 4A; and a Scatchard plot of the binding of mAb1 to [$^{125}$I]rhCTGF in the presence of increasing concentrations of unlabeled rat CTGF is shown in FIG. 4B. As can be seen in the figure, mAb1 binds to both human and rat CTGF, while mAb2 binds to human but does not bind to rat CTGF.

For mAb1, the Scatchard plots for competition with rat CTGF (FIG. 4B) have shallower slopes, lower apparent affinity, and higher apparent $B_{max}$ than the plots for competition with rhCTGF (FIG. 2B). Thus, although rat CTGF is able to compete with human CTGF for binding to mAb1, the antibody has higher affinity for recombinant human CTGF than for recombinant rat CTGF. mAb1, also cross-reacts with mouse and monkey CTGF (data not shown). Antibodies showing suitable affinity for CTGF from other species may be used in treatment and prevention of disorders in those species. For example, an antibody of the invention that shows a suitable $K_d$ for canine CTGF could be used to treat a CTGF-associated disorder in dogs. Antibodies of the invention that show cross-species affinity, such as mAb1, are also useful as research tools, to study CTGF-associated disorders in various animal models.

4.5 Glycosylation

The radioimmunoassay described above (Example 4.2) was used to determine the effect of antibody glycosylation on antigen binding affinity. Antibody mAb1 was treated for 8 days at 37° C. in PBS, 0.5 M EDTA, pH 8.0, with peptide N-glycosidase F (PNGase F), which cleaves oligosaccharides from N-linked glycoproteins. After incubation, the reaction solution was either used directly or fractionated on a protein A-SEPHAROSE FASTFLOW column (Amersham Bioscience, Piscataway N.J.) and eluted with 0.1 M glycine-HCl, pH 2.5. Antibody recovery after fractionation was approximately 87%, and the endotoxin level was 0.30 EU/mg. Deglycosylation was confirmed by SDS-PAGE. Binding activity of deglycosylated antibody to human recombinant CTGF was identical within experimental error to the binding activity of the glycosylated form of the antibody.

As various cells produce different glycosylation patterns, production of recombinant proteins, e.g., antibodies, in cultured cells or non-homologous species may generate non-native glycosylation. Some proteins require specific glycosylation for activity, and altered glycosylation reduces activity; e.g., in the case of antibodies, affinity for antigen is reduced. Protein production in certain systems, e.g., plants and chicken eggs, may also produce glycosylation patterns that are immunogenic, thus reducing the ability to use the proteins in certain applications. The ability of the present antibodies to show the same activity in a glycosylated and non-glycosylated form demonstrate that the invention is not limited by the presence of glycosylation, particularly a species-specific glycosylation.

Example 5

Cell Migration Assay

Cell migration is a normal and important cellular event, e.g., during development and wound healing. Cell migration is also a factor in the pathology of disorders such as formation of fibrotic lesions, and cells isolated from fibrotic lesions are more responsive to chemotactic stimulants than cells from corresponding normal tissue.

Antibodies of the present invention were analyzed for their ability to inhibit CTGF-stimulated chemotactic migration of smooth muscle cells using a Boyden chamber assay as follows. Rat arterial smooth muscle cells (ASMCs) in media containing 0.1% fetal calf serum (FCS) were added to the upper compartment of a Boyden chamber, and media containing either 300 ng/ml rhCTGF, 10% FCS, or 0.1% FCS alone was added to the lower compartment. A collagen-coated filter having pores with a diameter of 8 μm separated the upper chamber from the lower chamber. Cells were allowed to adhere to and migrate through the filter for 2-3 hours. The filter was then removed, the cells on the filter were fixed and stained, and the cells that migrated through the filter were counted. Incubation with 300 ng/ml rhCTGF increased the number of cells migrating through the filter approximately 5-fold relative to 0.1% FCS controls. The increase in migration stimulated by CTGF was approximately 27% of the chemotactic effect seen with 10% FCS, which contains multiple chemotactic factors.

The antibodies of the invention were tested for their ability to inhibit CTGF-mediated cell migration using the assay described above, except either anti-CTGF antibody (at 30 and 300 mg/ml) or pooled human IgG was also added to the lower chamber. Four fields of cells from each of 3 separate filters were counted for each sample m each assay. Results are shown in Table 2.

TABLE 2

Inhibition of CTGF-mediated cell migration.

| Antibody | Cell Migration (%) | |
| --- | --- | --- |
| | Average | SD |
| hIgG | 100 | 10 |
| 7 (30 μg/ml) | 77 | 13 |
| 19 (30 μg/ml) | 71 | 14 |
| 19 (300 μg/ml) | 43 | 12 |

As can be seen in Table 2, antibodies that bind to CTGF within the epitope defined by mAb1 inhibit CTGF-mediated cell migration in a dose-dependent manner. The antibodies of this epitope group were the only anti-CTGF antibodies tested that repeatedly and reproducibly inhibited CTGF-induced migration.

Various processes, such as angiogenesis, chondrogenesis, and oncogenesis require alterations in cell adhesion and migration. CTGF has been associated with both cell adhesion and migration, and the ability of antibodies directed against CTGF to differentially affect one activity versus another provides a diverse repertoire of therapeutic agents for the treatment of CTGF-associated conditions. The antibodies provided by the present invention clearly demonstrate differential activity relating to neutralization of CTGF activities. As exemplified below, these abilities provide unique therapeutic potential in this class of anti-CTGF antibody.

Example 6

Pulmonary Disorders

The intratracheal (IT) instillation of bleomycin in mice is a model system widely used for studying lung fibrosis and for screening potentially desirable antifibrotic agents. Antibodies of the invention were tested for their ability to reduce bleomycin-induced lung fibrosis in vivo using the procedure described by Wang et al, (2000) Biochem Pharmacol 60:1949-1958, as follows.

Male C57BL/6 mice were randomly divided into two groups. Mice were anesthetized with isofluorane, and then injected intratracheally with either a single dose of bleomycin in 0.9% saline at 0.1 unit/50 μl/mouse or 0.9% saline alone. Each group was divided and treated immediately and thereafter once every other day for a total of seven doses with either saline or antibody administered intraperitoneally (IP). Fourteen days after the IT instillation, mice were euthanized by exsanguination of the descending abdominal aorta under anesthesia and lung tissue was harvested.

Lung collagen content was analyzed by measuring the level of hydroxyproline and proline using the method of Palmerini et al. (1985; J Chromatogr 339:285-292), except that L-azetidine 2-carboxylic acid (Aldrich) was substituted for 3,4-dehydroproline as the internal standard. Briefly, tissue samples were hydrolysed in 6 N HCl for 22 hours at 105° C. Samples underwent pre-column derivitization with o-phthaladehyde and then 4-chloro-7-nitrobenzofuran (Aldrich) to form fluorescent adducts of proline and hydroxyproline. The fluorescent adducts were separated by reverse phase HPLC followed by fluorometric detection.

FIG. 5 shows the result of therapeutic administration of saline (SA), an exemplary antibody of the invention, mAb1, and a pool of CTGF-specific antibodies (AbsJ) were compared for their ability to suppress lung fibrosis following bleomycin treatment. As can be seen in FIG. 5A, bleomycin treatment (BL+SA) significantly increased lung hydroxyproline content 168% over the control group (SA+SA; 220±15 µg/lung). However, subsequent treatment with pooled antibodies of the invention (BL+AbsJ) showed a 60% decrease in lung hydroxyproline compared to the bleomycin-treatment alone. Similarly, subsequent treatment with mAb1 (BL+mAb1) showed a 70% decrease in lung hydroxyproline compared to bleomycin alone.

Histological examination of the mouse lungs revealed normal pulmonary parenchymal tissue in the control group (not shown). In bleomycin treated lungs, however, an increase in regions of fibrosis was clearly seen (FIG. 5B; arrows). Therapeutic administration of an antibody of the invention subsequent to bleomycin treatment showed a clear reduction in fibrosis (FIG. 5C), although some lobes still showed a mild degree of interstitial fibrosis. Thus, antibodies of the invention provide therapeutic benefit when administered to patients at risk for or suffering from a pulmonary disorder such as idiopathic pulmonary fibrosis (IPF).

Example 7

Renal Disorders 7.1. Renal Failure

Tubulointerstitial fibrosis is a major component of several kidney diseases associated with the progression to end-stage renal failure, (Sharma et al. (1993) Kidney Int 44:774-788.) Unilateral ureteral obstruction (UUO), characterized by decreased renal function and increased interstitial fibrosis, has been used as an experimental model to induce tubulointerstitial damage and fibrosis. (Fern et al. (1999) J Clin Invest 103:39-46.)

Mice were anesthetized with isofluorane, and then ligation of the left ureter was performed according to the method described by Moriyama et al. (1998; Kidney Int 54:110-119). Mice were treated immediately following surgery and thereafter once every other day for a total of seven doses with either saline or antibody administered intraperitoneally (IP). Fourteen days after UUO, animals were anesthetized and sacrificed by exsanguination of the descending abdominal aorta. Both the right and left kidneys were separately decapsulated and weighed. Half of each kidney was fixed in 10% formalin for histology (trichrome stain) and the other half was weighed and stored at −70° C. for hydroxyproline determination. Hydroxyproline and praline were determined as described above.

Figure 6A:
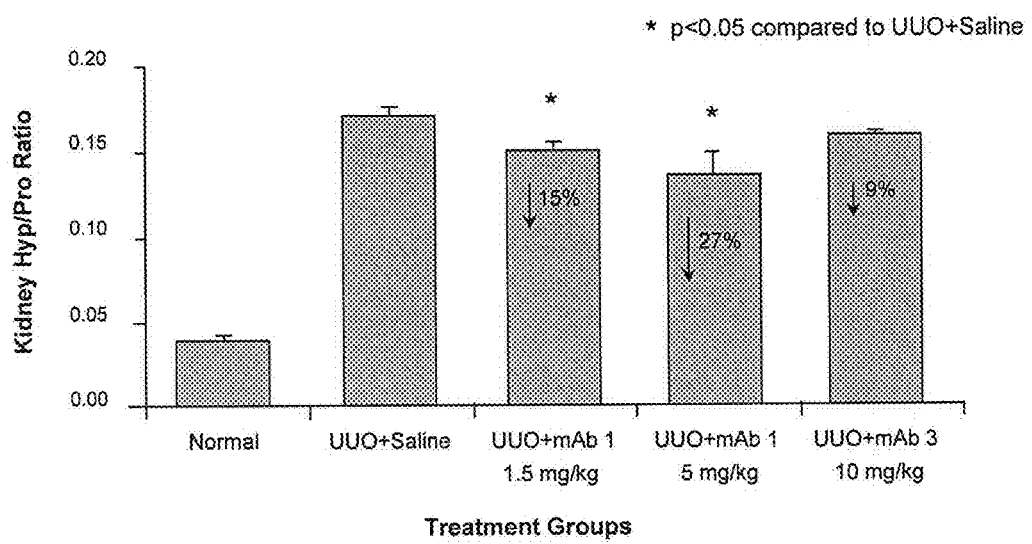
FIGS. 6A, 6B, and 6C show the therapeutic benefits of an antibody of the invention in a model of tubulointerstitial fibrosis in the kidney.
Figures 6B, 6C:
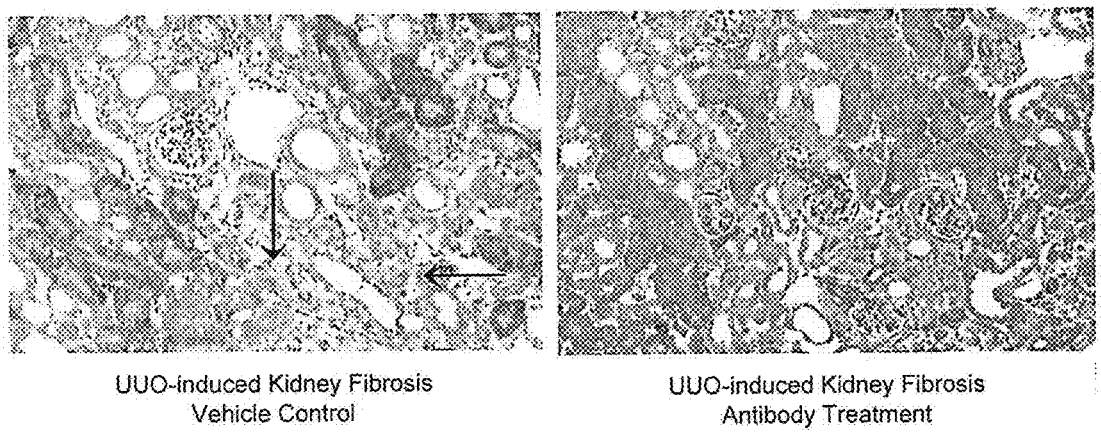

As can be seen in FIG. 6A, UUO increased the kidney collagen content approximately 4-fold, as measured by the hydroxyproline to proline ratio of the obstructed left kidney relative to the unobstructed right kidney in each mouse. Treatment with an antibody of the invention, mAb1, resulted in a statistically significant dose-dependent reduction in fibrosis of the obstructed kidney (FIG. 6A). However, an antibody that binds to a C-terminal epitope on CTGF, mAb3, did not show significant effect. Trichrome staining of MK) kidney identifies regions of increased collagen accumulation (FIG. 6B, arrows), whereas treatment with an antibody of the invention shows a considerable reduction in collagen staining in the obstructed kidney (FIG. 6C).

Alternatively, kidney fibrosis can be studied in the rat remnant kidney model of progressive renal failure. The model, which involves ⅔ unilateral nephrectomy combined with complete renal ablation contralaterally (⅚ total nephrectomy), induces degenerative parenchymal changes associated with chronic renal failure in the renal remnant, and animals become uremic and exhibit marked albuminuria, glomerulosclerosis, interstitial fibrosis and tubular atrophy. (See, e.g., Frazier et al. (2000) Vet Pathol 37:328-335; and Gandhi et al. (1998) Kidney Int 54:1157-1165.)

The ⅚ nephrectomy was performed according to Frazier et al. (2000, Vet Pathol 37:328-335). Five-week-old male Sprague-Dawley rats (Harlan, Indianapolis Ind.) averaging 120 g were anesthetized with ketamine and xylazine, and the cranial ⅓ and caudal ⅓ of the left kidney was incised. A gauze sponge was briefly applied to provide hemostasis, the abdomen was rinsed with saline, 0.2 ml butorphenol, and the animal was sutured. One week after the initial surgery, the contralateral kidney was removed completely.

Rats were divided into saline and antibody treated groups with treatment initiated 2 weeks following ⅚ nephrectomy. Saline or antibody at a dosage of 5 mg/kg was administered by IP injection (0.5 mL each) every 3 days for 15 days (a total of 5 injections). Blood and urine samples were taken weekly from random nephrectomized rats to follow the development of renal disease and to correlate renal functional disturbance with histologic changes. Results from renal fibrosis analysis, urinalysis and serum chemistry assays were compared between the groups at 18 and 28 days after treatment initiation.

Renal fibrosis was evaluated independently by two pathologists in a blinded fashion; three histologic sections from each kidney were examined using three distinct morphologic stains: hematoxylin/eosin, Masson's trichrome and picric acid-sirius red. In addition, immunohistochemistry was performed on frozen sections to assess the type of collagen deposition at each location in the kidney. Quantitative collagen evaluation (hydroxyproline/proline ratio) was performed and renal function was assessed using both urinalysis and serum chemistry of samples collected at the time of euthanasia.

Figure 7A:
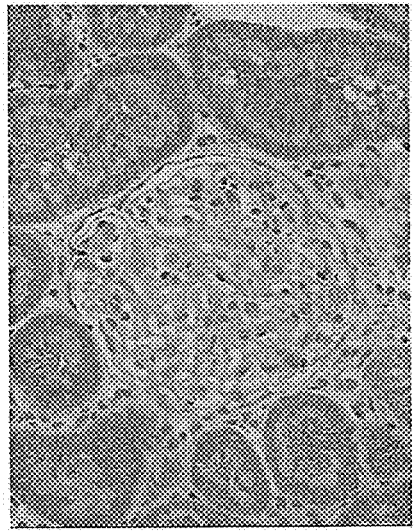
FIGS. 7A and 7B show the therapeutic benefit of an antibody of the invention in a model of glomerular fibrosis in the kidney.
Figure 7B:
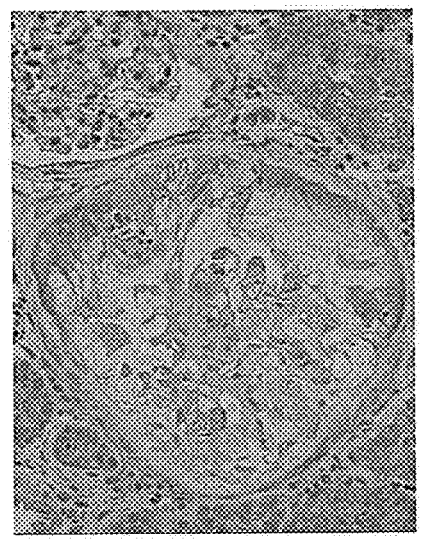

Histologically, moderate differences in fibrosis were noted between untreated and antibody treated remnant kidneys (FIG. 7). At 3 days post-treatment, blinded subjective evaluation resulted in a mean fibrosis score of 12.6 in saline treated group versus 10.7 in antibody treated group (p<0.05). Statistically significant differences in histologic fibrosis grade between antibody and saline treated rats were maintained at 14 days post-treatment, with a mean fibrosis score of 16.9 in the saline treated group versus 14.4 in the antibody treated group (p<0.05). The quantitative hydroxyproline content analysis of collagen also demonstrated a trend towards decreased fibrosis in the antibody-treated group relative to the saline-treated group, but the difference was not statistically significant.

Qualitative differences were also noted between treatment groups. While most of the collagen deposition in the antibody treated groups was limited to the corticomedullary and medullary interstitium, the fibrosis in the saline treated rats was multifocal to diffusely distributed throughout the cortex and medulla. The most marked histopathologic differences were in the amount of glomerular fibrosis. Many of the saline treated group had moderate to severe glomerulosclerosis with pericapsular fibrosis, thickened Bowman's membrane, synechia, and glomerular obsolescence. These changes were minimal to mild in the other groups, including the antibody treated rat kidneys. Collagen accumulation was visualized with Masson's trichrome and picric acid-sirius red stains.

In both models of progressive renal failure, antibody of the invention reduced tissue degradation and improved kidney function. Thus, antibodies of the invention provide therapeutic benefit when administered to patients at risk for or suffering from a renal disorder such as glomerulonephritis, IgA nephropathy, glomerulosclerosis; and kidney failure and tubule destruction due to toxins, etc.

7.2. Diabetic Nephropathy

Diabetes leads to failure of multiple organs including, but not limited to, kidney, heart and eye. A major component of the pathological progression of diabetic organ failure is fibrosis. An established model of diabetic nephropathy is a mouse carrying a loss-of-function mutation in the leptin receptor (Ob-R; encoded by the db gene). Key features in common between the db/db mouse and human diabetic nephropathy include renal hypertrophy, glomerular enlargement, albuminuria, and mesangial matrix expansion.

Antibodies of the invention were tested using the db/db mouse model of diabetic nephropathy as follows. Eight-week-old db/db mice (Harlan, Indianapolis Ind.) and their heterozygous db/littermates were treated by intraperitoneal injection with either antibody of the invention (CLN1; see below) or control human IgG (cIgG). In all animals, an initial injection of 300 µg of antibody was followed by 100 µg doses administered 3 times per week for 60 days. Blood samples were collected and body weights were measured at the beginning of and periodically throughout the treatment period. Food consumption was also recorded.

By 11 weeks, clear distinction existed between the diabetic (db/db) animals and the non-diabetic (db/+) animals with respect to body weight, blood glucose levels, and food consumption. Treatment with either antibody of the invention or control antibody did not significantly affect any of these parameters. However, various measurements of kidney function demonstrated a clear difference between diabetic and non-diabetic mice. As can be seen in Table 3, diabetic mice showed increased kidney weight, creatinine clearance, and albumin excretion rate (AER) relative to non-diabetic mice. However, diabetic animals treated with antibody of the invention showed normalized values for all the parameters. All data are expressed as Mean±SEM. The number of mice per group (n) ranged from 9 to 15.

TABLE 3

Kidney function in dh/db and db/+ mice.

| Animal Group | Treatment | Kidney wt (mg) | Creatinine (ml/h) | AER (µg/24 h) |
|---|---|---|---|---|
| db/+ | cIgG | 133.8 ± 5.1 | 2.17 ± 0.29 | 0.30 ± 0.02 |
| db/+ | mAb1 | 141.0 ± 4.3 | 2.37 ± 0.19 | 0.23 ± 0.04 |
| db/db | cIgG | 207.8 ± 3.9** | 5.39 ± 0.36** | 2.52 ± 0.20** |
| db/db | mAb1 | 177.4 ± 4.5* | 2.76 ± 0.31$^\Delta$ | 0.98 ± 0.09□ |

**$P < 0.01$ vs. db/+ mice.
*$P < 0.01$ vs. db/+ mice and $P < 0.05$ cIgG-treated db/db mice.
$^\Delta P < 0.01$ vs. cIgG-treated db/db mice.
□$P < 0.01$ vs. db/+ mice and cIgG-treated db/db mice.

As CTGF is induced by high glucose and mediates various activities including ECM production in tissues as a result of damage, e.g., due to advanced glycation endproduct (AGE) formation and accumulation, etc., pathologies associated with diabetes, such as diabetic nephropathy, may be prevented using the antibodies of the invention.

Example 8

Ocular Disorders

Increased expression of CTGF has been associated with various ocular disorders including proliferative vitreoretinopathy (PVR), macular degeneration, and diabetic retinopathy. (See, e.g., Hinton at al. (2002) Eye 16:422-428; He et al. (2003) Arch Ophthalmol 121:1283-1288; and Tikellis et al. (2004) Endocrinology 145:860-866.) The role of CTGF and the use of anti-CTGF therapeutics has been proposed. (See International Publication No. WO 03/049773.) The antibodies of the present invention represent a unique, therapeutically efficacious class of anti-CTGF therapeutic for use in such ocular disorders. The ability of antibodies of the present invention to ameliorate complications in ocular disorders is tested in models of ocular disease as follows.

8.1. Diabetic Retinopathy

Animal models of diabetes, e.g., db/db mice, are described in Example 7.2, above. Any of these models can, be used to demonstrate the efficacy of treatment of diabetic retinopathy using the antibodies of the invention. A particular model for diabetic retinopathy is provided below, wherein animals are injected with streptozotocin (STZ), a known toxin of the insulin-secreting pancreatic β-islet cells.

Diabetes is induced in rats (e.g., Long-Evans, Sprague-Dawley, etc.) by injection, e.g., intraperitoneally, of streptozotocin (STZ), e.g., at about 60 to 85 mg/kg body weight. To improve survival, rats may be given 10% sugar water for 24 hours and/or 2 to 4 units insulin per day following STZ injection. Various factors including, e.g., body weight, urinary albumin excretion rate, blood glucose, glycated hemoglobin, blood pressure, etc., are measured after, e.g., 4, 8, and 12 weeks. Control animals injected with buffer alone are followed concurrently. One half of the STZ-treated and control rats are additionally treated with antibody of the invention injected, e.g., intravenously, intraperitoneally, or intraocularly. Throughout the study animals are given access to food and water ad libitum. Animals are sacrificed at 12 weeks, and eyes are harvested and examined for histological changes.

A reduction in pathological changes in antibody-treated animals relative to non-treated controls is indicative of therapeutic efficacy in diabetic retinopathy. As CTGF is induced by high glucose and mediates various activities including ECM production in tissues as a result of damage, e.g., due to advanced glycation endproduct (AGE) formation and accumulation, etc., pathologies associated with diabetes, such as diabetic retinopathy, may be prevented using anti-CTGF therapeutics. (See, e.g., International Publication No. WO 03/049773.) The antibodies of the present invention represent a unique, therapeutically efficacious class of anti-CTGF therapeutic for use in ocular disorders, e.g., diabetic retinopathy.

8.2. PVR

Rabbit retinal pigmented epithelial (RPE) cells are isolated from adult rabbit eyes and cultured in DMEM supplemented with 10% fetal bovine serum. Subconfluent cultures (typically at passage 2 to 3) are used for all subsequent injections. At the time of injection, cultured RPE cells are collected and suspended in PBS to approximately $2.5 \times 10^6$ cells/ml. Approximately 0.2 mls of aqueous humor is removed from each recipient rabbit eye using a 25-gauge needle, and then RPE cells are injected through the sclera to a point three millimeters posterior to the limbus just over and above the optic disc using a 27-gauge needle. Following injection of RPE cells, either 0.1 ml PDGF BB (50-150 ng), CTGF (200-400 ng), or PDGF and CTGF in PBS is injected through the same entrance site. The non-injected eye of each animal serves as a control. Optionally, CTGF can additionally be injected on day 7 and/or day 14 following first injection. One half of the animals are additionally treated with antibody of the invention injected. e.g., intravenously, intraperitoneally, or intraocularly. Depending on the administration site, antibody may be provided daily or administered less frequently, e.g., on days 7, 10, 14, etc.

Animals are examined using indirect ophthalmoscopic procedures to monitor development and extent of PVR, which is classified according to parameters described by Fastenberg. (Fastenberg et al. (1982) Am J Ophthalmol 93:565-572.) Animals are then sacrificed and eyes are analyzed by histological examination for both extent of membrane formation and fibrosis. Additionally, retina and fibrotic membrane may be collected for measurement of collagen content.

Alternatively, PVR is induced in rabbit eyes using subretinal injection of dispase, using the model and a procedure adapted from Frenzel et al. (1998, Invest Ophthalmol V is Sci 39:2157-2164.) A subretinal bleb is formed using 50 ml (0.05 U) of Dispase (Sigma Chemical Co.) in PBS. One half of the animals are additionally treated with antibody of the invention injected, e.g., intravenously, intraperitoneally, or intraocularly. Retinal detachment is induced in approximately 75% of the injected rabbits not receiving antibody of the invention one week after surgery, and in approximately 100% of these animals two weeks following surgery. Epiretinal membranes are examined for extent of fibrosis.

A reduction in pathological changes in antibody-treated animals relative to non-treated controls is indicative of therapeutic efficacy in PVR. As CTGF has been associated with tissue damage in models of PVR, anti-CTGF agents have been proposed as therapeutics for use in such disorders. (See, e.g., International Publication No. WO 03/049773.) The antibodies of the present invention represent a unique, therapeutically efficacious class of anti-CTGF therapeutic for use in ocular disorders, e.g., PVR.

Example 9

Sclerosis

Sclerosis is generally characterized by diffuse fibrosis, degenerative changes, and vascular abnormalities in the skin (scleroderma), joints, and internal organs, especially the esophagus. GI tract, lung, heart, and kidney.

9.1. Localized Granuloma Induction

Newborn mice develop a persistent localized fibrosis when administered a combination of human-derived TGF-β2 and CTGF by subcutaneous injection over 7 consecutive days. (Mori et al. (1999) J Cell Physiol 181:153-159; Shinozaki et al. (1997) Biochem Biophys Res Commun 237:292-297.)

Figure 8A:
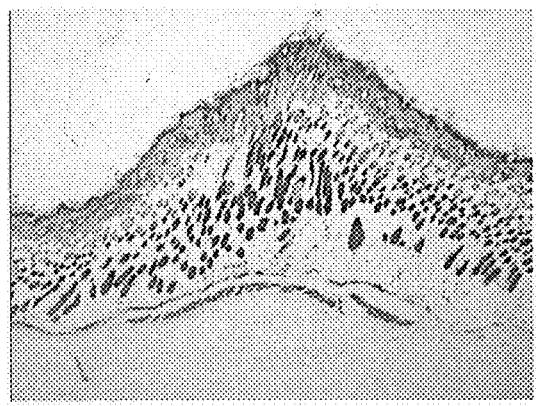
Figure 8B:
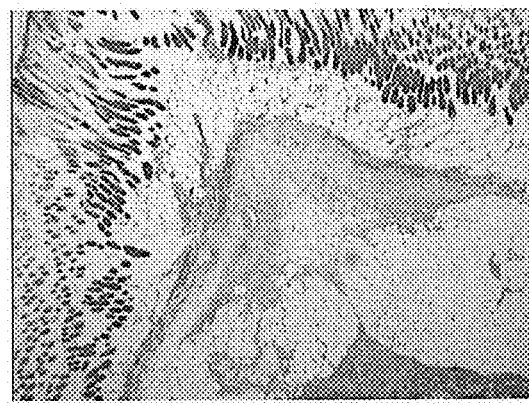
Figure 9:
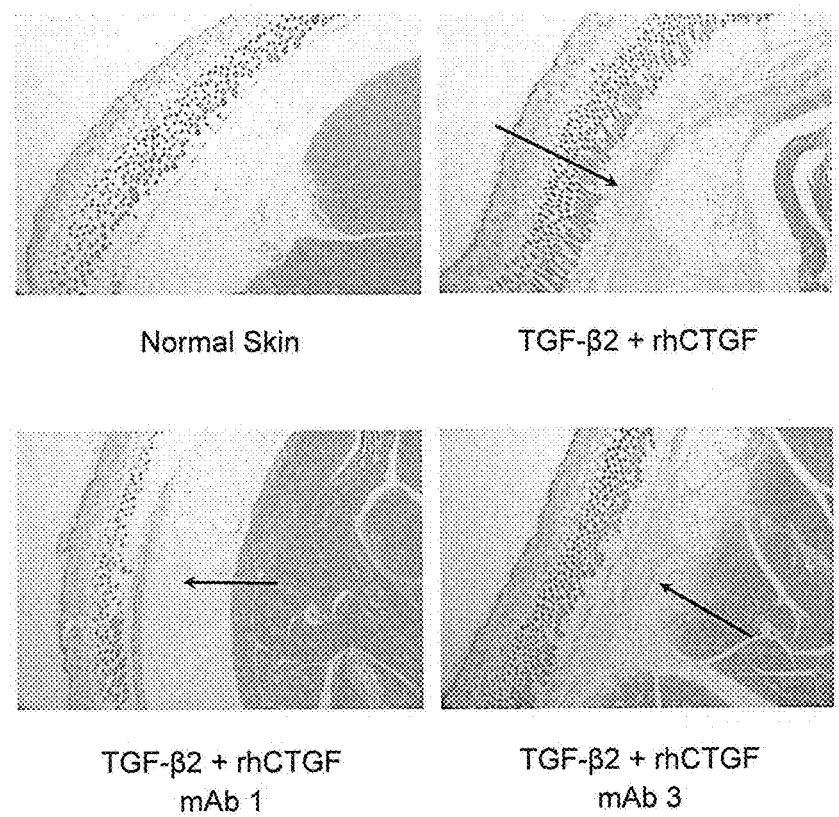
FIG. 9 shows degree of fibrosis in a localized subcutaneous granuloma model with and without treatment with anti-CTGF antibodies. mAb1 is an exemplary antibody of the invention, whereas in mAb3 is an anti-CTGF antibody that specifically binds to a C-terminal CTGF epitope.

One day after birth, mice were divided into three treatment groups and administered 40 μl % mouse serum albumin (MSA), PBS containing either 800 ng TGF-β2, 400 ng CTGF, or both TGF-β2 and CTGF by subcutaneous injection into the subscapular region for 7 consecutive days. The combination TGF-β2 and CTGF group was further divided into two groups, with one group additionally receiving 40 μg antibody of the invention, mAb1. On Day 11, animals were sacrificed and sections of the injection sites were processed and stained with Mason's trichrome for histological assessment. The slides were randomized and evaluated qualitatively in a blinded fashion by three scientists; scoring ranged from 0 (no change) to 4 (fibrotic tissue) based on the degree of fibrosis or connective tissue expansion (see FIG. 8). Cumulative scores from each slide from all the individual reviewers were then calculated and the mean value compared among the groups using ANOVA test.

Group mean scores for the vehicle control, TGF-β2, and TGF-β2 and CTGF combination were 0.75, 6.83 and 9.00, respectively (Table 4).

TABLE 4

Histological scoring of granuloma in neonatal mice

| Treatment | Mean Score | Sid Err | Group Size |
|---|---|---|---|
| Vehicle | 0.75 | 0.48 | 4 |
| TGF-β2 | 6.83 | 0.65 | 6 |
| TGF-β2 + rhCTGF | 9.00 | 0.72 | 7 |
| TGFβ2 + CTGF + mAb1 | 6.17 | 1.40 | 6 |
| TGFβ2 + CTGF + FG-3025 | 7.50 | 1.50 | 4 |

[1] Group scoring of slides from 3 different readers.

Group mean score for antibody treatment was 6.17, a statistically significant reduction when compared with the corresponding TGF-β2 and CTGF combination (p<0.05), while treatment with a C-terminally directed, non-neutralizing anti-CTGF antibody, mAb3, did not reduce fibrosis. Thus, antibodies of the present invention are particularly effective at reducing local sclerotic damage to tissues.

9.2, Neonatal Systemic Fibrosis

Newborn mice were divided into groups and administered daily intraperitoneal injections for 21 consecutive days with 300 μg/kg/day TGFβ, 300 μg/kg/day CTGF, a combination of 300 μg/kg/day each TGFβ and CTGF, or the combination of TGFβ and CTGF preceded by IP administration of 5 mg/kg antibody of the invention, in mAb1, 30 min prior to growth factor treatment. Pups remained with their mothers during the course of treatment. On Day 21, animals were sacrificed, major organs were removed, and total proline and hydroxyproline were measured as above.

Figures 10A, 10B, 10C, 10D:
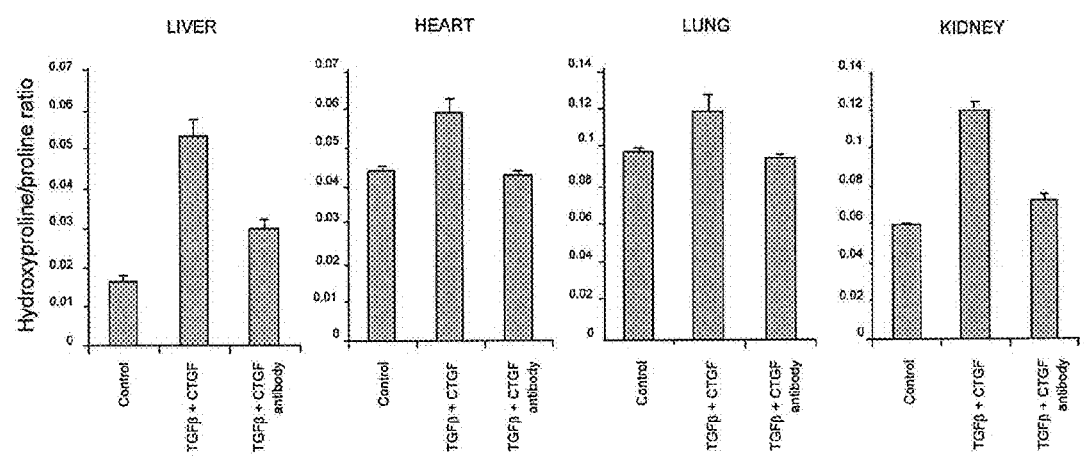
FIGS. 10A, 10B, 10C, and 10D show the therapeutic benefit of an antibody of the invention in organ fibrosis using a model of systemic sclerosis. Each of the panels shows changes in collagen accumulation in respective organs following treatment with saline (control), TGFβ and CTGF, or TGFβ and CTGF treatment concomitant with antibody therapy.

Daily injections of TGFβ induced minor systemic fibrosis, whereas CTGF alone produced no response. The combination of TGFβ and CTGF induced systemic fibrosis with extensive collagen deposition in several organs (FIG. 10) including liver, lung, heart, GI tract, diaphragm and kidney; extensive intestinal adhesions; and a 25% increase in mortality. Administration of the antibody of the invention in conjunction with growth factor treatment reduced or prevented organ fibrosis (FIG. 10) and intestinal adhesions, and prevented mortality. Thus, antibodies of the present invention are additionally effective when administered systemically at reducing sclerotic damage to various tissues and organs. The results presented in Examples 10.1 and 10.2 clearly demonstrate that the antibodies of the invention, when administered locally or systemically, are therapeutically efficacious for the treatment of sclerotic conditions.

9.3. Scleroderma

The antibodies of the invention can be used to ameliorate fibrosis associated with scleroderma. Methods that measure the extent and severity of skin disease in scleroderma are known within the art. (See, e.g., Rodnan et al. (1979) Arthritis Rheum 22:130-40; Aghassi et al. (1995) Arch Dermatol 131: 1160-1166; Brennan et al, (1982) Br J Rheumatol 31:457-460; Kahaleh et al. (1986) Clin Exp Rheumatol 4:367-369; Falanga and Bucalo (1993) J Am Acad Derm 29:47-51;

Seyger et al, (1997). J Am Acad Derm 37:793-796; Seyger et al. (1998) J Am Acad Dermatol 39: 220-225; Black (1969) Br J Dermatol 81:661-666; Ballou et al. (1990) J Rheurmtol 17:790-794; and Enomoto et al. (1996) J Am Acad Dermatol 35:381-387.)

For example, modified Rodnan skin score measures skin hardness using a Type OO Rex DD-3 digital durometer (Rex Gauge Company, Buffalo Grove Ill.) in standardized durometer units with 0.1 unit resolution. Durometer measurements are performed at all the same skin sites as measured by Rodnan skin scoring. Skin scores and durometer readings are performed at baseline screening, prior to administration of an antibody of the invention, and every three months throughout the dosing and follow-up periods. Each measurement is repeated four times, and a structured analysis of variance and calculation of intraclass correlation coefficients is used to determine between repetition variability in relation to site and patient variability. (Fleiss (1971) Psychol Bull 76:378-382.) Correlation techniques are also used to assess the concordance between skin scores and durometer scores, both for overall scores and for sub-group scores, at a given point in time. Lagged correlation analyses (e.g., relating durometer scores at entry to skin scores at time t+3 months, or t+6 months of treatment with antibody) is also performed. Disease activity and functional status information can also be collected, including collagen synthesis data (PIIINP measurements). Reduction in symptoms and/or complications of scleroderma as measured using any of the methods described above demonstrates therapeutic efficacy of the antibodies of the present invention.

Example 10

Osteoarthritis

Antibodies of the present invention are tested in one of the following models to demonstrate therapeutic efficacy in osteoarthritis. For the following examples, concentration of antibody used is in the range of about 0.015 to 15 mg antibody per kilogram of subject body weight; e.g., a dosage of about 5 mg antibody per kilogram body weight, is considered appropriate.

Animals, e.g., 12-week-old male C57B116 mice, are housed in standard cages and fed a standard diet with tap water ad libitum.

10.1 Intra-Articular Injection of AdCTGF in Marine Knee Joints

A CTGF-containing adenovirus expression vector construct (AdCTGF) is prepared using the ADEASY system (Qbiogene, Carlsbad Calif.) according to procedures supplied by the manufacturer. Briefly, a polynucleotide encoding full-length human CTGF is inserted using standard molecular cloning techniques into a PSHUTTLE-CMV plasmid (Qbiogene). The pShuttle-CMV-CTGF construct is then linearized and co-transfected with PADEASY-1 plasmid (Qbiogene) into competent E. coli BJ-5183 cells by electroporation. AdCTGF is amplified and purified using procedures described by Kim et al. (2001, J Biol Chem 276:38781-38786); an empty adenoviral vector is used as a control. Plaque-forming units (range $1.0-2.1\times10^{10}$/ml) and virus particles (range $0.9-1.5\times10^{12}$/ml) are similar for AdCTGF and control virus.

AdCTGF or control adenovirus ($1\times10^7$ plaque-forming units) is injected intra-articularly; and antibodies of the invention are administered by intra-articular, intravenous, intraperitoneal, or subcutaneous injection. Antibody may be injected at the same time as adenoviral administration or, alternatively, therapy may begin either before or after injection of AdCTGF. Animals receiving control adenovirus are similarly injected with either anti-CTGF antibody or control antibody. Non-injected knee joints serve as controls for antibody affects.

Knee joints are isolated on various days, e.g., 1, 3, 7, 14, and/or 28 days, after AdCTGF injection, decalcified for 14 days in EDTA/polyvinylpyrrolidone, and stored at −20° C. using the procedure described in Stoop et al. (2001, Osteoarthritis Cartilage 9:308-315). Histology of joints is analyzed to measure synovial thickness and proteoglycan depletion; in situ hybridization and immunohistochemistry is performed to identify CTGF expression, as well as expression of additional factors including collagen (type I and/or III), etc. Synovial fluid is collected to determine levels of CTGF, metalloproteinases, etc. Efficacy of therapy using anti-CTGF antibodies is confirmed by a reduction in parameters associated with osteoarthritis relative to animals injected with AdCTGF and treated with control antibody.

10.2 Infra-Articular Injection of AdTGFβ in Marine Knee Joints

Alternatively, antibodies may be tested in the animal model of osteoarthritis described by Bakker et al. (2001, Osteoarthritis Cartilage 9:128-136). For example, antibody of the invention or control antibody may be injected at the same time as, subsequent to, or in advance of intra-articular injection of $1\times10^7$ pfu TGFβ-expressing adenovirus construct (AdTGFβ). Non-injected knee joints serve as controls for antibody effects. On various days, e.g., Day 3, 7, 14, etc., animals from each group are sacrificed and tissues are isolated and processed. Histology of joints is analyzed to measure synovial thickness, proteoglycan depletion, and osteophyte formation, etc.; in situ hybridization and immunohistochemistry is performed to identify CTGF expression, as well as expression of additional factors including collagen (type I and/or III), etc. Synovial fluid is collected to determine levels of TGFβ, CTGF, metalloproteinases, etc. Efficacy of therapy using antibodies of the invention is confirmed by a reduction in parameters associated with osteoarthritis relative to animals injected with AdTGFβ and treated with control antibody.

10.3 Intro-Articular Infection of Papain Murine Knee Joints

Alternatively, antibodies may be tested using the procedure described in van der Kraal) et al. (1989, Am J Pathol 135: 1001-1014). Intra-articular injection of papain induces osteophyte formation, fibrosis, and proteoglycan depletion from articular cartilage. The papain model is initiated by injecting 1 unit of papain solution (Sigma, St. Louis, Mo.) into the right knee joint of the mice. The left knee joint of each animal serves as an internal control. Antibodies of the invention are administered by intra-articular, intravenous, intraperitoneal, or subcutaneous injection at the same time as, subsequent to, or in advance of intra-articular injection of papain (0.5%/ knee). On various days, e.g., Day 3, 7, 14, etc., animals from each group are sacrificed and tissues are isolated and processed. Histology of joints is analyzed to measure synovial thickness, proteoglycan depletion, and osteophyte formation, etc.; in situ hybridization and immunohistochemistry is performed to identify CTGF expression, as well as expression of additional factors including collagen (type I and/or III), etc. Synovial fluid is collected to determine levels of TGFβ, CTGF, metalloproteinases, etc. Efficacy of therapy using anti-CTGF antibodies is confirmed by a reduction in parameters associated with osteoarthritis relative to animals injected with papain and treated with control antibody.

Example 11

Cloning and Expression

Although the following example illustrates the cloning and expression of one particular antibody of the invention, the methods are generally applicable to all of the antibodies described and claimed herein.

An exemplary antibody of the invention, in mAb1, was first identified as part of a complex human antibody secreted by a hybridoma cell line (8C12-F10; prepared as described in Example 3).

1.1 Cloning and Sequencing of mAb1 Heavy Chain

Messenger RNA was isolated from a culture of 8C12-F10 cells using a MICRO-FAST TRACK kit (Invitrogen) following protocols provided by the manufacturer. Two cDNA pools were then produced by second strand synthesis using a cDNA cell cycle kit (Invitrogen) following protocols provided by the manufacturer and one of the following heavy chain antisense primers:

```
AB90        (TGCCAGGGGGAAGACCGATGG;  SEQ ID NO: 3)

m19 H1504R  (GCTGGGCGCCCGGGAAGTATGTA; SEQ ID NO: 4)
```

Heavy chain variable region sequences were cloned by PCR amplification of the AB90-primed cDNA pool using AB90 primer and one of a series of V-region primers, including primers corresponding to conserved secretory signal sequences, which encode the 5' end of the respective coding regions, and framework region 1 sequences, which encode the beginning of the mature immunoglobulins. Phi DNA polymerase (Stratagene) was used according to recommended manufacturer's protocols, with the following variations: Reactions were typically carried out in 50 µl total volume, containing 1 cDNA, 0.75 µM each forward and reverse primer, 200 µM each dNTP, and 1 µPfu polymerase (2.5 units per µl). A countdown thermal cycler program was used with an initial incubation at 94° C. for 2 min prior to addition of enzyme. The following cycle parameters were then used: Ten cycles of 94° C. for 45 seconds, 65° C. for 45 seconds, and 72° C. for 1 minute; thirty cycles of 94° C. for 45 seconds, 55° C. for 45 seconds, and 72° C. for 1 minute; and then one cycle at 72° C. for ten 10 minutes.

Only one heavy chain signal sequence primer, AB87 (ATGGAGTTTGGRCTGAGCTC; SEQ ID NO:5), which binds to VH3 family heavy chain V regions, produced significant product. The 453 nucleotide PCR product was cloned into PCR BLUNT II-TOPO vector (Invitrogen), clones were screened for the correct insert size, and three clones corresponding to the PCR products were sequenced. Identical sequences were obtained for all three clones.

Heavy chain constant and UTR region sequences were cloned by PCR amplification of the m19 H1504R-primed cDNA pool. A 601 nucleotide PCR fragment corresponding to the 5' end of the heavy chain segment was amplified using sense primer VI-13-33 29-51F (CGGCGOTGTTTCCAT-TCGGTGAT; SEQ ID NO:6) and heavy chain constant region antisense primer m19 H553R (GGGCGCCT-GAGITCCACGACAC; SEQ ID NO:7). Topoisomerase-mediated cloning was used to clone the PCR products into PCR-BLUNT II vector (Invitrogen), as directed by the manufacturer, and the insert was then sequenced. Similarly, a 505 nucleotide PCR fragment was amplified using sense primer m19 H439F (GTCTTCCCCCTGGCACCCTCCTC; SEQ ID NO:8) and antisense primer m19 H943R(CCCGCG-GCTTTGTCTTGGCATTAT; SEQ ID NO:9), and a 503 nucleotide PCR fragment was amplified using sense primer m19 H1002F (CTGGCTGAATGGCAAGGAGTA; SEQ ID NO:10) and antisense primer m19 H1504R. Both fragments were separately cloned into PCR-BLUNT II vector (Invitrogen) and sequenced as described above. A fourth heavy chain PCR fragment of 586 nucleotides was amplified using sense primer m19 H645F (GGGCACCCAGACCTACATC; SEQ ID NO:11) and antisense primer m19 H1230R (CTC-CGQCTGCCCATTGCTCTCC; SEQ ID NO:12) and sequenced directly.

Figure 11A:
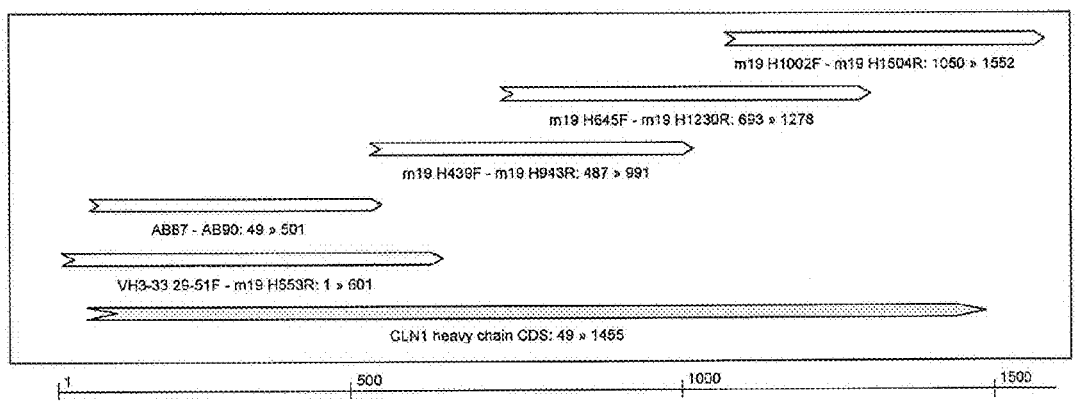
FIGS. 11A and 11B show a diagrammatic representation of the cloning of heavy and light immunoglobulin chains of an exemplary antibody of the invention, mAb1.

FIG. 11A shows a diagram of the alignment of the cloned PCR fragments which provided the full length nucleotide sequence (SEQ ID NO:13) that encodes the mAb1 heavy chain (SEQ ID NO:14). The amino acid sequence of the heavy chain variable region most closely resembles VH3 germ line gene DP-44. Although it was not possible to tell which D segment had been used, the sequence of mAb1 most closely resembles the DH4 family. The JH region most closely matches germ line JH4 and JH5. The heavy chain constant region of in mAb1 matches GenBank Accession No. BC016381, indicating an allotype of G1m(3).

11.2 Cloning and Sequencing of in mAb1 Light Chain

Messenger RNA was isolated from a culture of 8C12-F10 cells using a MICRO-FAST TRACK kit (Invitrogen) following protocols provided by the manufacturer. Two cDNA pools were then produced by second strand synthesis using a cDNA cell cycle kit (Invitrogen) following protocols provided by the manufacturer and one of the following light chain antisense cDNA primers:

```
AB16      (CGGGAAGATGAAGACAGATG;  SEQ ID NO: 15)

Ck-760R   (AAGGATGGGAGGGGGTCAGG;  SEQ ID NO: 16)
```

Light chain variable region sequences were cloned by PCR amplification of the AB16-primed cDNA pool using AB16 primer and one of a series of V-region primers including primers corresponding to conserved secretory signal sequences, which encode the 5' end of the respective coding regions, and framework region 1 sequences, which encode the beginning of the mature immunoglobulins. Pfu DNA polymerase (Stratagene) was used according to recommended manufacturer's protocols with the variations and cycle parameters described above.

Only one light chain signal sequence primer, AB123 (CCCGCTCAGCTCCTGGGGCTCCTG; SEQ ID NO:17), which binds to VK1 family heavy chain V regions, produced significant product. The 408 nucleotide PCR product was cloned into PCR BLUNT II-TOPO vector (Invitrogen), clones were screened for the correct insert size, and three clones corresponding to the PCR products were sequenced. Identical sequences were obtained for all three clones.

Light chain constant region sequences were cloned by PCR amplification of the Ck-760R-primed cDNA pool. The entire coding sequence and 5' UTR region of the light chain was amplified using light chain sense primer L15 22m (TCAGW-CYCAGTCAGGACACAGC; SEQ ID NO:18) and Ck-760R. The 788 nucleotide fragment was cloned into PCR BLUNT II vector (Invitrogen) and sequenced. The resulting plasmid was designated 41m6.

Figure 11B:
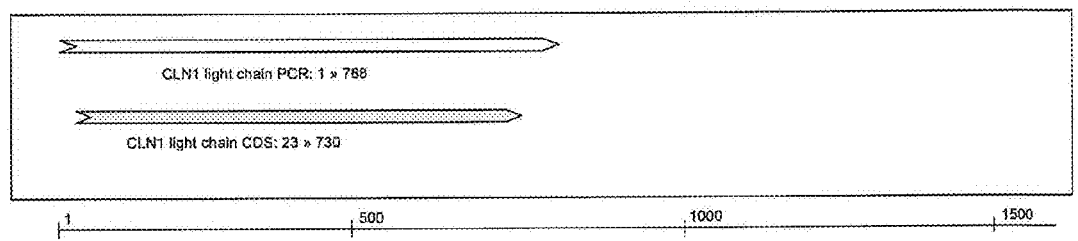

FIG. 11B shows a diagram of the alignment of the cloned PCR fragments which provided the full length nucleotide sequence (SEQ ID NO:19) that encodes the mAb1 light chain (SEQ ID NO:20). The amino acid sequence of the light chain variable region most closely matches regions encoded by germ line Vk L15 and Jk2 nucleotide sequences. The light chain constant region of mAb1 is identical to the reported human germ-line kappa light chain immunoglobulin gene sequence. (Whitehurst et al. (1992) Nucleic Acids Res 20:4929-4930.)

11.3 Production of in Heavy and Light Chain Expression Constructs

Full-length mAb1 heavy chain cDNA was generated by overlap extension PCR in two steps from the heavy chain PCR products described above and shown in FIG. 11A. The two 5' PCR products were combined with the distal primers VH3-33 29-51F and m19 H943R in a PCR overlap extension reaction to produce a single fragment of 991 nucleotides. Similarly, the two 3' PCR products were combined with the distal primers VH3-33 29-51F and m19 H943R in a PCR overlap extension reaction to produce a fragment of 860 nucleotides. These two PCR extension reaction products were then gel-purified and amplified together using the distal primers VH3-33 29-51F and m19 H1504R to generate the 1407 nucleotide cDNA (residues 441 through 1847 of SEQ ID NO:13) coding sequence of the full-length mAb1 heavy chain.

The heavy chain cDNA was then cloned into PCR-BLUNT II TOPO vector (Invitrogen) to produce plasmid 43a4. The mAb1 heavy chain coding region was then subcloned by digestion of plasmid 43a4 with BamHI and XbaI restriction endonucleases, followed by ligation of the excised insert into PCDNA5-FRT expression vector (Invitrogen), which had been pre-digested with BamHI and Nhe restriction endonucleases. The insert of the resulting expression plasmid. 44a 1, was sequence verified before being similarly subcloned in reverse orientation into PBK-CMV vector (Clontech) to produce plasmid 47a4, and into pCEP-Pu vector (E. Kohfeldt, Max-Planck-Institut fur Biochemie), a vector derived from pCEP4 vector (Invitrogen), to produce plasmid 49a1.

The 708 nucleotide cDNA (residue 415 through 1122 of SEQ ID NO:19) encoding full-length mAb1 light chain was excised from plasmid 41 m6, described above, using HindIII and Xho I restriction endonucleases, and ligated into PCDNA5-FRT vector (invitrogen), which had been pre-digested with HindIII and XhoI restriction endonucleases, to produce the mammalian expression plasmid 42b2. The insert of plasmid 42b2 was sequence verified before being similarly subcloned in reverse orientation into PBK-CMV vector (Clontech) to produce plasmid 47b3, and into pCEP-Pu vector (E. Kohfeldt, Max-Planck-Institut fur Biochemie) to produce plasmid 49b1.

11.4 Transfection and Expression of Antibody Chain Constructs

COS7 cells were transfected with plasmids 44a1 (mAb1 heavy chain) and 42b2 (mAb1 light chain) in both separate and co-transfections using standard procedures. Conditioned culture media was assayed for the presence of antibody as described in Example 4 (supra). Only medium from cells co-transfected with both 44a1 and 42b2 expressed human antibody having CTGF-binding activity as measured by ELISA using procedures as described above. The antibody, herein identified as CLN1, produced by the co-transfected COS7 cells, binds to the N-terminal half of CTGF with an affinity of 0.8 nM.

CLN1 has also been expressed in genetically modified Chinese Hamster Ovary (CHO) cells. A CHO cell line expressing exemplary antibody CLN1 was deposited with the American Type Culture Collection (Manassas Va.) on 19 May 2004 and is identified by ATCC Accession No PTA-6006. Cell lines can be optimized and antibody expression can be enhanced using various techniques known in the art, e.g., by gene amplification as described by Wigler et al. (1980; Proc Natl Acad Sci USA 77:3567-3570) with modifications as described by Ringold et al. (1981; J Mol Appl Genet. 1:165-175), Gasser et al. (1982; Proc Natl Acad Sci USA 79:6522-6526), and Kaufman et al. (1985; Mol Cell Biol 5:1750-1759).

Example 12

Interaction of CTGF with TGFβ

Antibodies of the invention specifically bind to regions of CTGF defined by residues encoded by exon 3 (FIG. 1B; nucleotide 418 to nucleotide 669 of SEQ ID NO:1). This region encompasses amino acid 97 to amino acid 180 of SEQ ID NO:2, and includes the von Willebrand Type C domain (amino acid 103 to amino acid 164 of SEQ ID NO:2) and the epitope of mAb1 (amino acid 134 to amino acid 158 of SEQ ID NO:2). Abreu et al. (2002, Nat Cell Biol 4:599-604) report that a domain corresponding to the VWC domain of CTGF is important for interaction between CTGF and TGFβ or BMP-4, and that said interaction modulates the activity of TGFβ and BMP-4. The following experiments demonstrate that regions encoded by exon 3 are necessary and sufficient for binding of CTGF to TGFβ, and that antibodies of the invention can block the interaction between CTGF and TGFβ.

Interaction between CTGF and TGF was assayed using the following procedure. The wells of a 96-well MAXISORP ELISA plate (Nalge Nitric) were coated overnight at 4° C. with 10 μg/ml of either CTGF, the CTGF fragment encoded by exon 3, or the CTGF fragment encoded by exon 5, in PBS; or with PBS alone. All wells were then blocked with 1% BSA in PBS, followed by incubation for 1 hour at room temperature in 50 μl solution containing TGFβ at 0, 1, 3.3, 10, 33, 100, 333, or 1000 ng/ml, and MAB612 or MAB1835 mouse anti-TGFβ monoclonal antibody (R&D Systems, Minneapolis Minn.) at 100, 300, or 1000 ng/ml in PBS, 0.05% Tween-20. MAB1835 recognizes bovine, mouse, and human TGF-β1, and -β2, and blocks binding of TGF to mouse thymocytes. MAB612 recognizes TGF-β2, but does not inhibit TGFβ activities. Wells were washed with PBS, 0.05% Tween-20, and then incubated for 1 hour at room temperature in a solution containing an alkaline phosphatase-conjugated goat anti-mouse IgG antibody diluted in PBS, 0.05% Tween-20. Plates were again washed, and p-nitrophenyl phosphate (PNPP) in 1 M ethanolamine, 1 mM MgSO4, pH 9.8 was added, wells were incubated for a suitable time to develop, and the reaction was then terminated by addition of NaOH. The absorbance at λ of 405 nm was measured using a spectrophotometer.

Figure 12A:
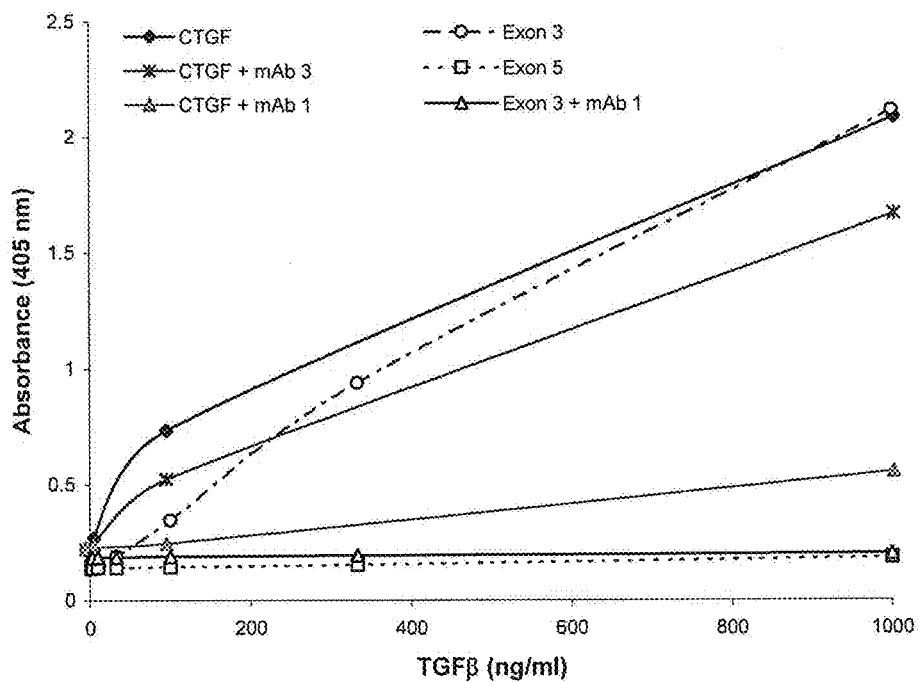
FIGS. 12A and 12B shows binding studies between CTGF and TGFβ.
Figure 12B:
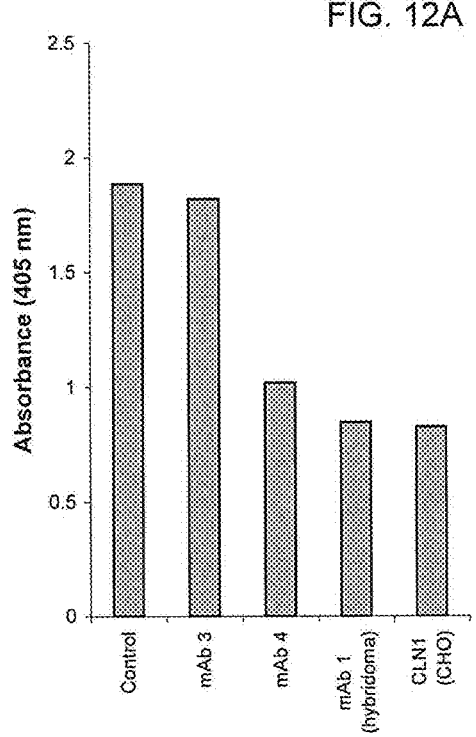

FIG. 12 shows that CTGF and the CTGF fragment encoded by exon 3 are capable of interacting with TGFβ to an equivalent degree, whereas the CTGF fragment encoded by exon 5 did not show any binding activity toward TGFβ. Interestingly, the anti-TGFβ antibody MAB612 was able to detect CTGF-bound TGFβ in a dose-dependent manner, but the neutralizing antibody, MAB1835, was not able to detect CTGF-bound TGF at any concentration tested (data not shown). This suggests that CTGF competes with MAB1835 for binding to TGF.

Anti-CTGF antibodies were tested for their ability to block binding between CTGF and TGFβ. As shown in FIG. 12, anti-bodies of the invention, exemplified by mAb4 and mAb1, blocked TGFβ binding of both CTGF and the CTGF fragment encoded by exon 3, whereas an anti-CTGF antibody directed to a C-terminal fragment of CTGF did not block binding. These results provide support for a mechanism of action wherein antibodies of the invention specifically block an interaction between CTGF and TGFβ, and potentially between CTGF and other members of the TGFβ superfamily.

Various modifications of the invention, in addition to those shown and described herein, will become apparent to those skilled in the art from the foregoing description. Such modifications are intended to fall within the scope of the appended claims.

All references cited herein are hereby incorporated by reference in their entirety.

What is claimed is:

1. A polynucleotide sequence comprising a sequence selected from the group consisting of:
   (a) a polynucleotide sequence encoding SEQ ID NO:14;
   (b) a polynucleotide sequence encoding from amino acid 1 through amino acid 167 of SEQ ID NO:14;
   (c) SEQ ID NO:13; and
   (d) nucleotide 1 through nucleotide 501 of SEQ ID NO:13.

2. A recombinant polynucleotide comprising the polynucleotide sequence of claim 1 operably linked to a vector sequence that contains replication and transcriptional control sequences.

3. The recombinant polynucleotide of claim 2, wherein the polynucleotide encodes the amino acid sequence of SEQ ID NO:14.

4. The recombinant polynucleotide of claim 3, wherein the polynucleotide comprises SEQ ID NO:13.

5. An isolated host cell transfected with the recombinant polynucleotide of claim 2.

6. A polynucleotide sequence comprising a sequence selected from the group consisting of:
   (a) a polynucleotide sequence encoding SEQ ID NO:20;
   (B) a polynucleotide sequence encoding from amino acid 1 through amino acid 136 of SEQ ID NO:20;
   (c) SEQ ID NO:19; and
   (d) nucleotide 1 through nucleotide 408 of SEQ ID NO:19.

7. A recombinant polynucleotide comprising the polynucleotide sequence of claim 6 operably linked to a vector sequence that contains replication and transcriptional control sequences.

8. The recombinant polynucleotide of claim 7, wherein the polynucleotide encodes the amino acid sequence of SEQ ID NO:20.

9. The recombinant polynucleotide of claim 8, wherein the polynucleotide comprises SEQ ID NO:19.

10. An isolated host cell transfected with the recombinant polynucleotide of claim 7.

11. An isolated host cell comprising a cell co-transfected with a polynucleotide sequence encoding SEQ ID NO:14 and a polynucleotide sequence encoding SEQ ID NO:20.

12. The cell line identified by ATCC Accession No. PTA-6006.

* * * * *

SEQUENCE LISTING

<160> NUMBER OF SEQ ID NOS: 43

<210> SEQ ID NO 1
<211> LENGTH: 2075
<212> TYPE: DNA
<213> ORGANISM: Homo sapiens

<400> SEQUENCE: 1

| | | | | | |
|---|---|---|---|---|---:|
| cccggccgac | agccccgaga | cgacagcccg | gcgcgtcccg | gtccccacct | ccgaccaccg | 60 |
| ccagcgctcc | aggccccgcg | ctccccgctc | gccgccaccg | cgccctccgc | tccgcccgca | 120 |
| gtgccaacca | tgaccgccgc | cagtatgggc | cccgtccgcg | tcgccttcgt | ggtcctcctc | 180 |
| gccctctgca | gccggccggc | cgtcggccag | aactgcagcg | ggccgtgccg | gtgcccggac | 240 |
| gagccggcgc | cgcgctgccc | ggcgggcgtg | agcctcgtgc | tggacggctg | cggctgctgc | 300 |
| cgcgtctgcg | ccaagcagct | gggcgagctg | tgcaccgagc | gcgaccctg | cgacccgcac | 360 |
| aagggcctct | tctgtgactt | cggctccccg | gccaaccgca | agatcggcgt | gtgcaccgcc | 420 |
| aaagatggtg | ctccctgcat | cttcggtggt | acggtgtacc | gcagcggaga | gtccttccag | 480 |
| agcagctgca | agtaccagtg | cacgtgcctg | gacggggcgg | tgggctgcat | gccctgtgc | 540 |
| agcatggacg | ttcgtctgcc | cagccctgac | tgccccttcc | cgaggagggt | caagctgccc | 600 |
| gggaaatgct | gcgaggagtg | ggtgtgtgac | gagcccaagg | accaaaccgt | ggttgggcct | 660 |
| gccctcgcgg | cttaccgact | ggaagacacg | tttggcccag | acccaactat | gattagagcc | 720 |
| aactgcctgg | tccagaccac | agagtggagc | gcctgttcca | agacctgtgg | gatgggcatc | 780 |
| tccacccggg | ttaccaatga | caacgcctcc | tgcaggctag | agaagcagag | ccgcctgtgc | 840 |
| atggtcaggc | cttgcgaagc | tgacctggaa | gagaacatta | agaagggcaa | aaagtgcatc | 900 |
| cgtactccca | aaatctccaa | gcctatcaag | tttgagcttt | ctggctgcac | cagcatgaag | 960 |
| acataccgag | ctaaattctg | tggagtatgt | accgacggcc | gatgctgcac | cccccacaga | 1020 |
| accaccaccc | tgccggtgga | gttcaagtgc | cctgacggcg | aggtcatgaa | gaagaacatg | 1080 |
| atgttcatca | agacctgtgc | ctgccattac | aactgtcccg | gagacaatga | catctttgaa | 1140 |
| tcgctgtact | acaggaagat | gtacggagac | atggcatgaa | gccagagagt | gagagacatt | 1200 |
| aactcattag | actggaactt | gaactgattc | acatctcatt | tttccgtaaa | atgatttca | 1260 |
| gtagcacaag | ttatttaaat | ctgttttct | aactggggga | aaagattccc | acccaattca | 1320 |
| aaacattgtg | ccatgtcaaa | caaatagtct | atcttcccca | gacactggtt | tgaagaatgt | 1380 |
| taagacttga | cagtggaact | acattagtac | acagcaccag | aatgtatatt | aaggtgtggc | 1440 |
| tttaggagca | gtgggagggt | accggcccgg | ttagtatcat | cagatcgact | cttatacgag | 1500 |
| taatatgcct | gctatttgaa | gtgtaattga | gaaggaaaat | tttagcgtgc | tcactgacct | 1560 |
| gcctgtagcc | ccagtgacag | ctaggatgtg | cattctccag | ccatcaagag | actgagtcaa | 1620 |
| gttgttcctt | aagtcagaac | agcagactca | gctctgacat | tctgattcga | atgacactgt | 1680 |
| tcaggaatcg | gaatcctgtc | gattagactg | gacagcttgt | ggcaagtgaa | tttgcctgta | 1740 |
| acaagccaga | ttttttaaaa | tttatattgt | aaatattgtg | tgtgtgtgtg | tgtgtgtata | 1800 |
| tatatatata | tatgtacagt | tatctaagtt | aatttaaagt | tgtttgtgcc | ttttatttt | 1860 |
| tgtttttaat | gctttgatat | ttcaatgtta | gcctcaattt | ctgaacacca | taggtagaat | 1920 |
| gtaaagcttg | tctgatcgtt | caaagcatga | aatggatact | tatatggaaa | ttctgctcag | 1980 |
| atagaatgac | agtccgtcaa | aacagattgt | ttgcaaaggg | gaggcatcag | tgtcttggca | 2040 |
| ggctgatttc | taggtaggaa | atgtggtagc | tcacg | | 2075 |

```
<210> SEQ ID NO 2
<211> LENGTH: 349
<212> TYPE: PRT
<213> ORGANISM: Homo sapiens

<400> SEQUENCE: 2

Met Thr Ala Ala Ser Met Gly Pro Val Arg Val Ala Phe Val Val Leu
1               5                   10                  15

Leu Ala Leu Cys Ser Arg Pro Ala Val Gly Gln Asn Cys Ser Gly Pro
            20                  25                  30

Cys Arg Cys Pro Asp Glu Pro Ala Pro Arg Cys Pro Ala Gly Val Ser
        35                  40                  45

Leu Val Leu Asp Gly Cys Gly Cys Cys Arg Val Cys Ala Lys Gln Leu
    50                  55                  60

Gly Glu Leu Cys Thr Glu Arg Asp Pro Cys Asp Pro His Lys Gly Leu
65              70                  75                  80

Phe Cys Asp Phe Gly Ser Pro Ala Asn Arg Lys Ile Gly Val Cys Thr
                85                  90                  95

Ala Lys Asp Gly Ala Pro Cys Ile Phe Gly Gly Thr Val Tyr Arg Ser
            100                 105                 110

Gly Glu Ser Phe Gln Ser Ser Cys Lys Tyr Gln Cys Thr Cys Leu Asp
        115                 120                 125

Gly Ala Val Gly Cys Met Pro Leu Cys Ser Met Asp Val Arg Leu Pro
    130                 135                 140

Ser Pro Asp Cys Pro Phe Pro Arg Arg Val Lys Leu Pro Gly Lys Cys
145                 150                 155                 160

Cys Glu Glu Trp Val Cys Asp Glu Pro Lys Asp Gln Thr Val Val Gly
                165                 170                 175

Pro Ala Leu Ala Ala Tyr Arg Leu Glu Asp Thr Phe Gly Pro Asp Pro
            180                 185                 190

Thr Met Ile Arg Ala Asn Cys Leu Val Gln Thr Thr Glu Trp Ser Ala
        195                 200                 205

Cys Ser Lys Thr Cys Gly Met Gly Ile Ser Thr Arg Val Thr Asn Asp
    210                 215                 220

Asn Ala Ser Cys Arg Leu Glu Lys Gln Ser Arg Leu Cys Met Val Arg
225                 230                 235                 240

Pro Cys Glu Ala Asp Leu Glu Glu Asn Ile Lys Lys Gly Lys Lys Cys
                245                 250                 255

Ile Arg Thr Pro Lys Ile Ser Lys Pro Ile Lys Phe Glu Leu Ser Gly
            260                 265                 270

Cys Thr Ser Met Lys Thr Tyr Arg Ala Lys Phe Cys Gly Val Cys Thr
        275                 280                 285

Asp Gly Arg Cys Cys Thr Pro His Arg Thr Thr Thr Leu Pro Val Glu
    290                 295                 300

Phe Lys Cys Pro Asp Gly Glu Val Met Lys Lys Asn Met Met Phe Ile
305                 310                 315                 320

Lys Thr Cys Ala Cys His Tyr Asn Cys Pro Gly Asp Asn Asp Ile Phe
                325                 330                 335

Glu Ser Leu Tyr Tyr Arg Lys Met Tyr Gly Asp Met Ala
            340                 345

<210> SEQ ID NO 3
<211> LENGTH: 21
<212> TYPE: DNA
```

```
<213> ORGANISM: artificial sequence
<220> FEATURE:
<223> OTHER INFORMATION: Ig Heavy chain primer

<400> SEQUENCE: 3
tgccaggggg aagaccgatg g                                              21

<210> SEQ ID NO 4
<211> LENGTH: 23
<212> TYPE: DNA
<213> ORGANISM: artificial sequence
<220> FEATURE:
<223> OTHER INFORMATION: Ig heavy chain primer

<400> SEQUENCE: 4
gctgggcgcc cgggaagtat gta                                            23

<210> SEQ ID NO 5
<211> LENGTH: 20
<212> TYPE: DNA
<213> ORGANISM: artificial sequence
<220> FEATURE:
<223> OTHER INFORMATION: Ig Heavy chain primer

<400> SEQUENCE: 5
atggagtttg grctgagctg                                                20

<210> SEQ ID NO 6
<211> LENGTH: 23
<212> TYPE: DNA
<213> ORGANISM: artificial sequence
<220> FEATURE:
<223> OTHER INFORMATION: Ig heavy chain primer

<400> SEQUENCE: 6
cggcggtgtt tccattcggt gat                                            23

<210> SEQ ID NO 7
<211> LENGTH: 22
<212> TYPE: DNA
<213> ORGANISM: artificial sequence
<220> FEATURE:
<223> OTHER INFORMATION: Ig heavy chain primer

<400> SEQUENCE: 7
gggcgcctga gttccacgac ac                                             22

<210> SEQ ID NO 8
<211> LENGTH: 23
<212> TYPE: DNA
<213> ORGANISM: artificial sequence
<220> FEATURE:
<223> OTHER INFORMATION: Ig heavy chain primer

<400> SEQUENCE: 8
gtcttccccc tggcaccctc ctc                                            23

<210> SEQ ID NO 9
<211> LENGTH: 24
<212> TYPE: DNA
<213> ORGANISM: artificial sequence
<220> FEATURE:
<223> OTHER INFORMATION: Ig heavy chain primer

<400> SEQUENCE: 9
cccgcggctt tgtcttggca ttat                                           24
```

<210> SEQ ID NO 10
<211> LENGTH: 21
<212> TYPE: DNA
<213> ORGANISM: artificial sequence
<220> FEATURE:
<223> OTHER INFORMATION: Ig heavy chain primer

<400> SEQUENCE: 10
ctggctgaat ggcaaggagt a                                                 21

<210> SEQ ID NO 11
<211> LENGTH: 19
<212> TYPE: DNA
<213> ORGANISM: artificial sequence
<220> FEATURE:
<223> OTHER INFORMATION: Ig heavy chain primer

<400> SEQUENCE: 11
gggcacccag acctacatc                                                    19

<210> SEQ ID NO 12
<211> LENGTH: 22
<212> TYPE: DNA
<213> ORGANISM: artificial sequence
<220> FEATURE:
<223> OTHER INFORMATION: Ig heavy chain primer

<400> SEQUENCE: 12
ctccggctgc ccattgctct cc                                                22

<210> SEQ ID NO 13
<211> LENGTH: 2197
<212> TYPE: DNA
<213> ORGANISM: Homo sapiens

<400> SEQUENCE: 13
ggtaccttct gaggcggaaa gaaccagctg tggaatgtgt gtcagttagg gtgtggaaag      60
tccccaggct ccccagcagg cagaagtatg caaagcatgc atctcaatta gtcagcaacc     120
aggtgtggaa agtccccagg ctccccagca ggcagaagta tgcaaagcat gcatctcaat     180
tagtcagcaa ccatagtccc gcccctaact ccgcccatcc cgcccctaac tccgcccagt     240
tccgcccatt ctccgcccca tggctgacta atttttttta tttatgcaga ggccgaggcc     300
gcctcggcct ctgagctatt ccagaagtag tgaggaggct tttttggagg cctaggcttt     360
tgcaaaaagc ggccgcaagc taattcgccc ttcggcggtg tttccattcg tgatcagga     420 ctgaacacac aggaatcacc atggagtttg tgctgagctg gttttccttt gttgctatat     480
taaaaggtgt ccagtgtgag gtcagctggt gcaatctggg ggaggcttg gtacatcctg     540 gggggtccct gagactctcc tgtgcaggct ctggattcac cttcagtagc tatggtatgc     600
actgggttcg ccaggctcca ggaaaaggtc tggagtgggt atcaggtatt ggtactggtg     660
gtggcacata ctctacagac tccgtgaagg gccgattcac catctccaga gacaatgcca     720
agaactcctt gtatcttcaa atgaacagcc tgagagccga ggacatggct gtgtattact     780
gtgcaagagg agattactat ggttcgggga gtttctttga ctgctggggc cagggaaccc     840
tggtcaccgt ctcctcagcc tccaccaagg gcccatcggt cttccccctg gcaccctcct     900
ccaagagcac ctctggggc acagcggcc tgggctgcct ggtcaaggac tacttccccg     960
aaccggtgac ggtgtcgtgg aactcaggcg ccctgaccag cggcgtgcac accttcccgg    1020

```
ctgtcctaca gtcctcagga ctctactccc tcagcagcgt ggtgaccgtg ccctccagca   1080
gcttgggcac ccagacctac atctgcaacg tgaatcacaa gcccagcaac accaaggtgg   1140
acaagagagt tgagcccaaa tcttgtgaca aaactcacac atgcccaccg tgcccagcac   1200
ctgaactcct ggggggaccg tcagtcttcc tcttccccec aaaacccaag gacaccctca   1260
tgatctcccg gacccctgag gtcacatgcg tggtggtgga cgtgagccac gaagaccctg   1320
aggtcaagtt caactggtac gtggacggcg tggaggtgca taatgccaag acaaagccgc   1380
gggaggagca gtacaacagc acgtaccggg tggtcagcgt cctcaccgtc ctgcaccagg   1440
actggctgaa tggcaaggag tacaagtgca aggtctccaa caaagccctc ccagccccca   1500
tcgagaaaac catctccaaa gccaaagggc agccccgaga accacaggtg tacaccctgc   1560
ccccatcccg ggaggagatg accaagaacc aggtcagcct gacctgcctg gtcaaaggct   1620
tctatcccag cgacatcgcc gtggagtggg agagcaatgg gcagccggag aacaactaca   1680
agaccacgcc tcccgtgctg gactccgacg gctccttctt cctctacagc aagctcaccg   1740
tggacaagag caggtggcag caggggaacg tcttctcatg ctccgtgatg catgaggctc   1800
tgcacaacca ctacacgcag aagagcctct ccctgtctcc gggtaaatga gtgcgacggc   1860
cggcaagccc cgctccccgg gctctcgcgg tcgcacgagg atgcttggca cgtacccccct  1920 gtacatactt cccgggcgcc cagcaagggc gaattgatcc agacatgata agatacattg   1980
atgagtttgg acaaaccaca actagaatgc agtgaaaaaa atgctttatt tgtgaaattt   2040
gtgatgctat tgctttattt gtaaccatta taagctgcaa taaacaagtt aacaacaaca   2100
attgcattca ttttatgttt caggttcagg gggaggtgtg ggaggttttt taaagcaagt   2160
aaaacctcta caaatgtggt atggctgatt atgatca                            2197
```

<210> SEQ ID NO 14
<211> LENGTH: 469
<212> TYPE: PRT
<213> ORGANISM: Homo sapiens

<400> SEQUENCE: 14

```
Met Glu Phe Val Leu Ser Trp Val Phe Leu Val Ala Ile Leu Lys Gly
1               5                   10                  15

Val Gln Cys Glu Gly Gln Leu Val Gln Ser Gly Gly Gly Leu Val His
            20                  25                  30

Pro Gly Gly Ser Leu Arg Leu Ser Cys Ala Gly Ser Gly Phe Thr Phe
        35                  40                  45

Ser Ser Tyr Gly Met His Trp Val Arg Gln Ala Pro Gly Lys Gly Leu
    50                  55                  60

Glu Trp Val Ser Gly Ile Gly Thr Gly Gly Thr Tyr Ser Thr Asp
65                  70                  75                  80

Ser Val Lys Gly Arg Phe Thr Ile Ser Arg Asp Asn Ala Lys Asn Ser
                85                  90                  95

Leu Tyr Leu Gln Met Asn Ser Leu Arg Ala Glu Asp Met Ala Val Tyr
            100                 105                 110

Tyr Cys Ala Arg Gly Asp Tyr Tyr Gly Ser Gly Ser Phe Phe Asp Cys
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
```

```
                165                 170                 175
Thr Val Ser Trp Asn Ser Gly Ala Leu Thr Ser Gly Val His Thr Phe
            180                 185                 190
Pro Ala Val Leu Gln Ser Ser Gly Leu Tyr Ser Leu Ser Ser Val Val
            195                 200                 205
Thr Val Pro Ser Ser Ser Leu Gly Thr Gln Thr Tyr Ile Cys Asn Val
    210                 215                 220
Asn His Lys Pro Ser Asn Thr Lys Val Asp Lys Arg Val Glu Pro Lys
225                 230                 235                 240
Ser Cys Asp Lys Thr His Thr Cys Pro Pro Cys Pro Ala Pro Glu Leu
                245                 250                 255
Leu Gly Gly Pro Ser Val Phe Leu Phe Pro Pro Lys Pro Lys Asp Thr
            260                 265                 270
Leu Met Ile Ser Arg Thr Pro Glu Val Thr Cys Val Val Val Asp Val
        275                 280                 285
Ser His Glu Asp Pro Glu Val Lys Phe Asn Trp Tyr Val Asp Gly Val
    290                 295                 300
Glu Val His Asn Ala Lys Thr Lys Pro Arg Glu Glu Gln Tyr Asn Ser
305                 310                 315                 320
Thr Tyr Arg Val Val Ser Val Leu Thr Val Leu His Gln Asp Trp Leu
                325                 330                 335
Asn Gly Lys Glu Tyr Lys Cys Lys Val Ser Asn Lys Ala Leu Pro Ala
            340                 345                 350
Pro Ile Glu Lys Thr Ile Ser Lys Ala Lys Gly Gln Pro Arg Glu Pro
            355                 360                 365
Gln Val Tyr Thr Leu Pro Pro Ser Arg Glu Glu Met Thr Lys Asn Gln
    370                 375                 380
Val Ser Leu Thr Cys Leu Val Lys Gly Phe Tyr Pro Ser Asp Ile Ala
385                 390                 395                 400
Val Glu Trp Glu Ser Asn Gly Gln Pro Glu Asn Asn Tyr Lys Thr Thr
                405                 410                 415
Pro Pro Val Leu Asp Ser Asp Gly Ser Phe Phe Leu Tyr Ser Lys Leu
            420                 425                 430
Thr Val Asp Lys Ser Arg Trp Gln Gln Gly Asn Val Phe Ser Cys Ser
            435                 440                 445
Val Met His Glu Ala Leu His Asn His Tyr Thr Gln Lys Ser Leu Ser
        450                 455                 460
Leu Ser Pro Gly Lys
465

<210> SEQ ID NO 15
<211> LENGTH: 20
<212> TYPE: DNA
<213> ORGANISM: artificial sequence
<220> FEATURE:
<223> OTHER INFORMATION: Ig Light chain primer

<400> SEQUENCE: 15
cgggaagatg aagacagatg                                              20

<210> SEQ ID NO 16
<211> LENGTH: 20
<212> TYPE: DNA
<213> ORGANISM: artificial sequence
<220> FEATURE:
<223> OTHER INFORMATION: Ig light chain primer
```

<400> SEQUENCE: 16
aaggatggga gggggtcagg                                            20

<210> SEQ ID NO 17
<211> LENGTH: 24
<212> TYPE: DNA
<213> ORGANISM: artificial sequence
<220> FEATURE:
<223> OTHER INFORMATION: Ig Light chain primer

<400> SEQUENCE: 17
cccgctcagc tcctggggct cctg                                       24

<210> SEQ ID NO 18
<211> LENGTH: 22
<212> TYPE: DNA
<213> ORGANISM: artificial sequence
<220> FEATURE:
<223> OTHER INFORMATION: Ig light chain primer

<400> SEQUENCE: 18
tcagwcycag tcaggacaca gc                                         22

<210> SEQ ID NO 19
<211> LENGTH: 1433
<212> TYPE: DNA
<213> ORGANISM: Homo sapiens

<400> SEQUENCE: 19
ggtaccttct gaggcggaaa gaaccagctg tggaatgtgt gtcagttagg gtgtggaaag    60
tccccaggct ccccagcagg cagaagtatg caaagcatgc atctcaatta gtcagcaacc   120
aggtgtggaa agtccccagg ctccccagca ggcagaagta tgcaaagcat gcatctcaat   180
tagtcagcaa ccatagtccc gcccctaact ccgcccatcc cgccctaac tccgcccagt    240 tccgcccatt ctccgcccca tggctgacta atttttttta tttatgcaga ggccgaggcc   300
gcctcggcct ctgagctatt ccagaagtag tgaggaggct ttttggagg cctaggcttt    360 tgcaaaaagc ggccgcaagc taattcgccc tttcagtctc agtcaggaca cagcatggac   420
atgagggtcc tcgctcagct cctggggctc ctgctgctct gtttcccagg tgccagatgt   480
gacatccaga tgacccagtc tccatcctca ctgtctgcat ctgtaggaga cagagtcacc   540
atcacttgtc gggcgagtca gggtattagc agctggttag cctggtatca gcagaaacca   600
gagaaagccc ctaagtccct gatctatgct gcatccagtt tgcaaagtgg ggtcccatca   660
aggttcagcg gcagtggatc tgggacagat ttcactctca ccatcagcag cctgcagcct   720
gaagattttg caacttatta ctgccaacag tataatagtt accctccac ttttggccag    780 gggaccaagc tggagatcaa acgaactgtg gctgcaccat ctgtcttcat cttcccgcca   840
tctgatgagc agttgaaatc tggaactgcc tctgttgtgt gcctgctgaa taacttctat   900
cccagagagg ccaaagtaca gtggaaggtg gataacgccc tccaatcggg taactcccag   960
gagagtgtca cagagcagga cagcaaggac agcacctaca gcctcagcag caccctgacg  1020
ctgagcaaag cagactacga gaacacaaa gtctacgcct gcgaagtcac ccatcagggc   1080
ctgagctcgc ccgtcacaaa gagcttcaac aggggagagt gttagaggga gaagtgcccc  1140
cacctgctcc tcagttccag cctgaccccc tccatccttt aagggcgaat tgatccagac  1200 atgataaagat acattgatga gtttggacaa accacaacta gaatgcagtg aaaaaaatgc  1260
tttatttgtg aaatttgtga tgctattgct ttatttgtaa ccattataag ctgcaataaa  1320

```
caagttaaca acaacaattg cattcatttt atgtttcagg ttcagggggga ggtgtgggag   1380 gtttttaaa gcaagtaaaa cctctacaaa tgtggtatgg ctgattatga tca           1433
```

<210> SEQ ID NO 20
<211> LENGTH: 236
<212> TYPE: PRT
<213> ORGANISM: Homo sapiens

<400> SEQUENCE: 20

```
Met Asp Met Arg Val Leu Ala Gln Leu Leu Gly Leu Leu Leu Leu Cys
1               5                   10                  15

Phe Pro Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Gly Ile Ser Ser Trp Leu Ala Trp Tyr Gln Gln Lys Pro Glu Lys
    50                  55                  60

Ala Pro Lys Ser Leu Ile Tyr Ala Ala Ser Ser Leu Gln Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Tyr Asn Ser Tyr Pro Pro Thr Phe Gly Gln Gly Thr Lys Leu Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235
```

<210> SEQ ID NO 21
<211> LENGTH: 62
<212> TYPE: PRT
<213> ORGANISM: artificial
<220> FEATURE:
<223> OTHER INFORMATION: synthetic peptide

<400> SEQUENCE: 21

```
Cys Ile Phe Gly Gly Thr Val Tyr Arg Ser Gly Glu Ser Phe Gln Ser
1               5                   10                  15

Ser Cys Lys Tyr Gln Cys Thr Cys Leu Asp Gly Ala Val Gly Cys Met
            20                  25                  30

Pro Leu Cys Ser Met Asp Val Arg Leu Pro Ser Pro Asp Cys Pro Phe
        35                  40                  45

Pro Arg Arg Val Lys Leu Pro Gly Lys Cys Cys Glu Glu Trp
    50                  55                  60
```

<210> SEQ ID NO 22
<211> LENGTH: 24
<212> TYPE: PRT
<213> ORGANISM: artificial
<220> FEATURE:
<223> OTHER INFORMATION: synthetic peptide

<400> SEQUENCE: 22

Cys Pro Leu Cys Ser Met Asp Val Arg Leu Pro Ser Pro Asp Cys Pro
1               5                   10                  15

Phe Pro Arg Arg Val Lys Leu Pro
            20

<210> SEQ ID NO 23
<211> LENGTH: 18
<212> TYPE: PRT
<213> ORGANISM: artificial
<220> FEATURE:
<223> OTHER INFORMATION: synthetic peptide

<400> SEQUENCE: 23

Arg Leu Pro Ser Pro Asp Ser Pro Phe Pro Arg Arg Val Lys Leu Pro
1               5                   10                  15

Gly Lys

<210> SEQ ID NO 24
<211> LENGTH: 15
<212> TYPE: PRT
<213> ORGANISM: artificial
<220> FEATURE:
<223> OTHER INFORMATION: synthetic peptide

<400> SEQUENCE: 24

Arg Leu Pro Ser Pro Asp Cys Pro Phe Pro Arg Arg Val Lys Leu
1               5                   10                  15

<210> SEQ ID NO 25
<211> LENGTH: 13
<212> TYPE: PRT
<213> ORGANISM: artificial
<220> FEATURE:
<223> OTHER INFORMATION: synthetic peptide

<400> SEQUENCE: 25

Arg Leu Pro Ser Pro Asp Cys Pro Phe Pro Arg Arg Val
1               5                   10

<210> SEQ ID NO 26
<211> LENGTH: 14
<212> TYPE: PRT
<213> ORGANISM: artificial
<220> FEATURE:
<223> OTHER INFORMATION: synthetic peptide

<400> SEQUENCE: 26

Leu Pro Ser Pro Asp Cys Pro Phe Pro Arg Arg Val Lys Leu
1               5                   10

<210> SEQ ID NO 27
<211> LENGTH: 198
<212> TYPE: PRT
<213> ORGANISM: Homo sapiens

<400> SEQUENCE: 27

Met Thr Ala Ala Ser Met Gly Pro Val Arg Val Ala Phe Val Val Leu
1               5                   10                  15

Leu Ala Leu Cys Ser Arg Pro Ala Val Gly Gln Asn Cys Ser Gly Pro
            20                  25                  30

Cys Arg Cys Pro Asp Glu Pro Ala Pro Arg Cys Pro Ala Gly Val Ser
        35                  40                  45

Leu Val Leu Asp Gly Cys Gly Cys Arg Val Cys Ala Lys Gln Leu
    50                  55                  60

Gly Glu Leu Cys Thr Glu Arg Asp Pro Cys Asp Pro His Lys Gly Leu
65                  70                  75                  80

Phe Cys Asp Phe Gly Ser Pro Ala Asn Arg Lys Ile Gly Val Cys Thr
                85                  90                  95

Ala Lys Asp Gly Ala Pro Cys Ile Phe Gly Gly Thr Val Tyr Arg Ser
            100                 105                 110

Gly Glu Ser Phe Gln Ser Ser Cys Lys Tyr Gln Cys Thr Cys Leu Asp
            115                 120                 125

Gly Ala Val Gly Cys Met Pro Leu Cys Ser Met Asp Val Arg Leu Pro
        130                 135                 140

Ser Pro Asp Cys Pro Phe Pro Arg Arg Val Lys Leu Pro Gly Lys Cys
145                 150                 155                 160

Cys Glu Glu Trp Val Cys Asp Glu Pro Lys Asp Gln Thr Val Val Gly
                165                 170                 175

Pro Ala Leu Ala Ala Tyr Arg Leu Glu Asp Thr Phe Gly Pro Asp Pro
            180                 185                 190

Thr Met Ile Arg Ala Asn
        195

<210> SEQ ID NO 28
<211> LENGTH: 84
<212> TYPE: PRT
<213> ORGANISM: artificial
<220> FEATURE:
<223> OTHER INFORMATION: synthetic peptide

<400> SEQUENCE: 28

Ala Lys Asp Gly Ala Pro Cys Ile Phe Gly Gly Thr Val Tyr Arg Ser
1               5                   10                  15

Gly Glu Ser Phe Gln Ser Ser Cys Lys Tyr Gln Cys Thr Cys Leu Asp
            20                  25                  30

Gly Ala Val Gly Cys Met Pro Leu Cys Ser Met Asp Val Arg Leu Pro
        35                  40                  45

Ser Pro Asp Cys Pro Phe Pro Arg Arg Val Lys Leu Pro Gly Lys Cys
        50                  55                  60

Cys Glu Glu Trp Val Cys Asp Glu Pro Lys Asp Gln Thr Val Val Gly
65                  70                  75                  80

Pro Ala Leu Ala

<210> SEQ ID NO 29
<211> LENGTH: 198
<212> TYPE: PRT
<213> ORGANISM: Bos taurus

<400> SEQUENCE: 29

Met Ser Ala Thr Gly Leu Gly Pro Val Arg Cys Ala Phe Val Leu Leu
1               5                   10                  15

Leu Ala Leu Cys Ser Arg Pro Ala Ser Ser Gln Asp Cys Ser Ala Pro
            20                  25                  30

```
Cys Gln Cys Pro Ala Gly Pro Ala Pro Arg Cys Pro Ala Gly Val Ser
        35                  40                  45

Leu Val Leu Asp Gly Cys Gly Cys Cys Arg Val Cys Ala Lys Gln Leu
    50                  55                  60

Ser Glu Leu Cys Thr Glu Arg Asp Pro Cys Asp Pro His Lys Gly Leu
65                  70                  75                  80

Phe Cys Asp Phe Gly Ser Pro Ala Asn Arg Lys Ile Gly Val Cys Thr
                85                  90                  95

Ala Lys Asp Gly Ala Pro Cys Val Phe Gly Gly Thr Val Tyr Gln Ser
                100                 105                 110

Gly Glu Ser Phe Gln Ser Ser Cys Lys Tyr Gln Cys Thr Cys Leu Asp
                115                 120                 125

Gly Ser Val Gly Cys Val Pro Leu Cys Ser Val Asp Val Arg Leu Pro
    130                 135                 140

Ser Pro Asp Cys Pro Phe Pro Arg Arg Val Lys Leu Pro Gly Lys Cys
145                 150                 155                 160

Cys Glu Glu Trp Val Cys Asp Glu Pro Lys Glu His Thr Val Gly
                165                 170                 175

Pro Ala Leu Ala Ala Tyr Arg Pro Glu Asp Thr Phe Gly Pro Asp Pro
                180                 185                 190

Thr Met Ile Arg Ala Asn
            195

<210> SEQ ID NO 30
<211> LENGTH: 198
<212> TYPE: PRT
<213> ORGANISM: Sus scrofa

<400> SEQUENCE: 30

Met Ser Ala Thr Gly Leu Ser Pro Val Arg Cys Ala Phe Val Leu Leu
1               5                   10                  15

Leu Ala Leu Cys Ser Arg Pro Ala Ser Gly Gln Asp Cys Ser Gly Gln
                20                  25                  30

Cys Gln Cys Ala Ala Gly Lys Arg Arg Ala Cys Pro Ala Gly Val Ser
        35                  40                  45

Leu Val Leu Asp Gly Cys Gly Cys Cys Arg Leu Cys Ala Lys Gln Leu
    50                  55                  60

Gly Glu Leu Cys Thr Glu Arg Asp Pro Cys Asp Pro His Lys Gly Leu
65                  70                  75                  80

Phe Cys Asp Phe Gly Ser Pro Ala Asn Arg Lys Ile Gly Val Cys Thr
                85                  90                  95

Ala Lys Asp Gly Ala Pro Cys Val Phe Gly Gly Thr Val Tyr Arg Ser
                100                 105                 110

Gly Glu Ser Phe Gln Ser Ser Cys Lys Tyr Gln Cys Thr Cys Leu Asp
                115                 120                 125

Gly Ala Val Gly Cys Val Pro Leu Cys Ser Met Asp Val Arg Leu Pro
    130                 135                 140

Ser Pro Asp Cys Pro Phe Pro Arg Arg Val Lys Leu Pro Gly Lys Cys
145                 150                 155                 160

Cys Glu Glu Trp Val Cys Asp Glu Pro Lys Asp His Thr Val Val Gly
                165                 170                 175

Pro Ala Leu Ala Ala Tyr Arg Leu Glu Asp Thr Phe Gly Pro Asp Pro
                180                 185                 190

Thr Met Met Arg Ala Asn
```

<210> SEQ ID NO 31
<211> LENGTH: 196
<212> TYPE: PRT
<213> ORGANISM: Rattus norvegicus

<400> SEQUENCE: 31

```
Met Leu Ala Ser Val Ala Gly Pro Val Ser Leu Ala Leu Val Leu Leu
1               5                   10                  15

Leu Cys Thr Arg Pro Ala Thr Gly Gln Asp Cys Ser Ala Gln Cys Gln
                20                  25                  30

Cys Ala Ala Glu Ala Ala Pro Arg Cys Pro Ala Gly Val Ser Leu Val
            35                  40                  45

Leu Asp Gly Cys Gly Cys Cys Arg Val Cys Ala Lys Gln Leu Gly Glu
        50                  55                  60

Leu Cys Thr Glu Arg Asp Pro Cys Asp Pro His Lys Gly Leu Phe Cys
65                  70                  75                  80

Asp Phe Gly Ser Pro Ala Asn Arg Lys Ile Gly Val Cys Thr Ala Lys
                85                  90                  95

Asp Gly Ala Pro Cys Val Phe Gly Gly Ser Val Tyr Arg Ser Gly Glu
                100                 105                 110

Ser Phe Gln Ser Ser Cys Lys Tyr Gln Cys Thr Cys Leu Asp Gly Ala
            115                 120                 125

Val Gly Cys Val Pro Leu Cys Ser Met Asp Val Arg Leu Pro Ser Pro
        130                 135                 140

Asp Cys Pro Phe Pro Arg Arg Val Lys Leu Pro Gly Lys Cys Cys Glu
145                 150                 155                 160

Glu Trp Val Cys Asp Glu Pro Lys Asp Arg Thr Val Val Gly Pro Ala
                165                 170                 175

Leu Ala Ala Tyr Arg Leu Glu Asp Thr Phe Gly Pro Asp Pro Thr Met
                180                 185                 190

Met Arg Ala Asn
        195
```

<210> SEQ ID NO 32
<211> LENGTH: 197
<212> TYPE: PRT
<213> ORGANISM: Mus musculus

<400> SEQUENCE: 32

```
Met Leu Ala Ser Val Ala Gly Pro Ile Ser Leu Ala Leu Val Leu Leu
1               5                   10                  15

Ala Leu Cys Thr Arg Pro Ala Thr Gly Gln Asp Cys Ser Ala Gln Cys
                20                  25                  30

Gln Cys Ala Ala Glu Ala Ala Pro His Cys Pro Ala Gly Val Ser Leu
            35                  40                  45

Val Leu Asp Gly Cys Gly Cys Cys Arg Val Cys Ala Lys Gln Leu Gly
        50                  55                  60

Glu Leu Cys Thr Glu Arg Asp Pro Cys Asp Pro His Lys Gly Leu Phe
65                  70                  75                  80

Cys Asp Phe Gly Ser Pro Ala Asn Arg Lys Ile Gly Val Cys Thr Ala
                85                  90                  95
```

```
Lys Asp Gly Ala Pro Cys Val Phe Gly Ser Val Tyr Arg Ser Gly
            100                 105                 110

Glu Ser Phe Gln Ser Ser Cys Lys Tyr Gln Cys Thr Cys Leu Asp Gly
        115                 120                 125

Ala Val Gly Cys Val Pro Leu Cys Ser Met Asp Val Arg Leu Pro Ser
    130                 135                 140

Pro Asp Cys Pro Phe Pro Arg Arg Val Lys Leu Pro Gly Lys Cys Cys
145                 150                 155                 160

Lys Glu Trp Val Cys Asp Glu Pro Lys Asp Arg Thr Ala Val Gly Pro
                165                 170                 175

Ala Leu Ala Ala Tyr Arg Leu Glu Asp Thr Phe Gly Pro Asp Pro Thr
            180                 185                 190

Met Met Arg Ala Asn
        195

<210> SEQ ID NO 33
<211> LENGTH: 14
<212> TYPE: PRT
<213> ORGANISM: artificial
<220> FEATURE:
<223> OTHER INFORMATION: synthetic peptide

<400> SEQUENCE: 33

Pro Leu Ser Ser Met Asp Val Arg Leu Pro Ser Pro Asp Ser
1               5                   10

<210> SEQ ID NO 34
<211> LENGTH: 13
<212> TYPE: PRT
<213> ORGANISM: artificial
<220> FEATURE:
<223> OTHER INFORMATION: synthetic peptide

<400> SEQUENCE: 34

Arg Leu Pro Ser Pro Asp Ser Pro Phe Pro Arg Arg Val
1               5                   10

<210> SEQ ID NO 35
<211> LENGTH: 10
<212> TYPE: PRT
<213> ORGANISM: artificial
<220> FEATURE:
<223> OTHER INFORMATION: synthetic peptide

<400> SEQUENCE: 35

Ser Pro Asp Ser Pro Phe Pro Arg Arg Val
1               5                   10

<210> SEQ ID NO 36
<211> LENGTH: 10
<212> TYPE: PRT
<213> ORGANISM: artificial
<220> FEATURE:
<223> OTHER INFORMATION: synthetic peptide

<400> SEQUENCE: 36

Ser Pro Asp Cys Pro Phe Pro Arg Arg Val
1               5                   10

<210> SEQ ID NO 37
<211> LENGTH: 9
<212> TYPE: PRT
<213> ORGANISM: artificial
<220> FEATURE:
```

```
<223> OTHER INFORMATION: synthetic peptide

<400> SEQUENCE: 37

Pro Asp Ser Pro Phe Pro Arg Arg Val
1               5

<210> SEQ ID NO 38
<211> LENGTH: 9
<212> TYPE: PRT
<213> ORGANISM: artificial
<220> FEATURE:
<223> OTHER INFORMATION: synthetic peptide

<400> SEQUENCE: 38

Cys Pro Phe Pro Arg Arg Val Lys Leu
1               5

<210> SEQ ID NO 39
<211> LENGTH: 8
<212> TYPE: PRT
<213> ORGANISM: artificial
<220> FEATURE:
<223> OTHER INFORMATION: synthetic peptide

<400> SEQUENCE: 39

Asp Ser Pro Phe Pro Arg Arg Val
1               5

<210> SEQ ID NO 40
<211> LENGTH: 8
<212> TYPE: PRT
<213> ORGANISM: artificial
<220> FEATURE:
<223> OTHER INFORMATION: synthetic peptide

<400> SEQUENCE: 40

Cys Phe Pro Arg Arg Val Lys Leu
1               5

<210> SEQ ID NO 41
<211> LENGTH: 7
<212> TYPE: PRT
<213> ORGANISM: artificial
<220> FEATURE:
<223> OTHER INFORMATION: synthetic peptide

<400> SEQUENCE: 41

Cys Pro Arg Arg Val Lys Leu
1               5

<210> SEQ ID NO 42
<211> LENGTH: 6
<212> TYPE: PRT
<213> ORGANISM: artificial
<220> FEATURE:
<223> OTHER INFORMATION: synthetic peptide

<400> SEQUENCE: 42

Cys Arg Arg Val Lys Leu
1               5
```

```
<210> SEQ ID NO 43
<211> LENGTH: 5
<212> TYPE: PRT
<213> ORGANISM: artificial
<220> FEATURE:
<223> OTHER INFORMATION: synthetic peptide

<400> SEQUENCE: 43

Cys Arg Val Lys Leu
1               5
```